United States Patent
Lauf et al.

(10) Patent No.: US 12,336,917 B2
(45) Date of Patent: Jun. 24, 2025

(54) STEERABLE IMPLANT ASSEMBLY

(71) Applicant: LIFE SPINE, INC., Huntley, IL (US)

(72) Inventors: Garrett D. Lauf, Hampshire, IL (US); Daniel P. Predick, Wheat Ridge, CO (US); Madeline Wolters, St. Charles, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 518 days.

(21) Appl. No.: 17/740,471

(22) Filed: May 10, 2022

(65) Prior Publication Data

US 2022/0265440 A1 Aug. 25, 2022

Related U.S. Application Data

(63) Continuation-in-part of application No. 16/875,465, filed on May 15, 2020, now Pat. No. 11,337,825.

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4465* (2013.01); *A61F 2002/30556* (2013.01);
(Continued)

(58) Field of Classification Search
CPC . A61F 2/4425; A61F 2/4455; A61F 2002/443
See application file for complete search history.

(56) References Cited

U.S. PATENT DOCUMENTS

| 904,434 A | 11/1908 | Huff |
| 1,925,385 A | 9/1933 | Humes |

(Continued)

FOREIGN PATENT DOCUMENTS

| CN | 102427769 A | 4/2012 |
| CN | 205866898 U | 1/2017 |

(Continued)

OTHER PUBLICATIONS

Bacfuse® Spinous Process Fusion Plate Surgical Technique, 2011, Pioneer Surgical, 12 pages.
(Continued)

*Primary Examiner* — Matthew J Lawson
(74) *Attorney, Agent, or Firm* — Foley & Lardner LLP

(57) ABSTRACT

A steerable expandable implant having a lower support member and an upper support member, the upper support member movable relative to the lower support member between a collapsed position and an expanded position. The implant also includes a first control member coupled to the lower support member, where manipulation of the first control member causes the lower support member to move relative to the upper support member. The implant further includes a pivot member configured to receive a tool, the tool and the pivot member rotatable relative to the lower support member between a first position and a second position, where the pivot member includes an aperture and an axis of the aperture is angularly offset from an axis of the first control member in the first position and the axis of the aperture is angularly aligned with the axis of the first control member in the second position.

16 Claims, 30 Drawing Sheets

(52) U.S. Cl.
CPC .............. *A61F 2002/30579* (2013.01); *A61F 2002/4627* (2013.01); *A61F 2002/4628* (2013.01); *A61F 2002/4629* (2013.01)

(56) References Cited

U.S. PATENT DOCUMENTS

| | | | |
|---|---|---|---|
| 3,846,846 A | 11/1974 | Fischer |
| 4,466,426 A | 8/1984 | Blackman |
| 4,636,217 A | 1/1987 | Ogilvie et al. |
| 4,743,256 A | 5/1988 | Brantigan |
| 4,863,476 A | 9/1989 | Shepperd |
| 5,098,435 A | 3/1992 | Stednitz et al. |
| 5,192,327 A | 3/1993 | Brantigan |
| 5,236,460 A | 8/1993 | Barber |
| 5,390,683 A | 2/1995 | Pisharodi |
| 5,522,899 A | 6/1996 | Michelson |
| 5,609,635 A | 3/1997 | Michelson |
| 5,645,599 A | 7/1997 | Samani |
| 5,658,335 A | 8/1997 | Allen |
| 5,658,337 A | 8/1997 | Kohrs et al. |
| 5,776,199 A | 7/1998 | Michelson |
| 5,836,948 A | 11/1998 | Zucherman et al. |
| 5,860,977 A | 1/1999 | Zucherman et al. |
| 5,876,404 A | 3/1999 | Zucherman et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,193 A | 6/2000 | Hochshuler et al. |
| 6,113,638 A | 9/2000 | Williams et al. |
| 6,126,689 A | 10/2000 | Brett |
| 6,129,763 A | 10/2000 | Chauvin et al. |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,290,724 B1 | 9/2001 | Marino |
| 6,302,914 B1 | 10/2001 | Michelson |
| 6,375,682 B1 | 4/2002 | Fleischmann et al. |
| 6,409,766 B1 | 6/2002 | Brett |
| 6,443,989 B1 | 9/2002 | Jackson |
| 6,443,990 B1 | 9/2002 | Aebi et al. |
| 6,447,544 B1 | 9/2002 | Michelson |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,576,016 B1 | 6/2003 | Hochshuler et al. |
| 6,613,091 B1 | 9/2003 | Zdeblick et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,752,832 B2 | 6/2004 | Neumann |
| 6,773,460 B2 | 8/2004 | Jackson |
| 6,796,983 B1 | 9/2004 | Zucherman et al. |
| 6,800,092 B1 | 10/2004 | Williams et al. |
| 6,849,093 B2 | 2/2005 | Michelson |
| 7,001,385 B2 | 2/2006 | Bonutti |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,214,243 B2 | 5/2007 | Taylor |
| 7,217,291 B2 | 5/2007 | Zucherman et al. |
| 7,220,280 B2 | 5/2007 | Kast et al. |
| 7,250,055 B1 | 7/2007 | Vanderwalle |
| 7,473,276 B2 | 1/2009 | Aebi et al. |
| 7,503,933 B2 | 3/2009 | Michelson |
| 7,621,950 B1 | 11/2009 | Globerman et al. |
| 7,695,513 B2 | 4/2010 | Zucherman et al. |
| 7,722,674 B1 | 5/2010 | Grotz |
| 7,727,280 B2 | 6/2010 | McLuen |
| 7,731,751 B2 | 6/2010 | Butler et al. |
| 7,789,914 B2 | 9/2010 | Michelson |
| D626,233 S | 10/2010 | Cipoletti et al. |
| 7,824,427 B2 | 11/2010 | Perez-Cruet et al. |
| 7,828,849 B2 | 11/2010 | Lim |
| 7,837,734 B2 | 11/2010 | Zucherman et al. |
| 7,846,188 B2 | 12/2010 | Moskowitz et al. |
| 7,850,733 B2 | 12/2010 | Baynham et al. |
| 7,854,766 B2 | 12/2010 | Moskowitz et al. |
| 7,867,277 B1 | 1/2011 | Tohmeh |
| 7,879,098 B1 | 2/2011 | Simmons, Jr. |
| 7,942,903 B2 | 5/2011 | Moskowitz et al. |
| 7,959,675 B2 | 6/2011 | Gately |
| 7,972,363 B2 | 7/2011 | Moskowitz et al. |
| 8,016,861 B2 | 9/2011 | Mitchell et al. |
| 8,021,430 B2 | 9/2011 | Michelson |
| 8,048,117 B2 | 11/2011 | Zucherman et al. |
| 8,062,375 B2 | 11/2011 | Glerum et al. |
| 8,070,817 B2 | 12/2011 | Gradl et al. |
| 8,071,007 B1 | 12/2011 | Teoh et al. |
| 8,105,382 B2 | 1/2012 | Olmos et al. |
| 8,187,332 B2 | 5/2012 | McLuen |
| 8,231,656 B2 | 7/2012 | Lee et al. |
| 8,241,330 B2 | 8/2012 | Lamborne et al. |
| 8,241,364 B2 | 8/2012 | Hansell et al. |
| 8,252,060 B2 | 8/2012 | Hansell et al. |
| 8,257,370 B2 | 9/2012 | Moskowitz et al. |
| 8,267,939 B2 | 9/2012 | Cipoletti et al. |
| 8,303,663 B2 | 11/2012 | Jimenez et al. |
| 8,308,804 B2 | 11/2012 | Krueger |
| 8,343,190 B1 | 1/2013 | Mueller et al. |
| 8,353,913 B2 | 1/2013 | Moskowitz et al. |
| 8,353,963 B2 | 1/2013 | Glerum |
| 8,366,777 B2 | 2/2013 | Matthis et al. |
| 8,382,801 B2 | 2/2013 | Lamborne et al. |
| 8,382,842 B2 | 2/2013 | Greenhalgh et al. |
| 8,388,686 B2 | 3/2013 | Aebi et al. |
| 8,394,129 B2 | 3/2013 | Lopez et al. |
| 8,398,713 B2 | 3/2013 | Weiman |
| 8,425,607 B2 | 4/2013 | Waugh et al. |
| 8,435,298 B2 | 5/2013 | Weiman |
| 8,444,696 B2 | 5/2013 | Michelson |
| 8,454,706 B2 | 6/2013 | De Beaubien |
| 8,491,659 B2 | 7/2013 | Weiman |
| 8,506,629 B2 | 8/2013 | Weiland |
| 8,518,120 B2 | 8/2013 | Glerum et al. |
| 8,523,944 B2 | 9/2013 | Jimenez et al. |
| 8,529,628 B2 | 9/2013 | Marino et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,597,360 B2 | 12/2013 | McLuen et al. |
| 8,628,578 B2 | 1/2014 | Miller et al. |
| 8,632,595 B2 | 1/2014 | Weiman |
| 8,641,764 B2 | 2/2014 | Gately |
| 8,641,766 B2 | 2/2014 | Donner et al. |
| 8,663,332 B1 | 3/2014 | To et al. |
| 8,679,183 B2 | 3/2014 | Glerum et al. |
| 8,685,098 B2 | 4/2014 | Glerum et al. |
| 8,690,883 B2 | 4/2014 | Collins et al. |
| 8,702,798 B2 | 4/2014 | Matthis et al. |
| 8,709,086 B2 | 4/2014 | Glerum |
| 8,734,516 B2 | 5/2014 | Moskowitz et al. |
| 8,795,366 B2 | 8/2014 | Varela |
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,906,095 B2 | 12/2014 | Christensen et al. |
| 8,926,704 B2 | 1/2015 | Glerum et al. |

(56) References Cited

U.S. PATENT DOCUMENTS

| | | |
|---|---|---|
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 | 5/2015 | Wolters et al. |
| 9,034,045 B2 | 5/2015 | Davenport et al. |
| 9,039,771 B2 | 5/2015 | Glerum et al. |
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |
| 9,149,367 B2 | 10/2015 | Davenport et al. |
| 9,186,258 B2 | 11/2015 | Davenport et al. |
| 9,186,262 B2 | 11/2015 | McLuen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,333,092 B2 | 5/2016 | To et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,474,622 B2 | 10/2016 | McLaughlin et al. |
| 9,480,579 B2 | 11/2016 | Davenport et al. |
| 9,486,325 B2 | 11/2016 | Davenport et al. |
| 9,486,326 B2 | 11/2016 | Gahman et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | McAtamney et al. |
| 9,532,821 B2 | 1/2017 | Moskowitz et al. |
| 9,532,883 B2 | 1/2017 | McLuen et al. |
| 9,539,103 B2 | 1/2017 | McLaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 | 5/2018 | Daffinson et al. |
| 9,968,462 B2 | 5/2018 | Weiman |
| 9,974,665 B2 | 5/2018 | Mcluen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | McLuen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | McLaughlin et al. |
| 10,052,213 B2 | 8/2018 | Glerum et al. |
| 10,058,433 B2 | 8/2018 | Lechmann et al. |
| 10,064,742 B2 | 9/2018 | Taylor et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | McLuen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 | 11/2018 | Dewey et al. |
| 10,143,500 B2 | 12/2018 | Niemiec et al. |
| 10,143,569 B2 | 12/2018 | Weiman et al. |
| 10,154,911 B2 | 12/2018 | Predick et al. |
| 10,159,583 B2 | 12/2018 | Dietzel et al. |
| 10,195,050 B2 | 2/2019 | Palmatier et al. |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | McLuen et al. |
| 10,299,934 B2 | 5/2019 | Seifert et al. |
| 10,307,268 B2 | 6/2019 | Moskowitz et al. |
| 10,350,085 B2 | 7/2019 | Glerum et al. |
| 10,376,386 B2 | 8/2019 | Moskowitz et al. |
| 10,383,741 B2 | 8/2019 | Butler et al. |
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,449,058 B2 | 10/2019 | Lechmann et al. |
| 10,470,894 B2 * | 11/2019 | Foley ............... A61F 2/447 |
| 10,478,319 B2 | 11/2019 | Moskowitz et al. |
| 10,512,550 B2 | 12/2019 | Bechtel et al. |
| 10,531,895 B2 | 1/2020 | Weiman et al. |
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | McLuen et al. |

(56) References Cited

U.S. PATENT DOCUMENTS

| | | |
|---|---|---|
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,573 B2 | 7/2020 | Weiman et al. |
| 10,709,574 B2 | 7/2020 | McLuen et al. |
| 10,722,379 B2 | 7/2020 | McLaughlin et al. |
| 10,729,560 B2 | 8/2020 | Baker et al. |
| 10,729,562 B2 | 8/2020 | Knapp et al. |
| 10,736,754 B2 | 8/2020 | McLuen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |
| 10,786,364 B2 | 9/2020 | Davenport et al. |
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 | 6/2021 | Miller et al. |
| 11,033,401 B2 | 6/2021 | Shoshtaev |
| 11,051,951 B2 | 7/2021 | Robinson et al. |
| 11,065,128 B2 | 7/2021 | Zappacosta et al. |
| 11,083,584 B2 | 8/2021 | Lauf et al. |
| 11,219,535 B1 * | 1/2022 | Hauck .................. A61F 2/4611 |
| 11,234,833 B2 | 2/2022 | Brotman et al. |
| 11,304,817 B2 | 4/2022 | Altarac et al. |
| 11,304,818 B2 | 4/2022 | Butler et al. |
| 11,857,432 B2 | 1/2024 | Keller et al. |
| 2002/0010472 A1 | 1/2002 | Kuslich et al. |
| 2002/0029084 A1 | 3/2002 | Paul et al. |
| 2002/0091447 A1 | 7/2002 | Shimp et al. |
| 2002/0128716 A1 | 9/2002 | Cohen et al. |
| 2002/0143343 A1 | 10/2002 | Castro |
| 2002/0143399 A1 | 10/2002 | Sutcliffe |
| 2002/0147461 A1 | 10/2002 | Aldrich et al. |
| 2002/0177897 A1 | 11/2002 | Michelson |
| 2003/0004576 A1 | 1/2003 | Thalgott |
| 2003/0040746 A1 | 2/2003 | Mitchell et al. |
| 2003/0040802 A1 | 2/2003 | Errico et al. |
| 2003/0176926 A1 | 9/2003 | Boehm, Jr. et al. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0230309 A1 | 11/2004 | Dimauro et al. |
| 2004/0254643 A1 | 12/2004 | Jackson |
| 2005/0027362 A1 | 2/2005 | Williams et al. |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | McLuen |
| 2006/0122701 A1 | 6/2006 | Kiester |
| 2006/0189999 A1 | 8/2006 | Zwirkoski |
| 2006/0241601 A1 | 10/2006 | Trautwein et al. |
| 2006/0241621 A1 | 10/2006 | Moskowitz et al. |
| 2006/0253201 A1 | 11/2006 | McLuen |
| 2006/0264938 A1 | 11/2006 | Zucherman et al. |
| 2006/0265077 A1 | 11/2006 | Zwirkoski |
| 2007/0072475 A1 | 3/2007 | Justin et al. |
| 2007/0142915 A1 | 6/2007 | Altarac et al. |
| 2007/0213739 A1 | 9/2007 | Michelson |
| 2007/0244485 A1 | 10/2007 | Greenhalgh et al. |
| 2007/0270968 A1 | 11/2007 | Baynham et al. |
| 2008/0114367 A1 | 5/2008 | Meyer |
| 2008/0114453 A1 | 5/2008 | Francis |
| 2008/0114456 A1 | 5/2008 | Dewey et al. |
| 2008/0119853 A1 | 5/2008 | Felt et al. |
| 2008/0119945 A1 | 5/2008 | Frigg |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0243251 A1 | 10/2008 | Stad et al. |
| 2008/0288077 A1 | 11/2008 | Reo et al. |
| 2008/0312741 A1 | 12/2008 | Lee et al. |
| 2009/0005872 A1 | 1/2009 | Moumene et al. |
| 2009/0062833 A1 | 3/2009 | Song |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198338 A1 | 8/2009 | Phan |
| 2009/0198339 A1 | 8/2009 | Kleiner et al. |
| 2009/0222099 A1 | 9/2009 | Liu et al. |
| 2009/0222100 A1 | 9/2009 | Cipoletti et al. |
| 2009/0228109 A1 | 9/2009 | Pointillant et al. |
| 2009/0312837 A1 | 12/2009 | Eisermann et al. |
| 2010/0082109 A1 | 4/2010 | Greenhalgh et al. |
| 2010/0103344 A1 | 4/2010 | Wang et al. |
| 2010/0179655 A1 | 7/2010 | Hansell et al. |
| 2010/0185291 A1 | 7/2010 | Jimenez et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234889 A1 | 9/2010 | Hess |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0029085 A1 | 2/2011 | Hynes et al. |
| 2011/0046682 A1 | 2/2011 | Stephan et al. |
| 2011/0054538 A1 | 3/2011 | Zehavi et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144753 A1 | 6/2011 | Marchek et al. |
| 2011/0144755 A1 | 6/2011 | Baynham et al. |
| 2011/0166654 A1 | 7/2011 | Gately |
| 2011/0172709 A1 | 7/2011 | Lyons et al. |
| 2011/0172716 A1 | 7/2011 | Glerum |
| 2011/0172774 A1 | 7/2011 | Varela |
| 2011/0178599 A1 | 7/2011 | Brett |
| 2011/0184468 A1 | 7/2011 | Metcalf et al. |
| 2011/0190817 A1 | 8/2011 | Thommen et al. |
| 2011/0196494 A1 | 8/2011 | Yedlicka et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0035730 A1 | 2/2012 | Spann |
| 2012/0046748 A1 | 2/2012 | Weiman |
| 2012/0059472 A1 | 3/2012 | Weiman |
| 2012/0059474 A1 | 3/2012 | Weiman |
| 2012/0059475 A1 | 3/2012 | Weiman |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0203347 A1 | 8/2012 | Glerum et al. |

(56) References Cited

U.S. PATENT DOCUMENTS

| | | |
|---|---|---|
| 2012/0221051 A1 | 8/2012 | Robinson |
| 2012/0226357 A1 | 9/2012 | Varela |
| 2012/0330422 A1 | 12/2012 | Weiman |
| 2013/0023993 A1 | 1/2013 | Weiman |
| 2013/0023994 A1 | 1/2013 | Glerum |
| 2013/0085572 A1 | 4/2013 | Glerum et al. |
| 2013/0103156 A1 | 4/2013 | Packer et al. |
| 2013/0116793 A1 | 5/2013 | Kloss |
| 2013/0144391 A1 | 6/2013 | Siegal et al. |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2014/0067071 A1 | 3/2014 | Weiman et al. |
| 2014/0148904 A1 | 5/2014 | Robinson |
| 2014/0163683 A1 | 6/2014 | Seifert et al. |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0249632 A1* | 9/2014 | Weiman ............... A61F 2/447 623/17.16 |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |
| 2014/0343678 A1 | 11/2014 | Suddaby et al. |
| 2015/0012097 A1 | 1/2015 | Ibarra et al. |
| 2015/0066145 A1 | 3/2015 | Rogers et al. |
| 2015/0100126 A1* | 4/2015 | Melkent ............. A61B 17/7059 623/17.16 |
| 2015/0100128 A1 | 4/2015 | Glerum et al. |
| 2015/0100130 A1 | 4/2015 | Perrow |
| 2015/0112438 A1 | 4/2015 | McLean |
| 2015/0173917 A1 | 6/2015 | Radcliffe et al. |
| 2015/0230931 A1 | 8/2015 | Greenhalgh |
| 2015/0351928 A1 | 12/2015 | Butler et al. |
| 2015/0374507 A1 | 12/2015 | Wolters et al. |
| 2016/0051377 A1 | 2/2016 | Weiman et al. |
| 2016/0089247 A1 | 3/2016 | Nichols et al. |
| 2016/0095718 A1 | 4/2016 | Weiman et al. |
| 2016/0113776 A1 | 4/2016 | Capote |
| 2016/0120660 A1 | 5/2016 | Melkent et al. |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 | 12/2016 | Faulhaber |
| 2016/0374826 A1 | 12/2016 | Palmatier et al. |
| 2017/0014239 A1* | 1/2017 | Seifert ............... A61F 2/447 |
| 2017/0014244 A1 | 1/2017 | Seifert et al. |
| 2017/0056197 A1 | 3/2017 | Weiman et al. |
| 2017/0100255 A1 | 4/2017 | Hleihil et al. |
| 2017/0172756 A1 | 6/2017 | Faulhaber |
| 2017/0216036 A1 | 8/2017 | Cordaro |
| 2017/0224504 A1 | 8/2017 | Butler et al. |
| 2017/0224505 A1 | 8/2017 | Butler et al. |
| 2017/0246006 A1 | 8/2017 | Carnes et al. |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1 | 11/2017 | Robinson |
| 2017/0333199 A1 | 11/2017 | Sharifi-Mehr et al. |
| 2017/0333200 A1 | 11/2017 | Arnin |
| 2017/0348116 A1 | 12/2017 | Weiman |
| 2017/0367842 A1 | 12/2017 | Predick et al. |
| 2018/0000609 A1 | 1/2018 | Hessler et al. |
| 2018/0014947 A1 | 1/2018 | Baynham |
| 2018/0042732 A1 | 2/2018 | Seifert et al. |
| 2018/0049885 A1 | 2/2018 | Weiman et al. |
| 2018/0055652 A1 | 3/2018 | Davenport et al. |
| 2018/0185163 A1 | 7/2018 | Weiman et al. |
| 2018/0243107 A1* | 8/2018 | Foley ............... A61F 2/4425 |
| 2018/0256359 A1 | 9/2018 | Greenhalgh |
| 2018/0289505 A1* | 10/2018 | Foley ............... A61F 2/4465 |
| 2018/0296361 A1 | 10/2018 | Butler et al. |
| 2018/0303621 A1 | 10/2018 | Brotman et al. |
| 2018/0318101 A1 | 11/2018 | Engstrom |
| 2018/0325693 A1* | 11/2018 | Weiman ............... A61F 2/4465 |
| 2018/0360616 A1 | 12/2018 | Luu |
| 2019/0021871 A1 | 1/2019 | Baynham |
| 2019/0133779 A1 | 5/2019 | McLaughlin et al. |
| 2019/0133784 A1 | 5/2019 | Gunn et al. |
| 2019/0201210 A1 | 7/2019 | Besaw et al. |
| 2019/0254836 A1 | 8/2019 | Cowan et al. |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1 | 10/2019 | Faulhaber |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0129307 A1 | 4/2020 | Hunziker et al. |
| 2020/0360153 A1 | 11/2020 | Weiman et al. |
| 2021/0015627 A1* | 1/2021 | Weiman ............... A61F 2/4455 |
| 2021/0030560 A1* | 2/2021 | Abu-Mulaweh ...... A61F 2/4455 |
| 2021/0045891 A1 | 2/2021 | Rogers et al. |
| 2021/0045892 A1 | 2/2021 | Rogers et al. |
| 2021/0113349 A1 | 4/2021 | Weiman et al. |
| 2021/0077274 A1 | 5/2021 | Jang |
| 2021/0137699 A1 | 5/2021 | Jang et al. |
| 2021/0259849 A1 | 8/2021 | Robinson et al. |
| 2021/0322181 A1 | 10/2021 | Predick |
| 2021/0353428 A1 | 11/2021 | Predick et al. |
| 2022/0133495 A1 | 5/2022 | Glerum et al. |
| 2022/0304823 A1 | 9/2022 | Melchor |
| 2022/0387184 A1 | 12/2022 | Josse et al. |

FOREIGN PATENT DOCUMENTS

| | | |
|---|---|---|
| DE | 94 07 806 U1 | 7/1994 |
| DE | 20314708 U1 | 11/2003 |
| DE | 10 2020 200 882 A1 | 7/2020 |
| EP | 0 880 950 A1 | 12/1998 |
| EP | 1 925 272 A1 | 5/2008 |
| EP | 2 777 633 A2 | 9/2014 |
| EP | 3 031 424 A1 | 6/2016 |
| EP | 3 245 982 | 11/2017 |
| EP | 3 366 263 A1 | 8/2018 |
| EP | 3 479 799 A1 | 5/2019 |
| EP | 3 769 725 A1 | 1/2021 |
| FR | 2717068 A1 | 4/1996 |
| FR | 2727003 B1 | 4/1997 |
| FR | 2894130 A1 | 6/2007 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-00/44319 A1 | 8/2000 |
| WO | WO-02/44319 A1 | 6/2002 |
| WO | WO-2004/052245 | 6/2004 |
| WO | WO-2005/009299 A1 | 2/2005 |
| WO | WO-2006/102485 | 9/2006 |
| WO | WO-2006/105437 A2 | 10/2006 |
| WO | WO-2009/124269 A1 | 10/2009 |
| WO | WO-2010/148112 | 12/2010 |
| WO | WO-2012/121726 A1 | 9/2012 |
| WO | WO-2014/134590 A1 | 9/2014 |
| WO | WO-2014/165319 A1 | 10/2014 |
| WO | WO-2015/009793 A1 | 1/2015 |
| WO | WO-2015/063721 A1 | 5/2015 |
| WO | WO-2015/085111 A1 | 6/2015 |
| WO | WO-2016/051095 A1 | 4/2016 |
| WO | WO-2016/077610 A1 | 5/2016 |
| WO | WO-2016/127139 A1 | 8/2016 |
| WO | WO-2017/027277 A1 | 2/2017 |
| WO | WO-2017/027873 A1 | 2/2017 |
| WO | WO-2017/066463 A1 | 4/2017 |
| WO | WO-2017/106614 A1 | 6/2017 |
| WO | WO-2018/049227 A1 | 3/2018 |
| WO | WO-2018/200507 A1 | 11/2018 |

(56) References Cited

FOREIGN PATENT DOCUMENTS

| WO | WO-2018/200530 A1 | 11/2018 |
|----|-------------------|---------|
| WO | WO-2019/014139 A1 | 1/2019 |
| WO | WO2019/0014139 A1 | 1/2019 |
| WO | WO-2019/126213 A1 | 6/2019 |
| WO | WO-2019/241687 A1 | 12/2019 |
| WO | WO-2021/030645 A1 | 2/2021 |

OTHER PUBLICATIONS

Extended European Search Report for European Application No. 14159101.6, dated Jun. 18, 2014, 6 pages.
Extended European Search Report for European Application No. 16169890.7, dated Oct. 21, 2016, 7 pages.
Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.
Foreign Search Report on PCT PCT/US2019/037275 dtd Sep. 24, 2019.
International Preliminary Report on Patentability for International Application No. PCT/US06/12060 mailing date Sep. 30, 2007, 3 pages.
International Search Report and Written Opinion for International Application No. PCT/US06/12060, mailing date Apr. 5, 2007, 3 pages.
International Search Report and Written Opinion for International Application No. PCT/US2006/012060, mail date Apr. 5, 2007, 4 pages.
International Search Report and Written Opinion for International Application No. PCT/US2012/057324, mail date Dec. 20, 2012, 10 pages.
International Search Report and Written Opinion in PCT PCT/US2021/030261 dated Aug. 31, 2021 (18 pages).
International Search Report and Written Opinion in PCT/US2021/031596 dated Sep. 28, 2021 (12 pages).
International Search Report and Written Opinion in PCT/US2021/033832 dated Sep. 17, 2021.
International Search Report and Written Opinion on PCT/US2020/036809 dtd Sep. 14, 2020, 12 pages.
International Search Report and Written Opinion received for Life Spine, Inc. for PCT app. PCT/US2021/026606 dated Jul. 15, 2021, 20 pages.
International Search Report and Written Opinion received for Life Spine, Inc., for PCT app. No. PCT/US2021026610 dated Jul. 20, 2021, 18 pages.
International Search Report for International Application No. PCT/US2018/029120, mail date Jun. 28, 2018, 17 pages.
International Search Report for International Application No. PCT/US2018/029149, mail date Jun. 25, 2018, 13 pages.
International Search Report on PCT/US2020/037020, Sep. 29, 2020, 20 pages.
Schizas, C., "Spinal Fusion: Techniques Results and Limitations." European Cells and Materials. 2005, vol. 10, Suppl. 3, p. 1.
Search Report for International Application No. PCT/US2018/041306, mail date Sep. 28, 2018, 12 pages.
"MectaLIF Oblique & Posterior Intervertebral Body Fusion Device." Brochure. 2004, Medacta International, San Pietro, Switzerland.
"Webster's II New College Dictionary." Excerpts. 2005, Houghton Mifflin Co., p. 992.
"Wedge." Encyclopedia Brittanica. Aug. 14, 2008. britannica.com/print/article/638734.
International Search Report and Written Opinion in PCT/US2022/053230 dated May 3, 2023 (18 pages).
Kambin, P., et al., "Arthroscopic Discectomy of the Lumbar Spine." Clinical Orthopaedics and Related Research. Apr. 1997, No. 337, pp. 49-57.
Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.
Kim, Y, et al., "Clinical Applications of the Tubular Retractor on Spinal Disorders." Journal of Korean Neurosurgery, Nov. 2007, No. 42, pp. 244-250.
Moore, J., et al., "Mechanics Map—Wedges." Aug. 20, 2022, mechanicsmap.psu.edu/websites/7_friction/7-3_wedges/wedges.
Peltier, L. "Orthopedics: A History and Iconography" 1993, Norman Publishing, San Francisco, CA.
Sasso, R., et al., "Anterior Lumbar Interbody Fusion." Surgical Management of Low Back Pain. 2009, Chapter 10, pp. 87-95.
Tsuang, Y., et al., "Comparison of cage application modality in posterior lumbar interbody fusion with posterior instrumentation—A finite element study." Medical Engineering & Physics 31. 2009, pp. 565-570.
Virk, S., et al. "History of Spinal Fusion: Where We Came from and Where We Are Going." Current Concepts in Spinal Fusion. HSS Journal, 2020, No. 16, pp. 137-142.
Xiao, Y, et al., "Unilateral Transforaminal Lumbar Interbody Fusion: a Review of the Technique, Indications and Graft Materials." The Journal of International Medical Research. 2009, No. 37, pp. 908-917.
International Search Report and Written Opinion in PCT/US2023/021528 dated Aug. 24, 2023 (17 pages).

* cited by examiner

STEERABLE IMPLANT ASSEMBLY

CROSS-REFERENCE TO RELATED PATENT APPLICATIONS

This application is a continuation-in-part of U.S. patent application Ser. No. 16/875,465, filed on May 15, 2020, the entire disclosure of which is hereby incorporated by reference herein.

BACKGROUND

The present disclosure relates to expandable implants and devices, including spinal interbody and intravertebral body devices, and vertebral interbody and intravertebral devices that are expandable after spinal placement thereof.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problems. With intravertebral devices, one or more spinal bodies are placed within a vertebra. Spinal devices, such as fusion cages and/or the like, are inserted into a spinal space either anteriorly, posteriorly, laterally or posteriolaterally.

SUMMARY

One embodiment relates to a steerable expandable implant including a base member, an adjustable member coupled to the base member, the adjustable member movable between a collapsed position and an expanded position, a pivot member rotatably received by the base member and configured to receive a tool such that the tool and the pivot member are rotatable relative to the base member between a first position and a second position, wherein the pivot member is translationally fixed relative to the base member, and a first control member received by the base member, wherein manipulation of the first control member causes the adjustable member to move between the collapsed position and the expanded position.

In some embodiments, the steerable expandable implant further includes a second control member coupled to the first control member, wherein the pivot member includes a bore extending therethrough and defining a first axis, wherein a second axis of the second control member is aligned with the first axis of the pivot member when the pivot member is in the first position. In some embodiments, the first axis of the pivot member at the second position is at an angle to the second axis of the second control member when the pivot member is in the second position. In some embodiments, the base member further includes an alignment portion configured to receive an alignment member of the tool to position the tool relative to the base member in the first and second positions, and wherein the base member includes an alignment protrusion configured to slidably engage an alignment track of the second control member and align the second control member to the base member. In some embodiments, an axis of the tool is parallel to an axis of the steerable expandable implant when the pivot member is in the first position. In some embodiments, a top surface of a first adjustable and a bottom surface of the base member define a height of the steerable expandable implant and are configured to engage adjacent portions of bone. In some embodiments, translation of the first control member changes a height of the steerable expandable implant. In some embodiments, a top surface of a first adjustable member and a bottom surface of a second adjustable member define a height of the steerable expandable implant and are configured to engage adjacent portions of bone, and wherein translation of the first control member changes a height of the steerable expandable implant.

Another embodiment relates to a steerable expandable implant including a base member, one or more adjustable members coupled to the base member, the adjustable member movable between a collapsed position and an expanded position, a first control member translationally coupled and pivotally fixed relative to the base member, and a second control member slidably coupled to the first control member and the adjustable member, wherein an axis of the second control member is offset relative to an axis of the first control member, wherein manipulation of the first control member causes at least one of the adjustable member to move between the collapsed position and the expanded position.

In some embodiments, the steerable expandable implant further comprises an adjustment member threadingly coupled to the first control member, wherein rotation of the adjustment member causes movement of the first control member. In some embodiments, the steerable expandable implant further comprises a pivot member pivotally received by the base member and configured to receive a tool such that the tool and the pivot member are pivotable relative to the base member. In some embodiments, the base member further includes an alignment portion configured to receive an alignment member of the tool to align the tool to the base member. In some embodiments, a top surface of a first adjustable member and one of a bottom surface of the base member or a bottom surface of a second adjustable member define a height of the steerable expandable implant. In some embodiments, the first control member includes a first guide extending into the base member and configured to limit a range of motion of the first control member, and wherein the second control member includes a second guide extending into the base member and configured to limit a range of motion of the second control member. In some embodiments, the second control member includes a control portion configured to slidably align the second control member with the base member.

Another embodiment relates to a method of positioning a spinal implant including coupling a tool to an implant, manipulating the tool to move the implant to a desired location, rotating the tool relative to a base member of the implant, coupling a control member of the tool to a first control member of the implant, and operating the control member of the tool to change a height of the implant.

In some embodiments, rotating the tool relative to the base member includes rotating the tool until the control member of the tool is axially aligned with the first control member. In some embodiments, operating the control member includes rotating the control member of the tool to cause translation of the first control member. In some embodiments, translation of the first control member causes translation of a second control member slidably coupled to an adjustable member of the implant. In some embodiments, the second control member includes at least one control portion slideably coupled to the adjustable member and configured to cause the adjustable member to move relative to the base member responsive to translation of the second control member.

Another embodiment relates to a steerable expandable implant. The steerable expandable implant includes a lower support member configured to engage a first portion of bone, and an upper support member coupled to the lower support member and configured to engage a second portion of bone, the upper support member movable relative to the lower support member between a collapsed position and an expanded position. The steerable expandable implant also includes a first control member coupled to the lower support member, where manipulation of the first control member causes the lower support member to move relative to the upper support member between the collapsed position and the expanded position. The steerable expandable implant further includes a pivot member configured to receive a tool such that the tool and the pivot member are rotatable relative to the lower support member between a first position and a second position, where the pivot member includes an aperture and where an axis of the aperture is angularly offset from an axis of the first control member in the first position and the axis of the aperture is angularly aligned with the axis of the first control member in the second position.

Another embodiment relates to a steerable expandable implant. The steerable expandable implant includes a lower support member configured to engage a first portion of bone, and an upper support member coupled to the lower support member and configured to engage a second portion of bone, the upper support member movable relative to the lower support member between a collapsed position and an expanded position. The implant also includes a second control member coupled to the lower support member, where manipulation of a first control member causes the second control member to move relative to the first control member, and the lower support member to move relative to the upper support member between the collapsed position and the expanded position. The implant further includes a pivot member configured to receive a tool such that the tool and the pivot member are rotatable relative to the lower support member between a first position and a second position, and the pivot member including an aperture and where an axis of the aperture is angularly aligned with an axis of the second control member in the first position and the axis of the aperture is angularly offset from the axis of the second control member in the second position.

Another embodiment relates to a steerable expandable implant. The steerable expandable implant includes a lower support member configured to engage a first portion of bone, and an upper support member coupled to the lower support member and configured to engage a second portion of bone, the upper support member movable relative to the lower support member between a collapsed position and an expanded position. The steerable expandable implant also includes a first control member coupled to the lower support member, where manipulation of the first control member causes the lower support member to move relative to the upper support member between the collapsed position and the expanded position, and a second control member slidably coupled to the first control member, where an axis of the second control member is offset relative to an axis of the first control member. The steerable expandable implant further includes a pivot member configured to receive a tool such that the tool and the pivot member are rotatable relative to the lower support member between a first position and a second position, the pivot member including an aperture and where an axis of the aperture is angularly offset from an axis of the first control member in the first position and the axis of the aperture is angularly aligned with the axis of the first control member in the second position.

BRIEF DESCRIPTION

The foregoing and other features of the present invention will become more apparent to one skilled in the art upon also reading the following description of embodiments with reference to the accompanying drawings.

Figure 1:
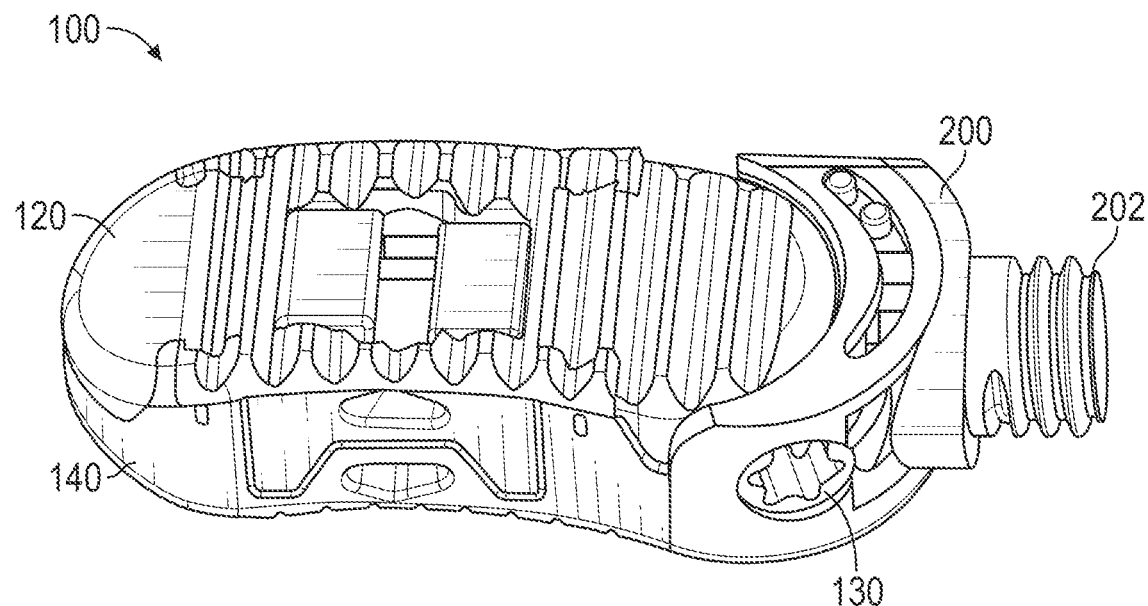
FIG. 1 is a perspective view of a steerable expandable implant in a first configuration, according to one embodiment.
Figure 2:
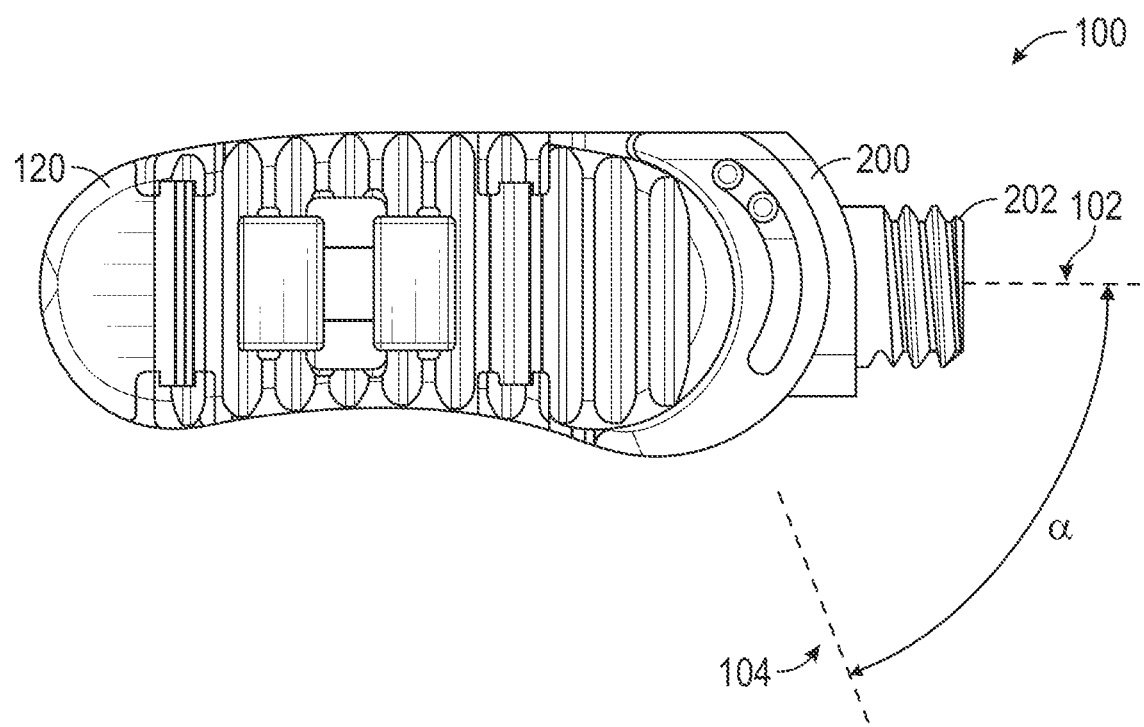
FIG. 2 is a top view of the steerable expandable implant of FIG. 1, according to one embodiment.
Figure 3:
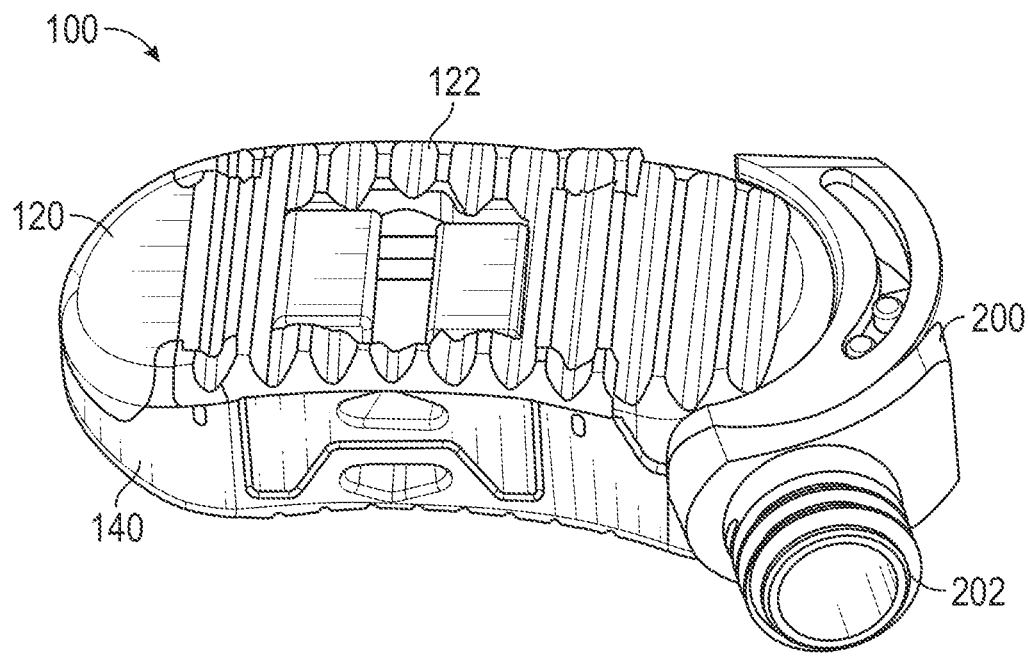
FIG. 3 is a perspective view of the steerable expandable implant of FIG. 1 in a second configuration, according to one embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

The present disclosure relates to steerable and expandable and/or dynamic implants, including, but not limited to, interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (steerable and expandable/retractable) interbody/intravertebral body devices that are usable in a spinal column or other areas of a human.

Spinal interbody and intravertebral devices may be difficult to position. That is, a compact orientation, conducive to insertion, may be inconvenient to maneuver into a final position. Such spinal interbody and intravertebral devices lack the ability to change an orientation once inserted. This poses various problems with their use and/or implantation. Particularly, statically oriented spinal devices require complex positioning instruments or techniques to properly position the device and bridge the gap between adjacent vertebrae. These instruments and techniques do not lend themselves to microsurgery, arthroscopic surgery or the like.

Expandable interbody devices allow the device to be initially smaller than traditional non-expandable (static) interbody devices such that expandable interbody devices may be more easily inserted or implanted into the vertebral space. Moreover, expandable devices allow the surgeon to set the amount of expansion necessary for the particular patient rather than the static device dictating the spacing.

Various embodiments disclosed herein are directed to steerable expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to FIG. 1-7, steerable expandable implant 100 is shown, according to an exemplary embodiment. Implant 100 is usable, for example, between and/or within vertebral bodies of the spine, and may share many of the features of the other inter/intra-body implants discussed elsewhere herein. It should be understood that implant 100 may, in some embodiments, be usable in other portions of the body in addition to the spine, and all such applications are to be understood to be within the scope of the present disclosure.

Implant 100 may be inserted into a patient while in a first orientation. Once inserted, an appropriate tool may be used to engage a portion of the implant 100 to reorient the implant 100 into a second orientation. Implant 100 may be positioned within a desired space (e.g., between adjacent portions of bone) while in a first, collapsed position. An appropriate tool may be used to engage a portion of implant 100 to manipulate implant 100 into a desired position. Once in a desired position, the same or a subsequent tool may be utilized to engage a portion of implant 100 to expand implant 100 to a desired degree of expansion. It should be understood that based on a particular application, implant 100 may be utilized in a fully collapsed position, a fully expanded position, or any intermediate position therebetween. Once implant 100 is properly positioned and expanded to a desired height, bone graft material may be delivered by way of an access aperture and placed into a central cavity of implant 100. The various apertures in and through implant 100 may facilitate the growth of bone material in and around implant 100 to further stabilize implant 100.

Referring again to FIGS. 1-7, according to an exemplary embodiment, implant 100 includes base member 140 and adjustable member 120 adjustably coupled to the base member 140. In various embodiments, base member 140 includes alignment channels 144 and 146 to receive alignment portions 124 and 126. Alignment channels 144 and 146 and alignment portions 124 and 126 may align adjustable member 120 to base member 140. For example, the alignment features (e.g., alignment channels 144 and 146 and/or alignment portions 124 and 126) may facilitate alignment of adjustable member 120 to base member 140 during expansion of implant 100. The alignment features may couple to one another and allow for vertical (e.g., up and down, expansive and contractive, etc.) movement of base member 140 and adjustable member 120. In some embodiments, the alignment features have a relatively close fit to facilitate alignment between adjustable member 120 and base member 140, while in other embodiments, the alignment features have a relatively loose fit to facilitate a desired angular offset between adjustable member 120 and base member 140. In some embodiments, alignment channels 144 and 146 and alignment portions 124 and 126 form a tongue and groove joint. In various embodiments, alignment portions 124 and 126 include pin slots 125 and 127. Pin slots 125 and 127 may receive a pin inserted into apertures 143 to limit expansion and/or contraction of adjustable member 120. For example, pin slots 125 and 127 may facilitate expansion of adjustable member 120 such that adjustable member 120 cannot decouple from base member 140. Base member 140 and adjustable member 120 are shown to include surface patterns 122 and 148 respectively. Surface patterns 122 and 148 are configured to promote bonding to an adjacent surface (e.g., a portion of bone) and prevent slippage of implant 100. In some embodiments, surface patterns 122 and 148 are patterned ridges.

Implant 100 includes control member 200 coupled to an end of base member 140 and usable to manipulate implant 100 into a location on the patient. Control member 200 may rotate about the end of base member 140 between a first position 102 (shown in FIG. 2) and a second position 104 (shown in FIG. 4). First position 102 may reduce the cross-sectional footprint of implant 100 for implantation, allowing for smaller opening incisions and less invasive surgery techniques. Second position 104 may facilitate positioning implant 100 to align with the intended implantation location, thereby allowing for less reorientation of implant 100 and a more straightforward implantation. Control member 200 may include manipulation connector 202 to connect a tool for manipulation of implant 100 during implantation. In some embodiments, manipulation connector 202 is a male screw thread to receive a female mating thread. Implant 100 may include first control shaft 130 received by base member 140. First control shaft 130 may be used to expand implant 100. For example, a user may use a tool to manipulate (e.g., rotate, etc.) first control shaft 130 thereby causing expansion of implant 100. In various embodiments, an axis of first control shaft 130 aligns with an axis of control member 200 in the second position 104. Control member 200 may include an opening to facilitate access to first control shaft 130 while control member 200 is in the second position 104.

Figure 7:
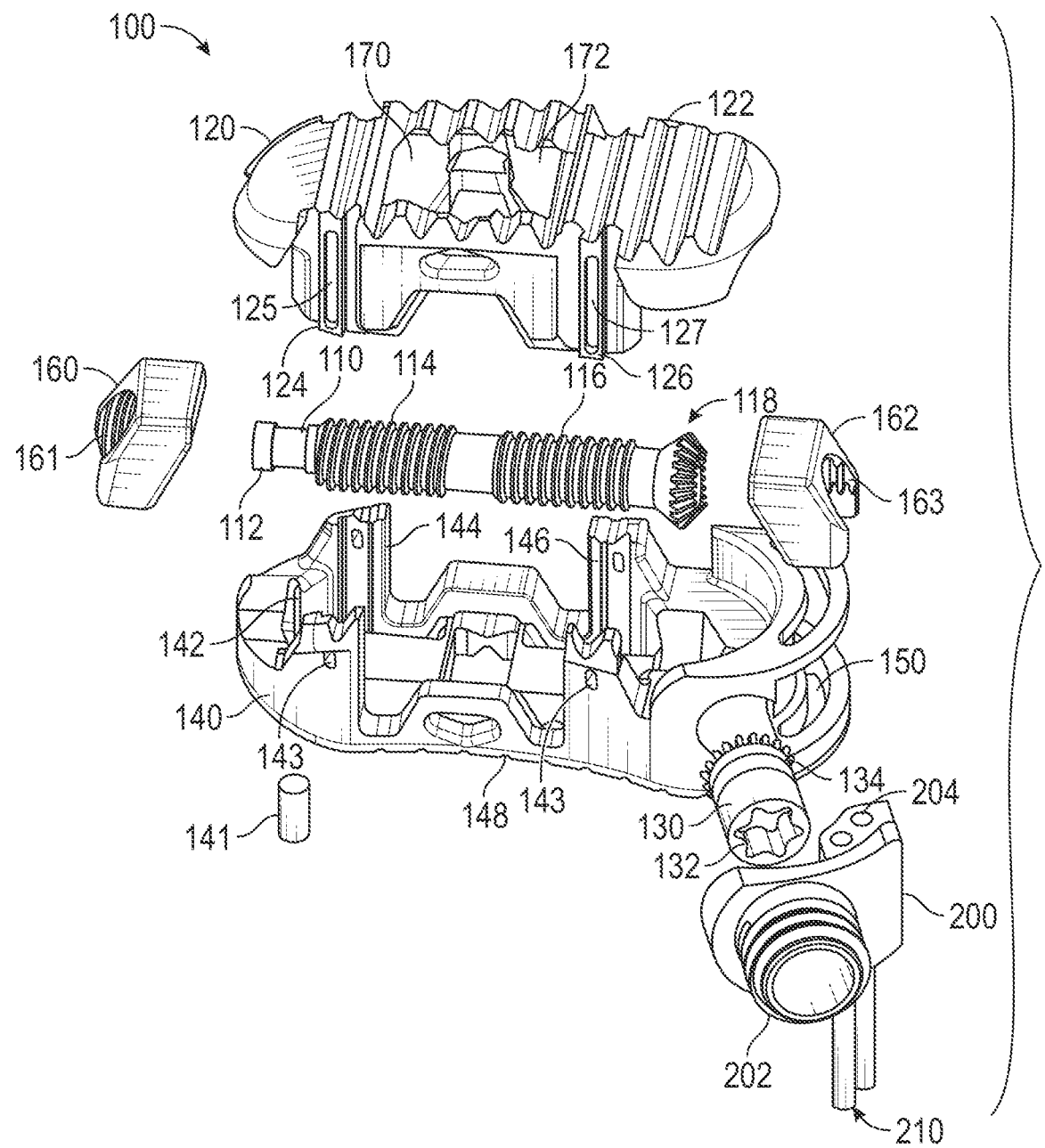
FIG. 7 is an exploded view of the steerable expandable implant of FIG. 1, according to one embodiment.
Figure 8:
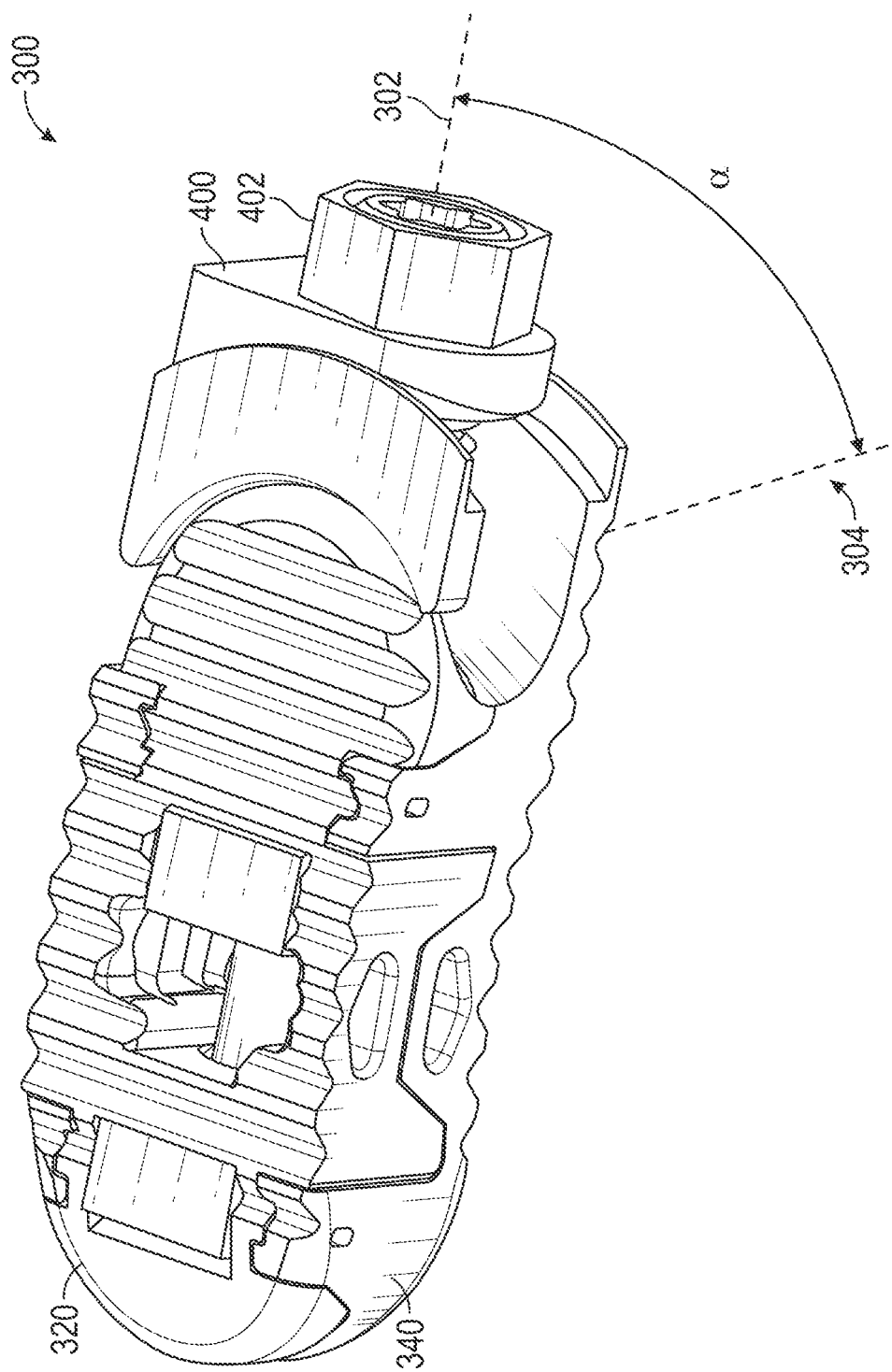
FIG. 8 is a perspective view of a steerable expandable implant in a first configuration, according to another embodiment.
Figure 9:
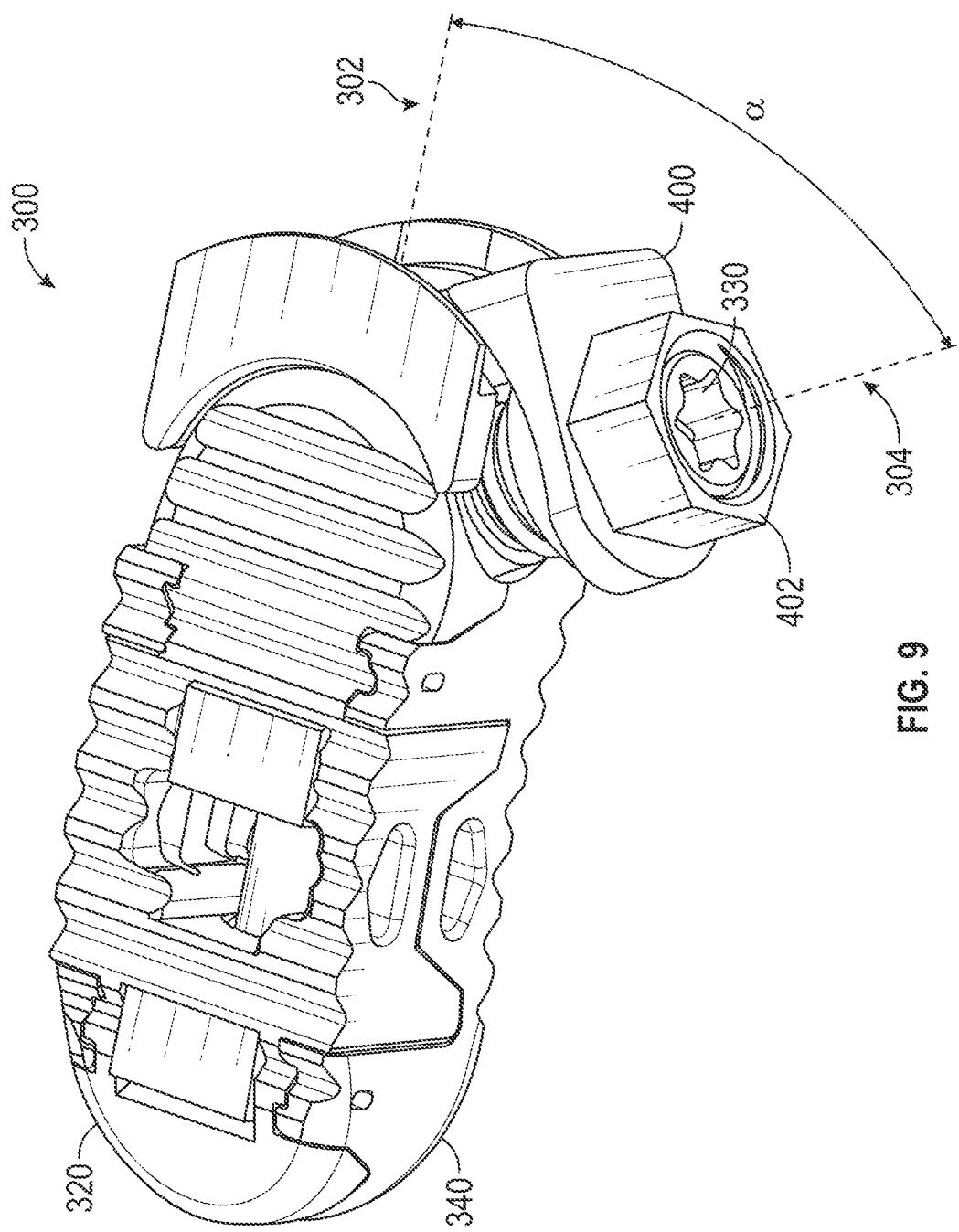
FIG. 9 is a perspective view of the steerable expandable implant of FIG. 8 in a second configuration, according to one embodiment.
Figure 10:
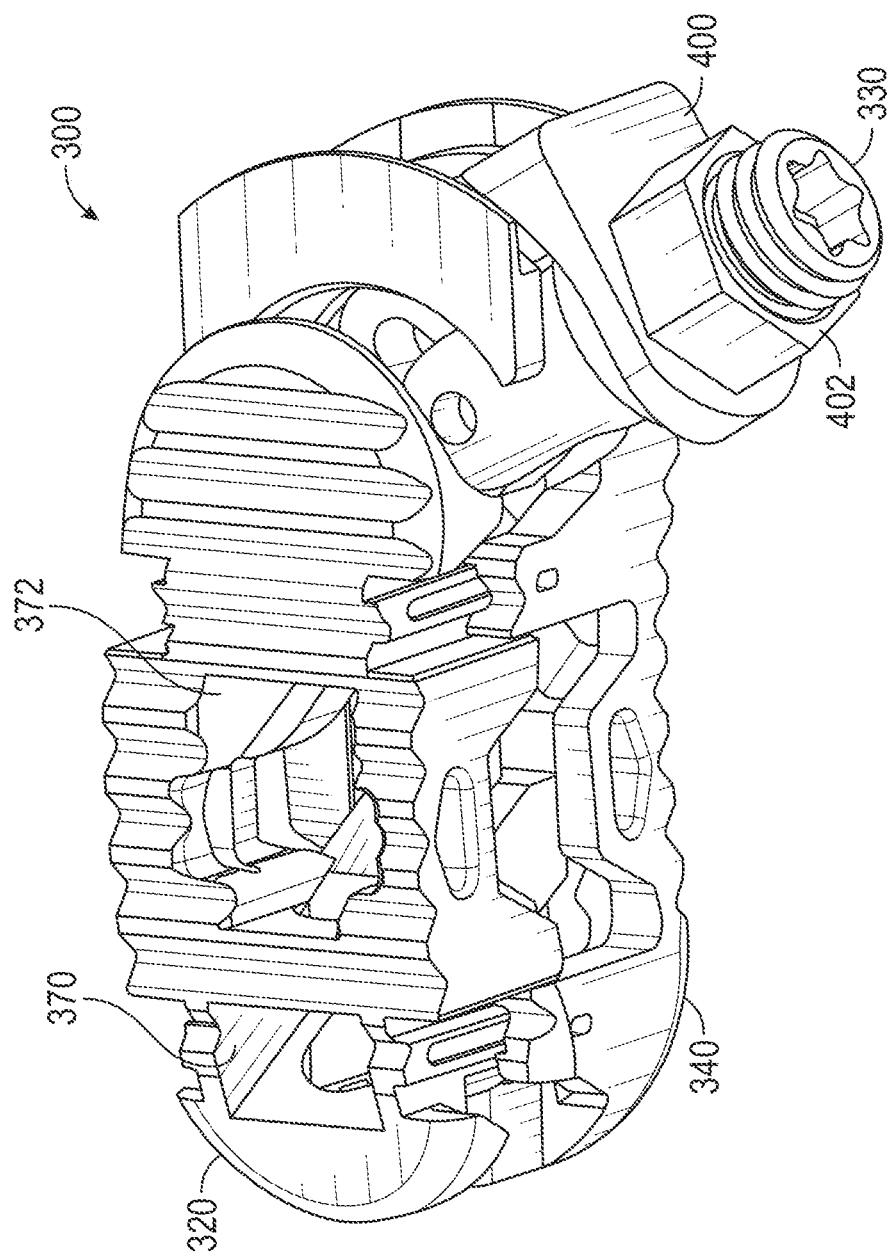
FIG. 10 is a perspective view of the steerable expandable implant of FIG. 8 in an expanded position, according to one embodiment.
Figure 11:
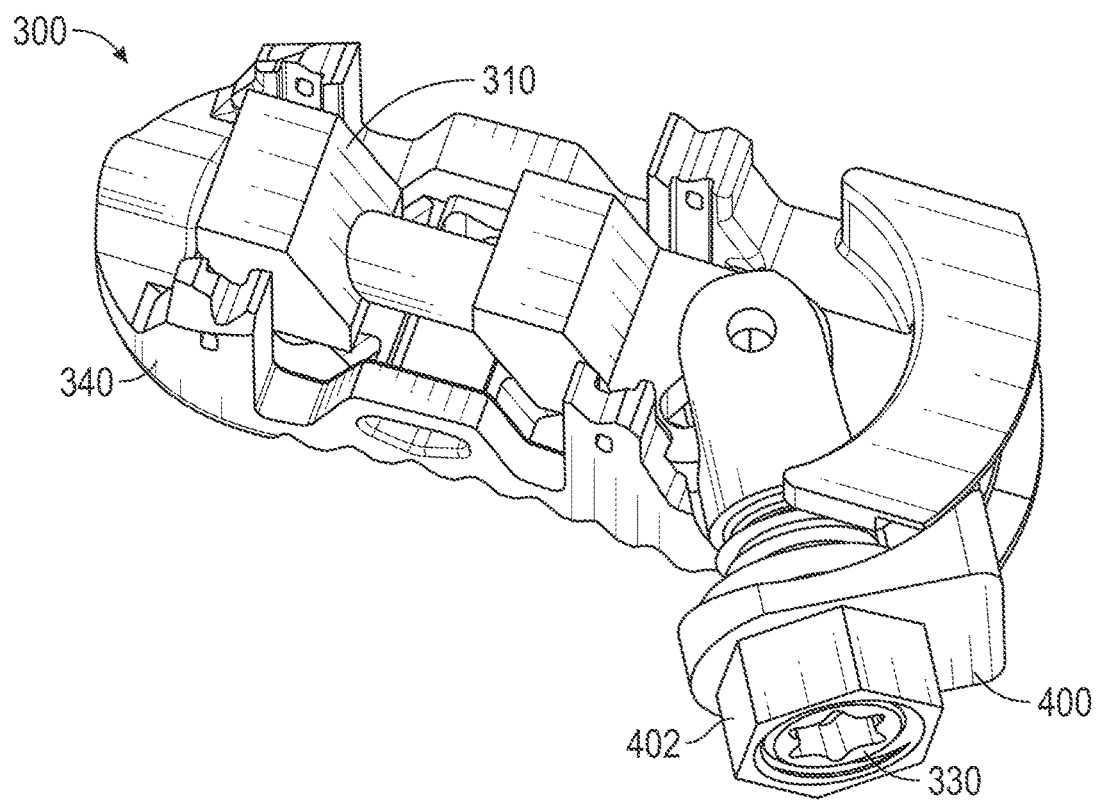
FIG. 11 is an internal view of a control shaft in a first position usable with the implants disclosed herein, according to one embodiment.
Figure 12:
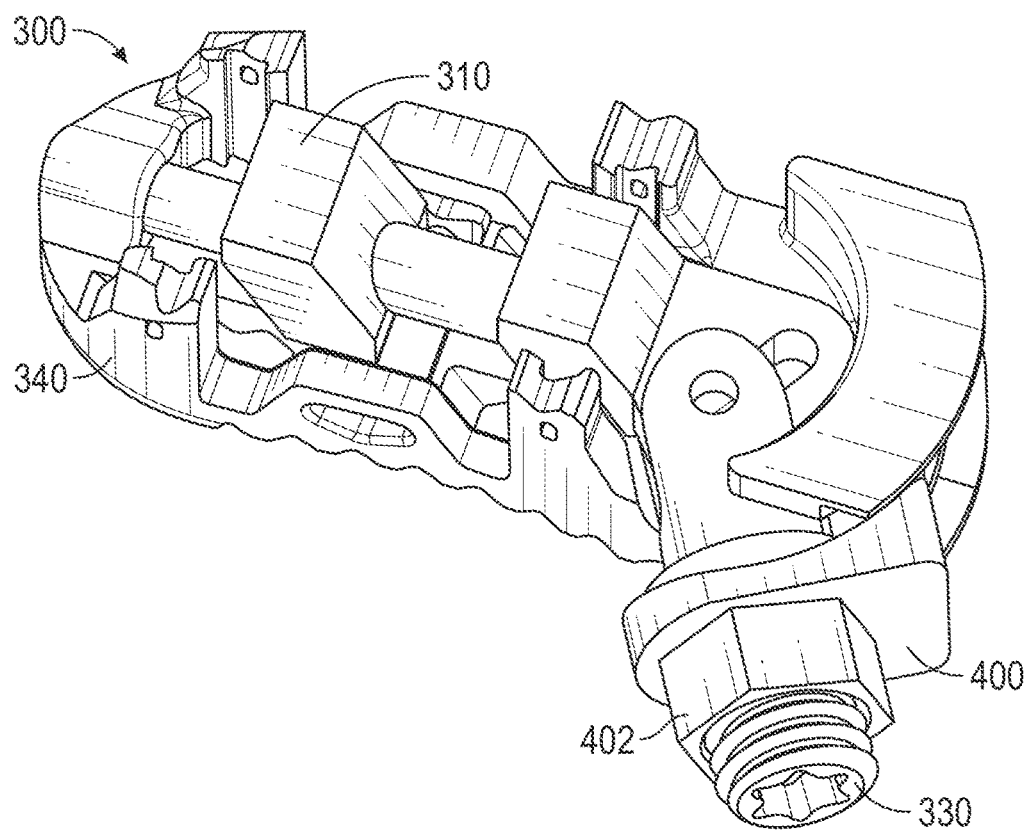
FIG. 12 is an internal view of a control shaft in a second position usable with the implants disclosed herein, according to one embodiment.

Referring now specifically to FIG. 7, first control shaft 130 may include or be coupled to connector 132 to receive a tool or other manipulation accessory. In some embodiments, connector 132 is a screw drive (e.g., Philips, Hex, Slot, etc.). In various embodiments, implant 100 includes a second control shaft 110 positioned between base member 140 and adjustable member 120. Second control shaft 110 may facilitate adjustment of the adjustable member 120 by transferring a force from a user to the adjustable member 120. In some embodiments, a user operates a different member (e.g., first control shaft 130) which transfers the operational force to second control shaft 110. First control shaft 130 may include engagement portion 134 configured to couple to contact 118 of second control shaft 110 and facilitate force transfer thereto. In some embodiments, engagement portion 134 is a geared portion to engage a corresponding geared portion of second control shaft 110. In various embodiments, second control shaft 110 and first control shaft 130 have different axes of rotation (i.e., are at an angle to one another). For example, first control shaft 130 may have a first axis that is conducive to manipulation by a user during implantation, while second control shaft 110 may have a second axis that facilitates adjustment of adjustable member 120. In some embodiments, second control shaft 110 includes one or more threaded portions 114 and 116. In some embodiments, implant 100 includes adjustment members 160 and 162 that may couple to second control shaft 110. Adjustment members 160 and 162 are shown to include threaded portions 161 and 163 respectively. Threaded portions 161 and 163 may correspond to the threaded portions 114 and 116 and couple thereto. Adjustment members 160 and 162 may translate along the axis of second control shaft 110. For example, rotation of second control shaft 110 may cause adjustment members 160 and 162 to move toward one another or away from one another. In some embodiments, threaded portion 114 and threaded portion 116 are threaded in opposite manners (e.g., left-handed and right-handed) such that, upon rotation of second control shaft 110, adjustment members 160 and 162 move in opposite directions along second control shaft 110. For example, second control shaft 110 may be configured such that rotation of second control shaft 110 in a first direction (e.g., clockwise) causes adjustment members 160 and 162 to move toward each other, and rotation of second control shaft 110 in a second direction (e.g., counter-clockwise) causes adjustment members 160 and 162 to move away from each other.

Second control shaft 110 is shown to include at one end connection 112 to be received by corresponding slot 142 in base member 140. Connection 112 may secure an end of second control shaft 110 and allow axial rotation of second control shaft 110. Pin 141 may be received within a vertical aperture of base member 140 and secure second control shaft 110. In various embodiments, pin 141 is received by a groove of second control shaft 110 thereby preventing horizontal translation of second control shaft 110.

Adjustable member 120 may include control channels 170 and 172 (see FIG. 7) to receive adjustment members 160 and 162 and cause an expansive or contractive translation based on movement of adjustment members 160 and 162. As adjustment members 160 and 162 translate along second control shaft 110, adjustable member 120 is moved upward or downward due to the angled shape of control channels 170 and 172. The rate of movement of adjustable member 120 can be adjusted by modifying the slope of control channels 170 and 172 relative to second control shaft 110. In some embodiments, the rate of movement of adjustable member 120 can be adjusted by modifying threaded portions 114 and 116 (e.g., lead, pitch, etc.) of second control shaft 110. Mechanisms of expandable implants are described in further detail in U.S. patent application Ser. No. 15/645,179 filed Jul. 10, 2017, the entirety of which is incorporated by reference herein.

Base member 140 may include guide channels 150. Guide channel 150 may receive pins 210 to couple control member 200 to base member 140. Pins 210 may be received by apertures 204 in control member 200 such that pins 210 extend beyond apertures 204 and are received in guide channels 150. Guide channels 150 may be configured to guide control member 200 in a path from the first position 102 (shown in FIG. 2) to the second position 104 (shown in FIG. 4). In some embodiments, control member 200, while in the second position 104, is configured to allow co-axial operation of first control shaft 130. For example, a tool attached to manipulation connector 202 may allow a user to operate first control shaft 130 to adjust adjustable member 120 while control member 200 is in the second position 104.

A non-limiting example of operation of control member 200 is as follows. A coaxial manipulation device may be attached to implant 100 via manipulation connector 202. Implant 100 may be inserted into the patient in the first position 102. In the first position 102, implant 100 is compact to allow for easy insertion. Once inside the patient, the user may move control member 200 from the first position 102 to the second position 104. In the second position 104, implant 100 is oriented to be aligned with an intended implant location on the patient, thereby reducing the amount of manual manipulation a user must perform to reorient implant 100 for alignment. Furthermore, in the second position 104, control member 200 is aligned with first control shaft 130 to facilitate operation of first control shaft 130 via the coaxial manipulation device. Once implant 100 is positioned in the intended location, the user may operate first control shaft 130, via the coaxial manipulation device, to adjust adjustable member 120 to a desired level of expansion to properly contact adjacent portions of bone.

Referring now to FIGS. 8-13, steerable expandable implant 300 is shown, according to an exemplary embodiment. Implant 300 may share many of the features of the other inter/intra-body implants discussed elsewhere herein. All such combinations of features are to be understood to be within the scope of the present disclosure. Implant 300 is generally similar to implant 100 in structure and function.

Implant 300 includes base member 340, adjustable member 320, and control member 400. Base member 340 and adjustable member 320 are configured to engage adjacent surfaces (e.g., portions of bone, etc.). In various embodiments, adjustable member 320 is coupled to base member 340 as described herein. Control member 400 is configured to facilitate manipulation of implant 300. For example, using a tool coupled to control member 400, a user may manipulate implant 300 into an implantation position. In various embodiments, base member 340, adjustable member 320, and/or control member 400 are the same or share features of base member 140, adjustable member 120, and/or control member 200.

In various embodiments, base member 340 includes alignment channels 344 and 346 to receive alignment portions 324 and 326. Alignment channels 344 and 346 and alignment portions 324 and 326 may align adjustable member 320 to base member 340. For example, the alignment features (e.g., alignment channels 344 and 346 and/or alignment portions 324 and 326) may facilitate alignment of adjustable member 320 to base member 340 during expansion of implant 300. The alignment features may couple to one another and allow for vertical (e.g., up and down, expansive and contractive, etc.) movement of base member 340 and adjustable member 320. In some embodiments, the alignment features have a relatively close fit to facilitate alignment between adjustable member 320 and base member 340, while in other embodiments, the alignment features have a relatively loose fit to facilitate a desired angular offset between adjustable member 320 and base member 340. In some embodiments, alignment channels 344 and 346 and alignment portions 324 and 326 form a tongue and groove joint. In various embodiments, alignment portions 324 and 326 include pin slots 325 and 327. Pin slots 325 and 327 may receive a pin inserted into apertures 343 to limit expansion and/or contraction of adjustable member 320. For example, pin slots 325 and 327 may facilitate expansion of adjustable member 320 such that adjustable member 320 cannot decouple from base member 340. Base member 340 and adjustable member 320 are shown to include surface patterns 322 and 348 respectively. Surface patterns 322 and 348 are configured to promote bonding to an adjacent surface (e.g., a portion of bone) and prevent slippage of implant 300. In some embodiments, surface patterns 322 and 348 are patterned ridges.

Implant 300 includes second control shaft 310 to affect an adjustment of adjustable member 320. Second control shaft 310 may be the same or share features of second control shaft 110. For example, second control shaft 310 may operate by a different principle than second control shaft 110. As a concrete example, second control shaft 310 may translate horizontally, while second control shaft 110 may rotate. Implant 300 includes first control shaft 330. First control shaft 330 may rotate about the end of base member 340 between a first position 302 (shown in FIG. 8) and a second position 304 (shown in FIG. 9).

Figure 13:
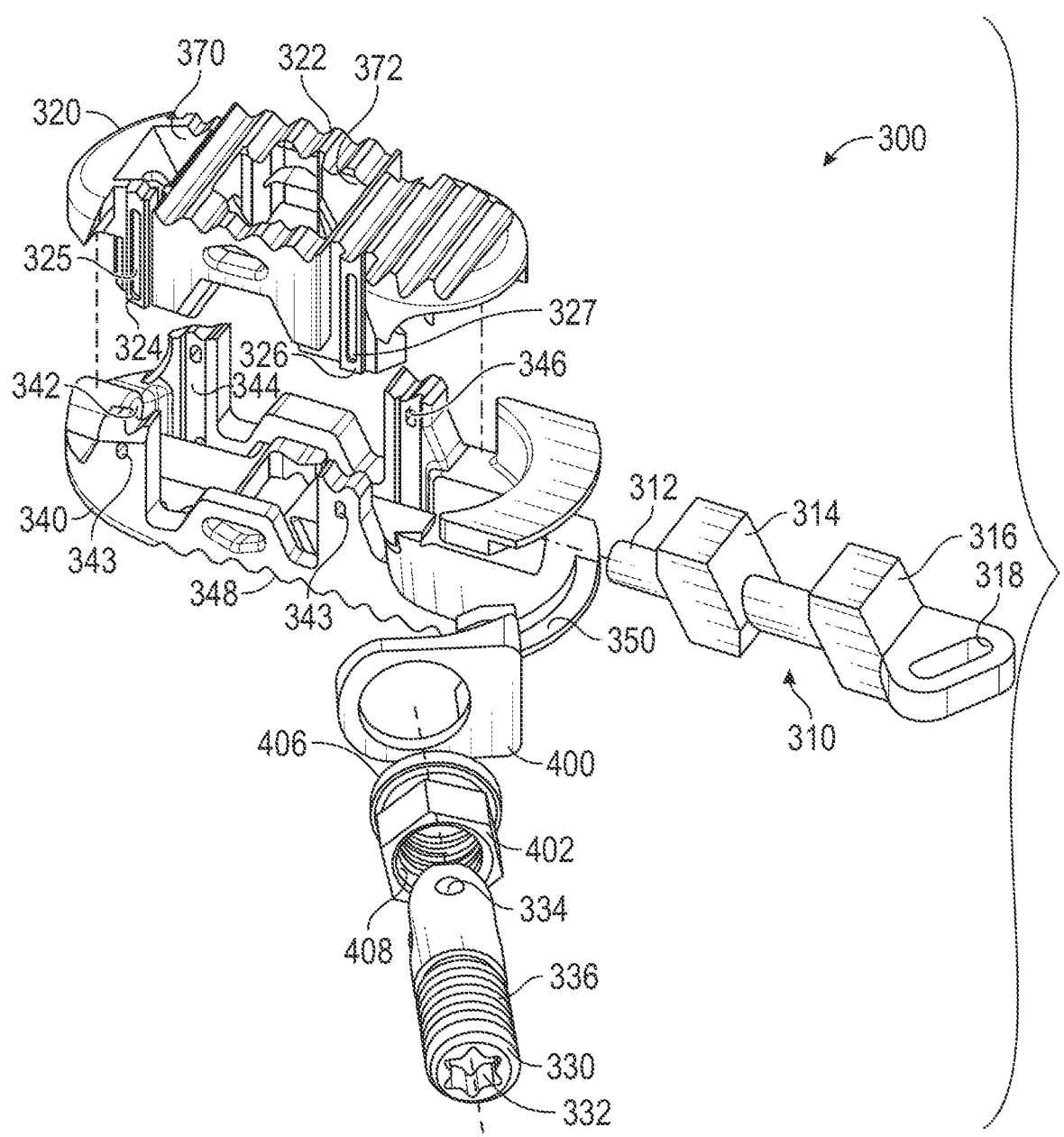
FIG. 13 is an exploded view of the steerable expandable implant of FIG. 8, according to one embodiment.

Referring now specifically to FIG. 13, first control shaft 330 may be received within control member 400 and manipulation connector 402. In various embodiments, first control shaft 330 includes engagement portion 336 to engage a corresponding engagement portion 408 of manipulation connector 402. In some embodiments, manipulation connector 402 is a nut and engagement portions 336 and 408 are screw threads. In some embodiments, a user may rotate manipulation connector 402 to affect a translation (e.g., inward or outward) of first control shaft 330. In some embodiments, first control shaft 330 includes connector 332 to facilitate translation of first control shaft 330. For example, a user may apply an axial force (e.g., inward or outward) to first control shaft 330 to facilitate rotation of manipulation connector 402 and/or translation of first control shaft 330. Connector 332 may be a screw drive (e.g., Philips, Hex, Slot, etc.).

Control member 400 may be configured to facilitate manipulation of implant 300 (e.g., to position implant 300 in an implantation location, etc.). In various embodiments, control member 400 may translate around an end of implant 300. In some embodiments, base member 340 includes guide channels 350 to facilitate translation of control member 400. In some embodiments, guide channels 350 are slotted grooves that receive alignment member 406 of manipulation connector 402. For example, alignment member 406 may be a protruded collar of manipulation connector 402 that rolls along guide channels 350. Additionally or alternatively, alignment member 406 may facilitate coupling manipulation connector 402 to control member 400. For example, alignment member 406 may include a groove that is received by control member 400 to rotatably couple manipulation connector 402 to control member 400. In some embodiments, rotation of manipulation connector 402, via the manipulation connector 402 or first control shaft 330, generates lateral movement across the end of implant 300 (e.g., along guide channels 350). For example, a user may rotate manipulation connector 402 counter-clockwise to move control member 400 between the first position 302 and the second position 304.

First control shaft 330 includes engagement portion 334 configured to facilitate coupling first control shaft 330 to second control shaft 310. In some embodiments, engagement portion 334 is an aperture to accept a link. For example, first control shaft 330 may connect to second control shaft 310 via a pin or other linking mechanism. Similarly, second control shaft 310 includes control channel 318 to receive a linking mechanism to link second control shaft 310 to first control shaft 330 and to guide translation (e.g., side to side) of second control shaft 310 in response to translation (e.g., inward or outward) of first control shaft 330.

Second control shaft 310 may include or be coupled to one or more interfaces 314 and 316 (e.g., control portions, etc.). In various embodiments, interfaces 314 and 316 are received within control channels 370 and 372 of adjustable member 320. As second control shaft 310 translates, adjustable member 320 is moved upward or downward due to the angled shape of control channels 370 and 372. The rate of movement of adjustable member 320 can be adjusted by modifying the slope of control channels 370 and 372 relative to second control shaft 310. Interfaces 314 and 316 may include angled portions that are configured to interface with control channels 370 and 372 to affect a vertical (e.g., up and down, expansive or contractive) movement of adjustable member 320 in response to a horizontal translation (e.g., side to side) of second control shaft 310. First control shaft 330 is configured to push or pull on second control shaft 310 via the linking mechanism between engagement portion 334 and control channel 318, thereby affecting a movement of adjustable member 320. Second control shaft 310 is shown to include contact 312 configured to couple to bore 342 of base member 340. Bore 342 may retain second control shaft 310 via contact 312 while allowing second control shaft 310 to slide (e.g., in and out of bore 342) freely.

A non-limiting example of operation of control member 400 is as follows. A coaxial manipulation device may be attached to implant 300 via manipulation connector 402. Implant 300 may be inserted into the patient in the first position 302. In the first position 302, implant 300 is compact to allow for easy insertion. Once inside the patient, the user may move control member 400 from the first position 302 to the second position 304. In the second position 304, implant 300 is oriented to be aligned with an intended implant location on the patient, thereby reducing the amount of manual manipulation a user must perform to reorient implant 300 for alignment. Once implant 300 is positioned in the intended location, the user may operate first control shaft 330, via the coaxial manipulation device, to adjust adjustable member 320 to a desired level of expansion to properly contact adjacent portions of bone.

Referring now to FIGS. 14-23, a steerable expandable implant 500 is shown according to an exemplary embodiment. Implant 500 may share many of the features of the other inter/intra-body implants discussed elsewhere herein. All such combinations of features are to be understood to be within the scope of the present disclosure. Implant 500 is generally similar to implant 300 in structure and function.

Referring now specifically to FIGS. 14-23, implant 500 includes base member 540 and adjustable member 520 adjustably coupled to base member 540. Base member 540 and adjustable member 520 are configured to engage adjacent surfaces (e.g., portions of bone, etc.). In various embodiments, adjustable member 520 is coupled to base member 540 as described herein. In various embodiments, base member 540 and/or adjustable member 520 are the same as or share features with base member 340 and/or adjustable member 320.

Figure 22:
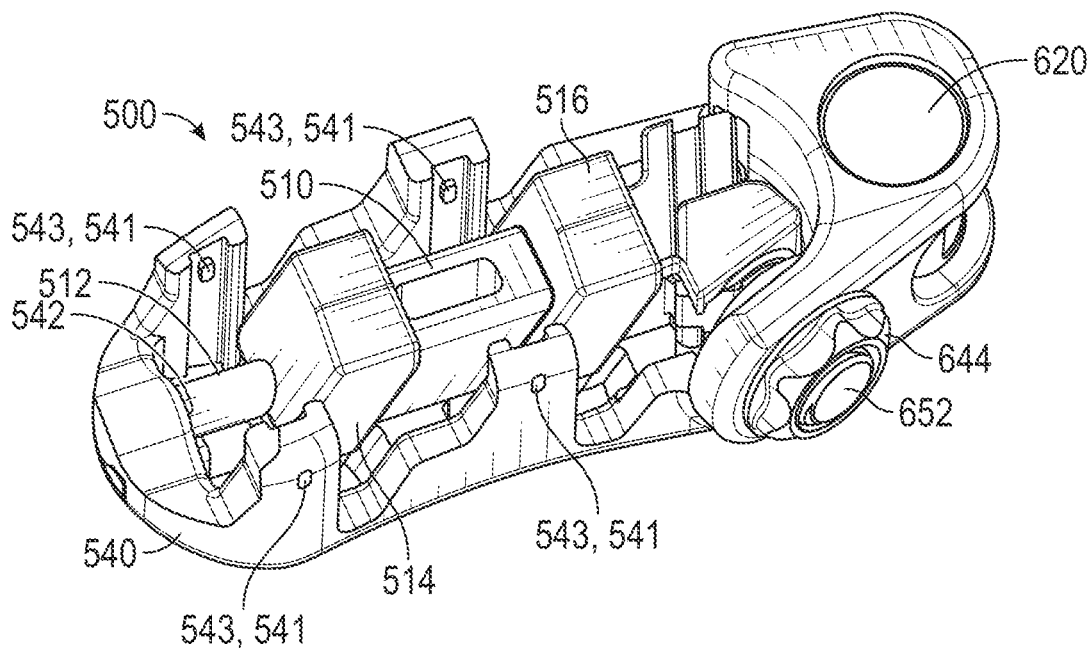
FIG. 22 is a perspective view of a control shaft in a first position usable with the implants disclosed herein, according to one embodiment.
Figure 23:
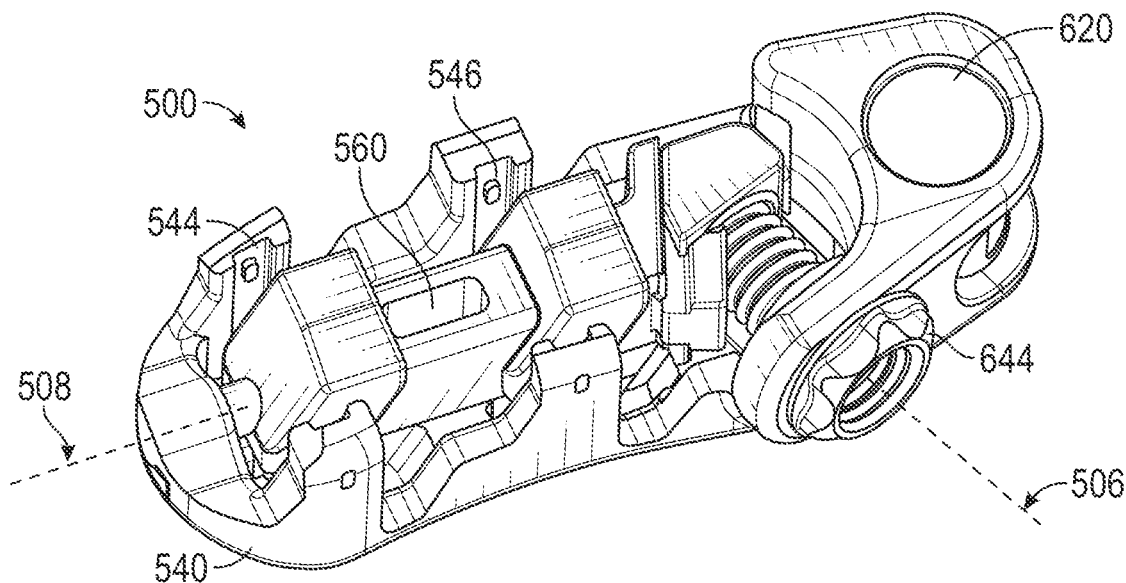
FIG. 23 is a perspective view of a control shaft in a second position usable with the implant disclosed herein, according to one embodiment.

In various embodiments, base member 540 includes alignment channels 544 and 546 to receive alignment portions 524 and 526. Alignment channels 544 and 546 and alignment portions 524 and 526 may align adjustable member 520 to base member 540. For example, the alignment features (e.g., alignment channels 544 and 546 and/or alignment portions 524 and 526) may facilitate alignment of adjustable member 520 to base member 540 during expansion of implant 500. The alignment features may couple to one another and allow for vertical (e.g., up and down, expansive and contractive, etc.) movement of base member 540 and adjustable member 520. In some embodiments, the alignment features have a relatively close fit to facilitate alignment between adjustable member 520 and base member 540, while in other embodiments, the alignment features have a relatively loose fit to facilitate a desired angular offset between adjustable member 520 and base member 540. In some embodiments, alignment channels 544 and 546 and alignment portions 524 and 526 form a tongue and groove joint. In various embodiments, alignment portions 524 and 526 include pin slots 525 and 527. As shown in FIG. 22, pin slots 525 and 527 may receive a pin 541 inserted into apertures 543 to limit expansion and/or contraction of adjustable member 520. For example, pin slots 525 and 527 may facilitate expansion of adjustable member 520 such that adjustable member 520 cannot decouple from base member 540. Base member 540 and adjustable member 520 are shown to include surface patterns 522 and 548 respectively. Surface patterns 522 and 548 are configured to promote bonding to an adjacent surface (e.g., a portion of bone) and prevent slippage of implant 500. In some embodiments, surface patterns 522 and 548 are patterned ridges.

Figure 15:
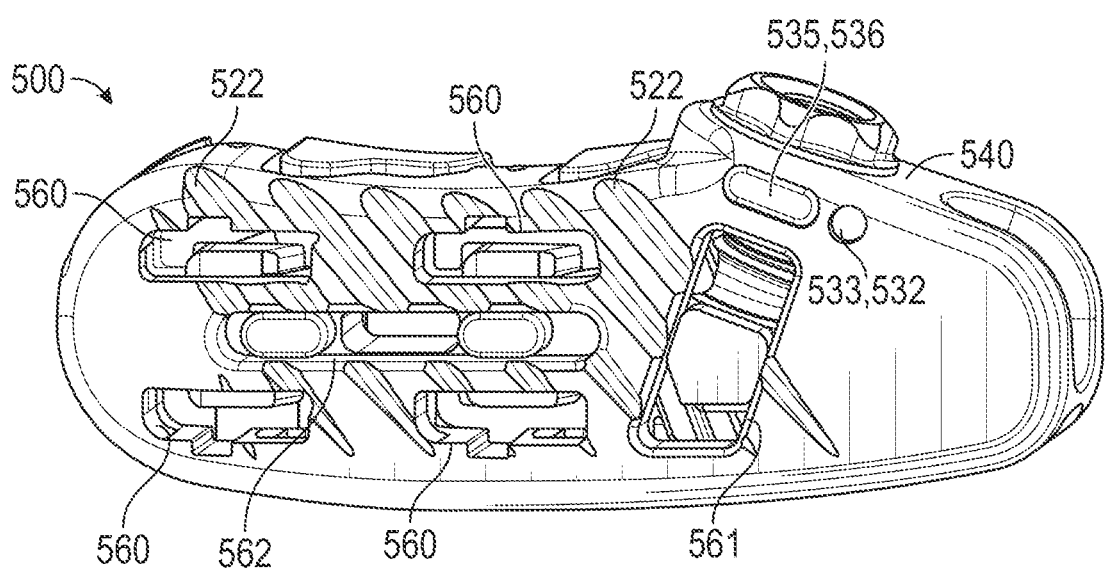
FIG. 15 is a bottom view of the steerable expandable implant of FIG. 15, according to one embodiment.

Implant 500 further includes second control member 510 (e.g., a control shaft, etc.). In various embodiments, second control member 510 translates along axis 508. In various embodiments, base member 540, adjustable member 520, and/or second control member 510 include apertures 560 (e.g., fluid apertures, bone growth material apertures, etc.), as shown in FIG. 15. Apertures 560 may facilitate fluid communication (e.g., for the delivery of bone growth material, etc.) between an exterior and an interior of implant 500. Second control member 510 includes control portions 514 and 516. Control portions 514 and 516 may include sloped portions of second control member 510 configured to contact corresponding sloped portions of adjustable member 520 and cause vertical translation or movement (e.g., up and down, expansive and contractive) of adjustable member 520 in response to horizontal (e.g., side to side) movement of second control member 510. In various embodiments, control portions 514 and 516 are received within control channels 570 and 572 of adjustable member 520. As second control member 510 translates, adjustable member 520 is moved upward or downward due to the angled shape of control channels 570 and 572. The rate of movement of adjustable member 520 can be adjusted by modifying the slope of control channels 570 and 572 relative to second control member 510. Control portions 514 and 516 may include angled portions that are configured to interface with control channels 570 and 572 to affect a vertical (e.g., up and down, expansive or contractive) movement of adjustable member 520 in response to a horizontal translation (e.g., side to side) of second control member 510. In various embodiments, second control member 510 includes guides 513 and 515 configured to direct horizontal translation of second control member 510 and/or limit a range of motion of second control member 510. In various embodiments, base member 540 may include track 562, as shown in FIG. 15. Track 562 may receive guides 513 and 515 and direct motion thereof. For example, track 562 may align second control member 510 to base member 540 throughout horizontal movement, as described above. Second control member 510 may further include end portion 512 configured to couple to bore 542 of base member 540. Bore 542 may retain second control member 510 via end portion 512 while allowing second control member 510 to slide (e.g., relative to bore 542) freely. In various embodiments, bore 542 is formed between bridge 530 and end 534. Bridge 530 may securely couple to end 534 thereby creating bore 542 to receive end portion 512. In some embodiments, bridge 530 is permanently coupled to the base member 540 (e.g., via welding, etc.). Second control member 510 may include translation surface 518 configured to contact adjacent surface 656 of first control member 650 (e.g., an intermediate member, control member, etc.). First control member 650 may receive user input as described below and transfer the user input to second control member 510 by contacting translation surface 518. In various embodiments, surface 656 receives a horizontal force in a first direction from screw 652 and translates the horizontal force into a horizontal force in a second direction. For example, surface 656 may receive a first axial force along axis 506 and translate the force to cause axial motion of second control member 510 along axis 508. In various embodiments, surface 656 is coupled to first control member 650.

First control member 650 may be received within translation aperture 648 of base member 540. First control member 650 may include screw 652, guide 658 and surface 656. Screw 652 may include threaded portion 654 configured to contact a corresponding threaded portion of adjustment collar 640. In various embodiments, threaded portion 654 is a male screw thread to receive a female mating thread. Similar to guides 513 and 515, guide 658 is configured to direct horizontal translation of first control member 650 (e.g., limit a range of motion of first control member 650, etc.). In some embodiments, base member 540 includes track 561, as shown in FIG. 15. Track 561 may receive guide 658 and direct motion thereof. For example, track 561 may align first control member 650 within base member 540 throughout horizontal translation. In various embodiments, first control member 650 translates along axis 506. Additionally or alternatively, tracks 561 and 562 facilitate fluid communication similarly to apertures 560.

Adjustment collar 640 (e.g., an adjustment member, etc.) may be configured to be received within adjustment aperture 648 such that it contacts base member 540 and receives first control member 650. In some embodiments, base member 540 includes aperture 535 and 533 (e.g., as shown in FIG. 15). Aperture 535 and/or aperture 533 may receive a pin 532, 536 (e.g., linkage, collar, etc.) to couple adjustment collar 640 to base member 540. In some embodiments, the pin 532, 536 is received within a groove of adjustment collar 640. In various embodiments, adjustment collar 640 is rotatably received within adjustment aperture 648. Adjustment collar 640 includes collar 642, contact surface 644, and threaded aperture 646. Collar 642 may be a groove to maintain adjustment collar 640 within adjustment aperture 648. Contact surface 644 may be configured to receive a tool to facilitate user manipulation of implant 500. In various embodiments, contact surface 644 is a raised portion of adjustment collar 640 to facilitate transmission of an external rotational force to adjustment collar 640. Threaded aperture 646 may be configured to receive screw 652 of first control member 650 and translate force thereto. In various embodiments, threaded aperture 646 includes a female mating thread.

Figure 14:
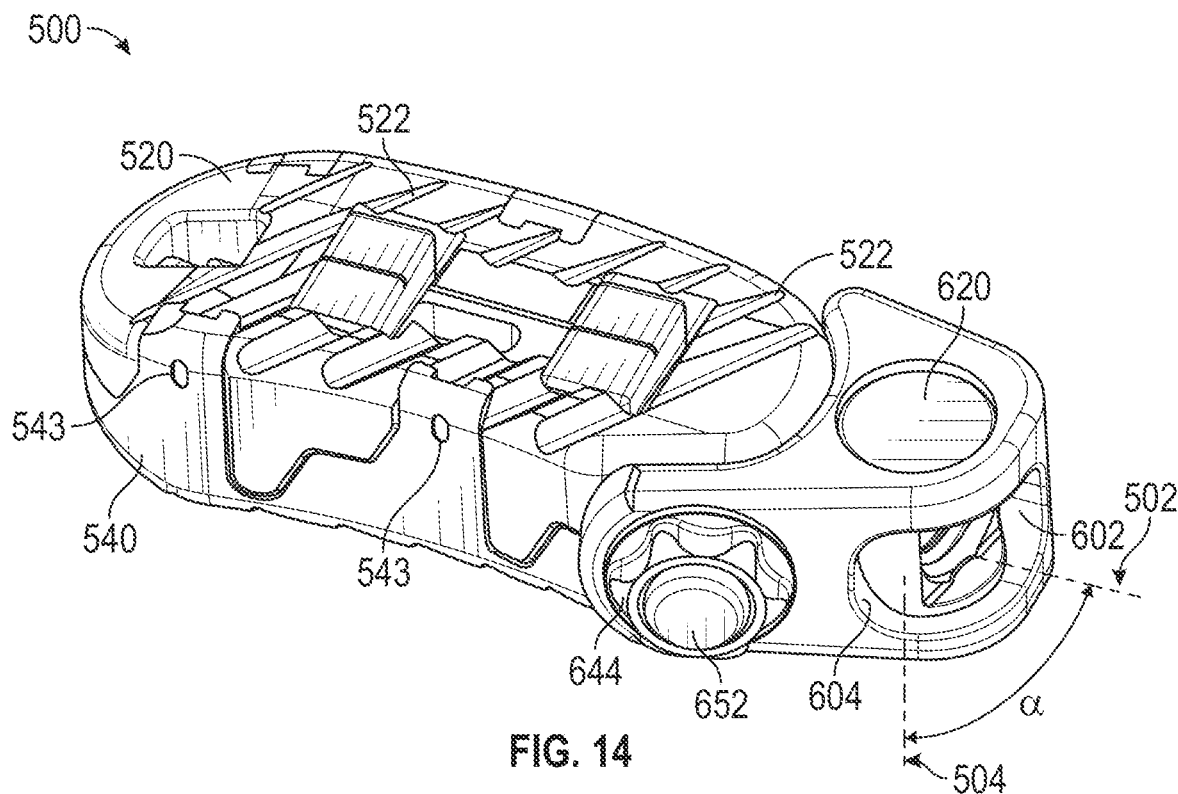
FIG. 14 is a perspective view of a steerable expandable implant, according to another embodiment.

Pivot member 620 may be received within aperture 624 of base member 540. In various embodiments, pivot member 620 is cylindrical. Pivot member 620 may rotate between a first position 502 and a second position 504, as shown in FIG. 14. In various embodiments, rotation of pivot member 620 is limited by limit 602 and/or limit 604. For example, limit 602 may prevent a user using a tool from rotating pivot member 620 farther counter-clockwise than the first position 502. In various embodiments, pivot member 620 may be rotatably received by aperture 626 such that pivot member 620 may rotate within aperture 626 but not decouple from base member 540. Pivot member 620 may include threaded aperture 622 configured to receive a corresponding threaded portion of a tool. In various embodiments, pivot member 620 facilitates positional adjustment of implant 500 as described in greater detail below.

Figure 16:
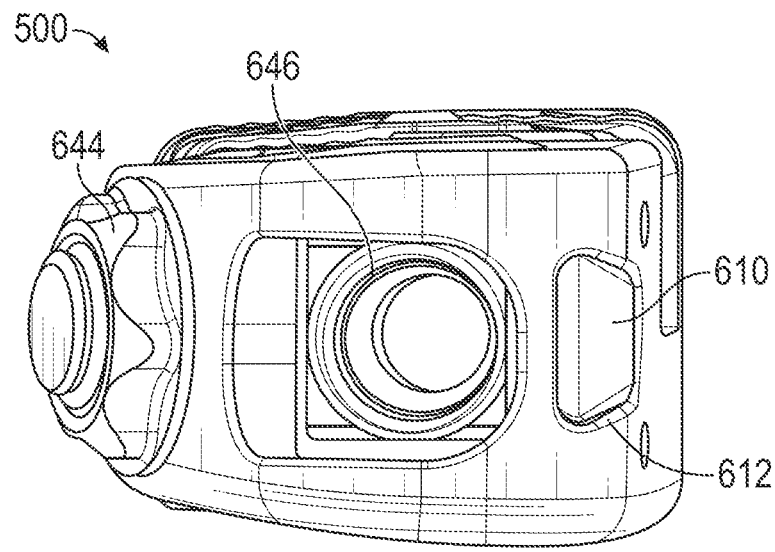
FIG. 16 is a right view of the steerable expandable implant of FIG. 15, according to one embodiment.
Figure 17:
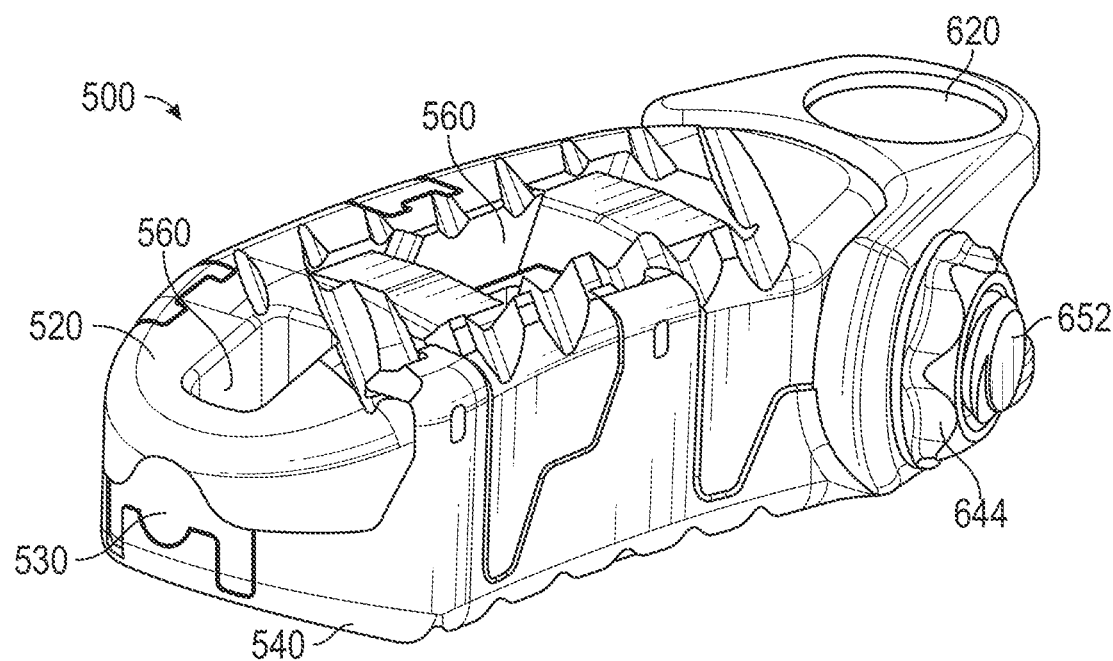
FIG. 17 is a left perspective view of the steerable expandable implant of FIG. 15, according to one embodiment.
Figure 18:
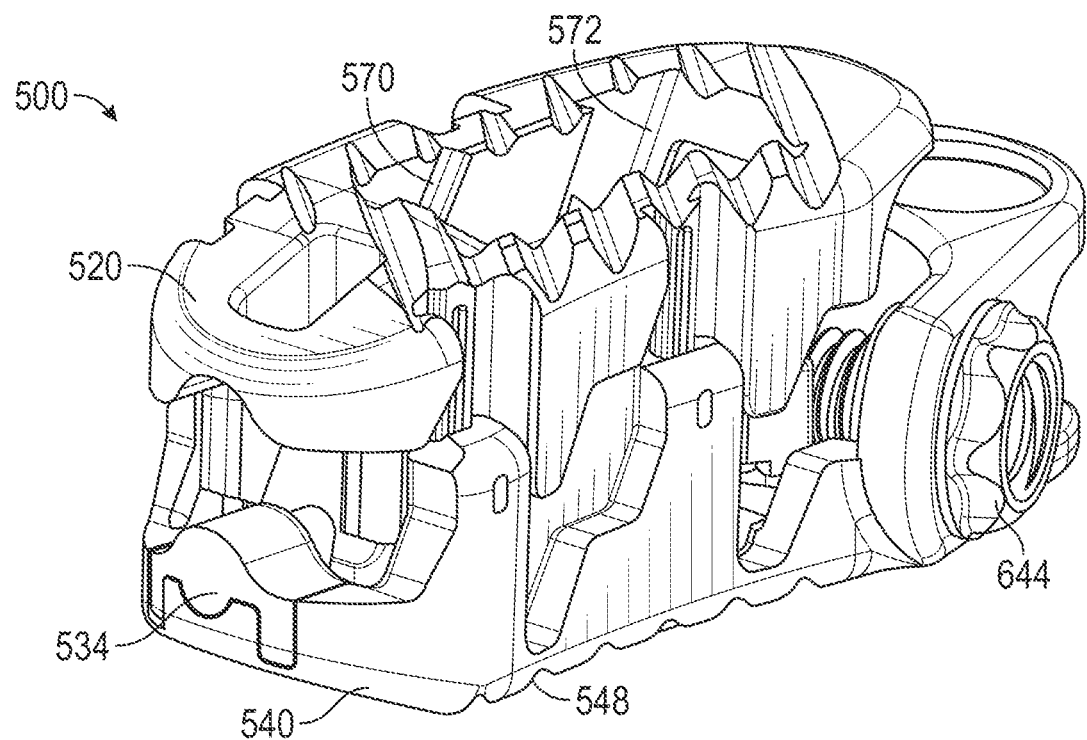
FIG. 18 is a left perspective view of the steerable expandable implant of FIG. 15 in an expanded position, according to one embodiment.
Figure 19:
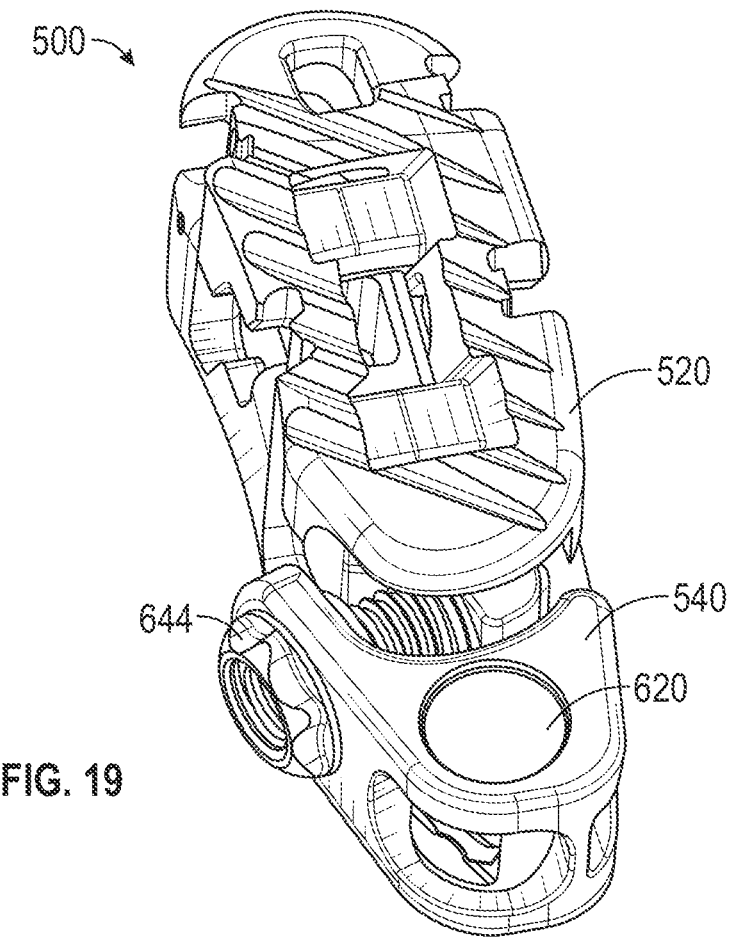
FIG. 19 is a right perspective view of the steerable expandable implant of FIG. 15 in the expanded position, according to one embodiment.
Figure 20:
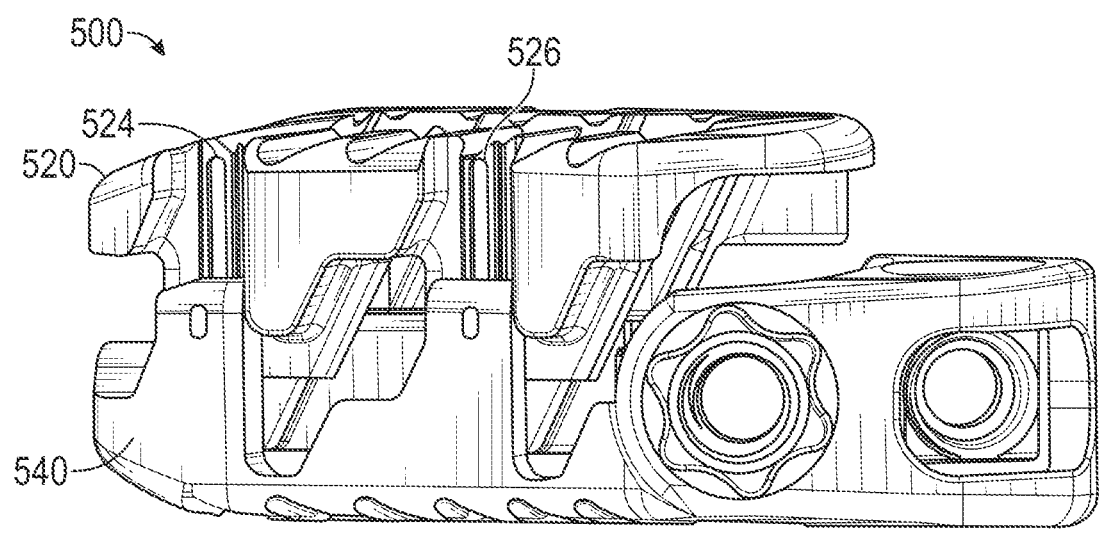
FIG. 20 is a front view of the steerable expandable implant of FIG. 15 in the expanded position, according to one embodiment.
Figure 21:
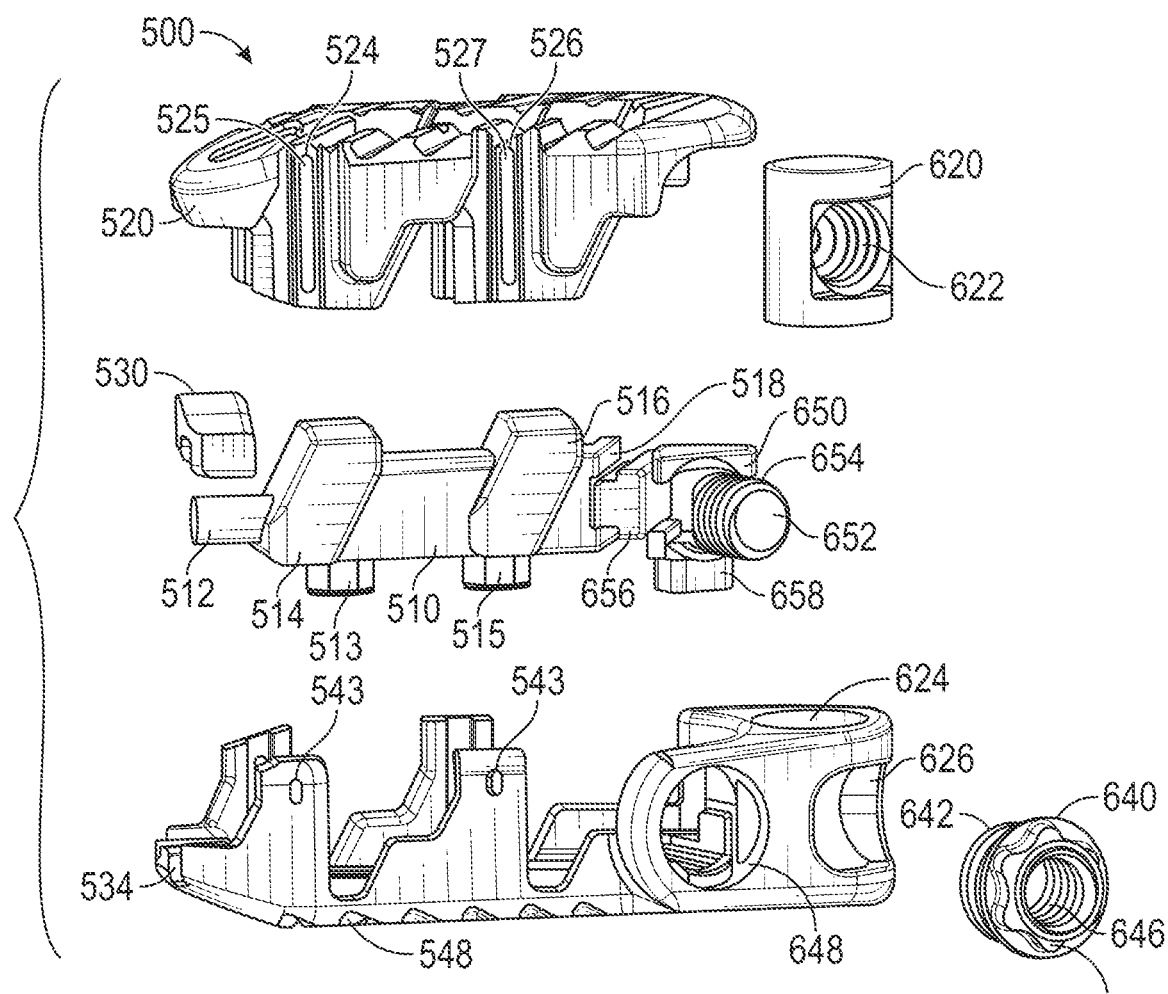
FIG. 21 is an exploded view of the steerable expandable implant of FIG. 15, according to one embodiment.

Base member 540 further includes tool recess 610, as shown in FIG. 16. Tool recess 610 may be configured to receive a tool to facilitate manipulation of implant 500 by a user. In various embodiments, tool recess 610 includes slanted side walls 612 to facilitate coupling to a tool. Tool recess 610 is discussed in greater detail below with reference to FIGS. 27-34.

A non-limiting example of operation of implant 500 is as follows. A tool, such as a coaxial manipulation device, may be attached to implant 500 via pivot member 620. A user may align the manipulation device to implant 500 using tool recess 610. The user may turn pivot member 620 from the first position 502 to the second position 504 within aperture 624, while changing an orientation of implant 500. In the second position 504, the user may engage adjustment collar 640 using the manipulation device. Rotation of adjustment collar 640 causes translation of first control member 650 (e.g., along axis 506). First control member 650 engages of second control member 510, causing translation or other movement of second control member 510 (e.g., along axis 508). Translation of second control member 510 causes control portions 514 and 516 to engage control channels 570 and 572, thereby causing expansion or contraction of adjustable member 520. In various embodiments, first control member 650 and second control member 510 are coupled (e.g., via a tongue and groove joint, a dovetail interface, etc.). Rotation of adjustment collar 640 in a first direction may cause expansion of implant 500 and rotation of adjustment collar 640 in a second direction may cause contraction of implant 500 (e.g., first control member 650 pulls second control member 510, thereby causing movement of adjustable member 520).

Figure 24:
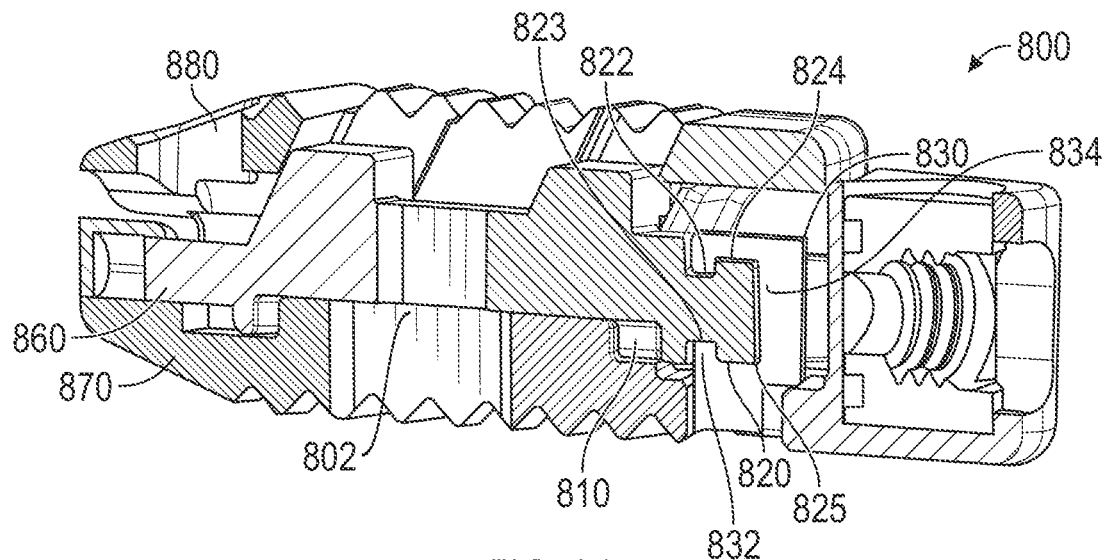
FIG. 24 is a cutaway view of a steerable expandable implant, according to another embodiment.
Figure 25:
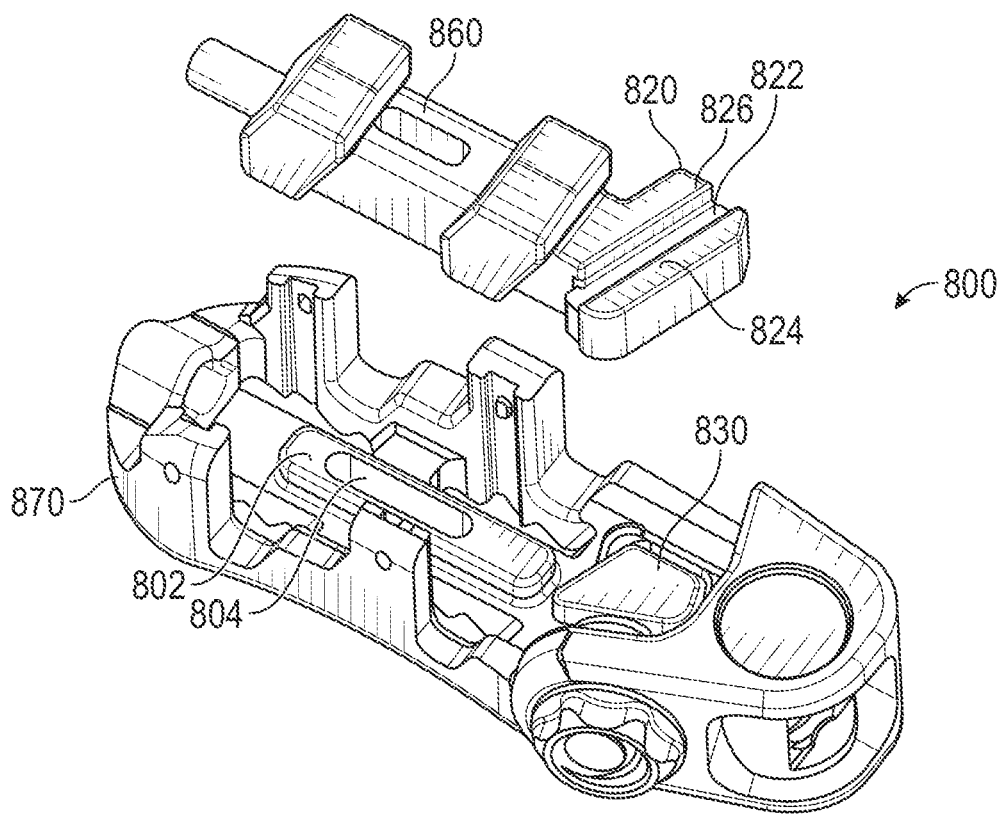
FIG. 25 is an exploded view of the steerable expandable implant of FIG. 24, according to one embodiment.
Figure 26:
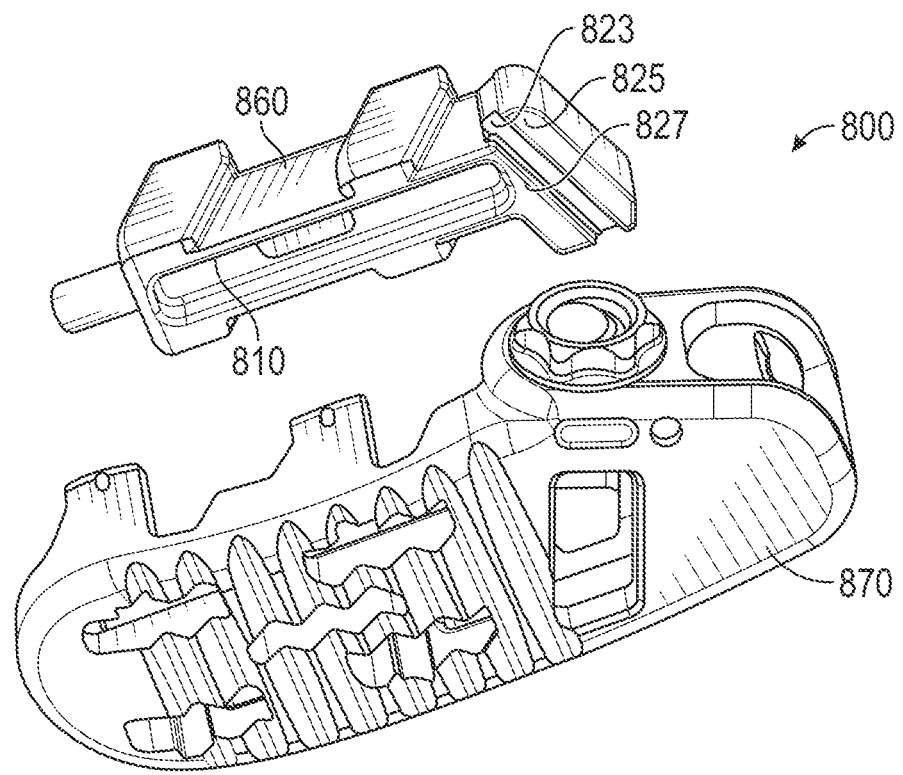
FIG. 26 is another exploded view of the steerable expandable implant of FIG. 24, according to one embodiment.

Referring now to FIGS. 24-26, a steerable expandable implant 800 is shown, according to an exemplary embodiment. Implant 800 may share many of the features of the other inter/intra-body implants discussed elsewhere herein. All such combinations of features are to be understood to be within the scope of the present disclosure. Implant 500 is generally similar to implant 300 and implant 500 in structure and function.

Implant 800 may include base member 870 and adjustable member 880 adjustably coupled to base member 870. Base member 870 and adjustable member 880 are configured to engage adjacent surfaces (e.g., portions of bone, etc.). In various embodiments, base member 870 and/or adjustable member 880 are the same as or share features with base member 540 and/or adjustable member 520.

Base member 870 may include protrusion 802 configured to interface with pocket 810 in second control member 860. Protrusion 802 may facilitate alignment of second control member 860 during translation of second control member 860. For example, protrusion 802 may fit inside of pocket 810 (e.g., alignment channel, etc.) and align second control member 860 with base member 870 during side to side translation of second control member 860. In various embodiments, protrusion 802 is configured to be a track that second control member 860 slides along. In various embodiments, second control member 860 includes pocket 810. Pocket 810 may be a negative space within second control member 860 configured to receive protrusion 802. In various embodiments, protrusion 802 includes aperture 804 (e.g., fluid apertures, bone growth material apertures, etc.), as shown in FIG. 25. Aperture 804 may facilitate fluid communication (e.g., for the delivery of bone growth material, etc.) between an exterior and an interior of implant 800.

Implant 800 further includes second control member 860 (e.g., a control shaft, etc.). Second control member 860 may share many of the features of second control member 510. In various embodiments, second control member 860 includes first control portion 820 configured to interface with first control member 830 (e.g., as shown in FIG. 24). In various embodiments, first control portion 820 and first control member 830 interface using a tongue and groove joint. In various embodiments, first control portion 820 includes first surface 826 and/or second surface 827. First surface 826 and/or second surface 827 may be a portion of first control portion 820 at a first height. In various embodiments, first surface 826 is on a top of first control portion 820 and second surface 827 is on a bottom of first control portion 820. In various embodiments, first control portion 820 includes top channel 822 and bottom channel 823. In various embodiments, top channel 822 and/or bottom channel 823 form a groove to receive a portion of first control member 830 to facilitate coupling first control member 830 to second control member 860. In various embodiments, a surface of top channel 822 and/or bottom channel 823 is at a different height than that of first surface 826 and/or second surface 827 (e.g., a surface of top channel 822 may be below a surface of first surface 826, etc.). First control portion 820 may include third surface 824 and fourth surface 825. In various embodiments, third surface 824 is on a top portion of first control portion 820 and fourth surface 825 is on a bottom portion of first control portion 820. First surface 826, second surface 827, third surface 824, and fourth surface 825 may form top channel 822 and/or bottom channel 823. In some embodiments, a height of third surface 824 is different than a height of first surface 826 (e.g., lower than, etc.). Additionally or alternatively, a height of fourth surface 825 may be different than a height of second surface 827.

In various embodiments, first control member 830 includes groove 834 configured to receive first control portion 820. In various embodiments, first control member 830 includes retention portion 832. Retention portion 832 may be a lip configured to interface with top channel 822 and/or bottom channel 823. In various embodiments, a top portion of groove 834 includes retention portion 832. Additionally or alternatively, a bottom portion of groove 834 may include retention portion 832. In various embodiments, groove 834 and retention portion 832 are configured to couple first control member 830 to second control member 860 while facilitating translation of second control member 860. For example, first control portion 820 may slide within groove 834 to translate movement of first control member 830 in a first direction to movement of second control member 860 in a second direction. In various embodiments, an axis of groove 834 and an axis of top channel 822 and/or bottom channel 823 are aligned. In various embodiments, first control portion 820 slideably engages first control member 830. In various embodiments, first control member 830 is the same or similar to first control member 650. For example, first control member 830 may be first control member 650 but including pocket 810.

Figure 27:
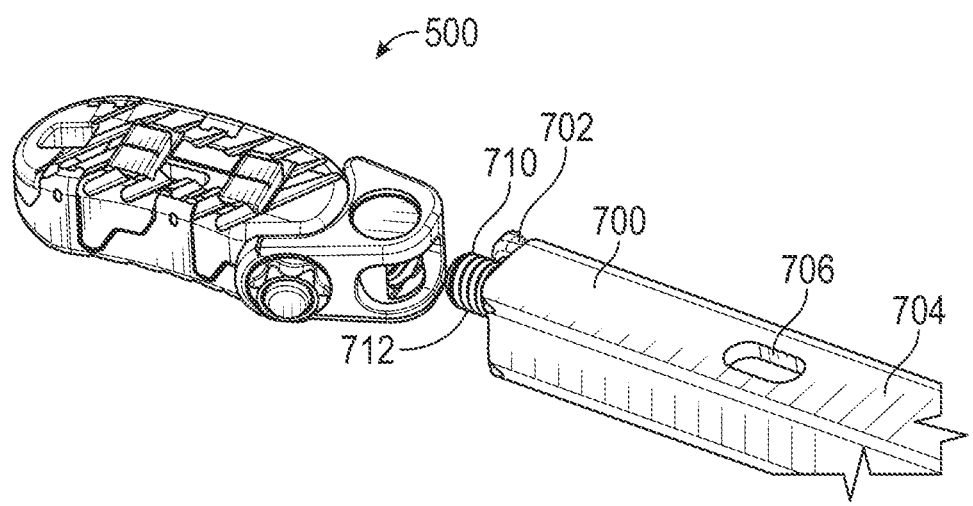
FIG. 27 is a perspective view of a tool for positioning an implant, according to one embodiment.
Figure 28:
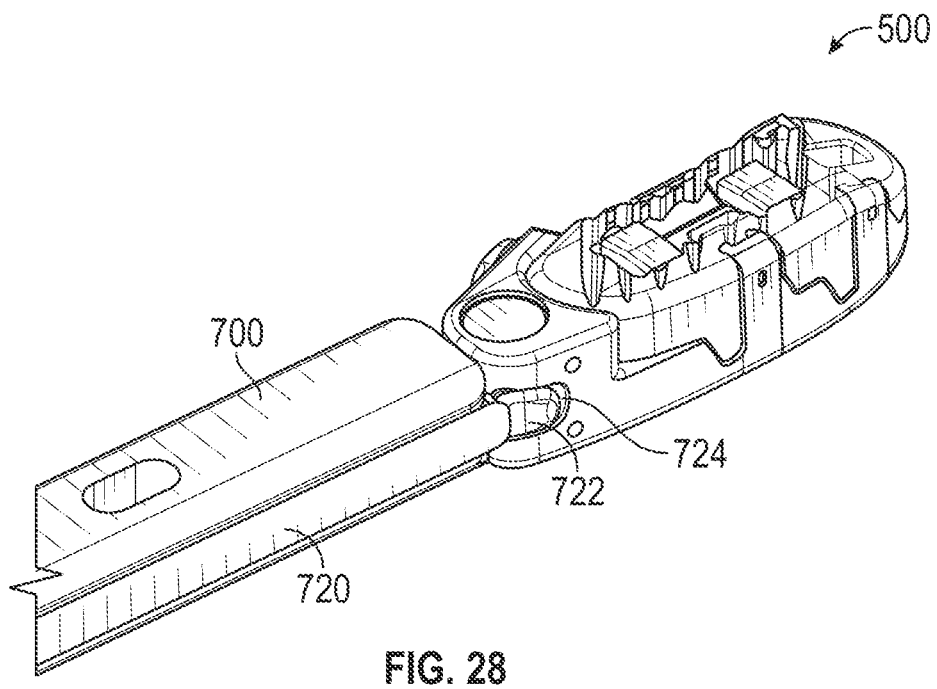
FIG. 28 is a perspective view of the tool of FIG. 27 aligning to an implant in a first configuration, according to one embodiment.
Figure 29:
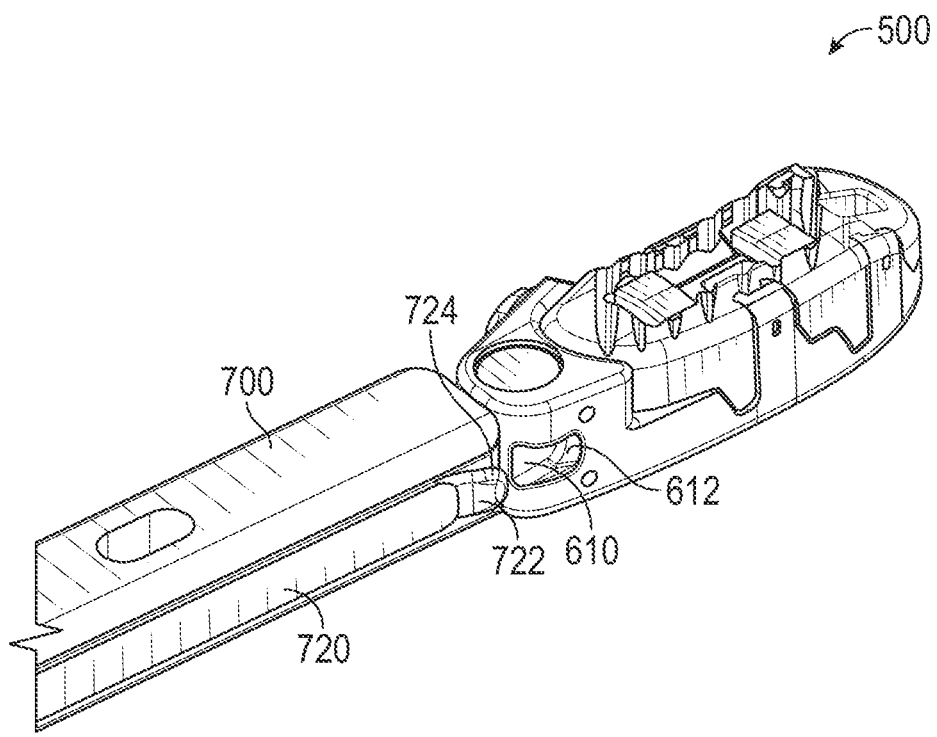
FIG. 29 is a perspective view of the tool of FIG. 27 coupled to an implant in a first configuration, according to one embodiment.
Figure 30:
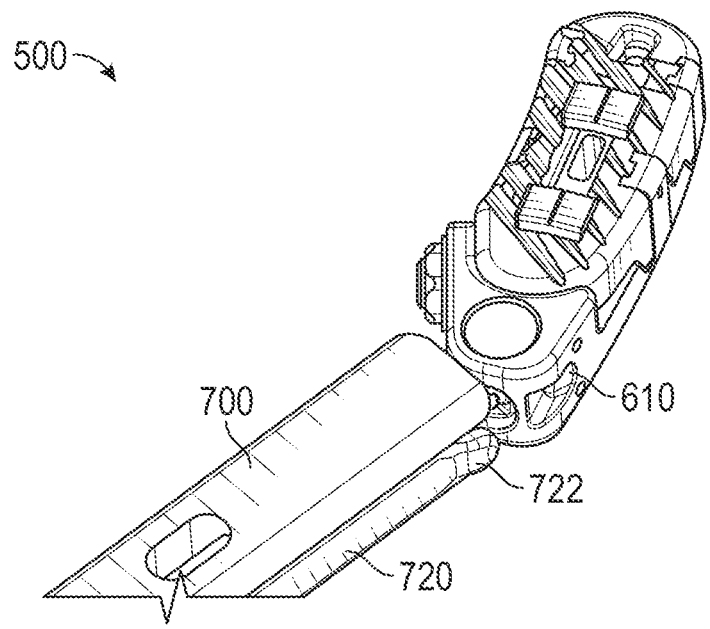
FIG. 30 is a perspective view of the tool of FIG. 27 manipulating an implant, according to one embodiment.
Figure 31:
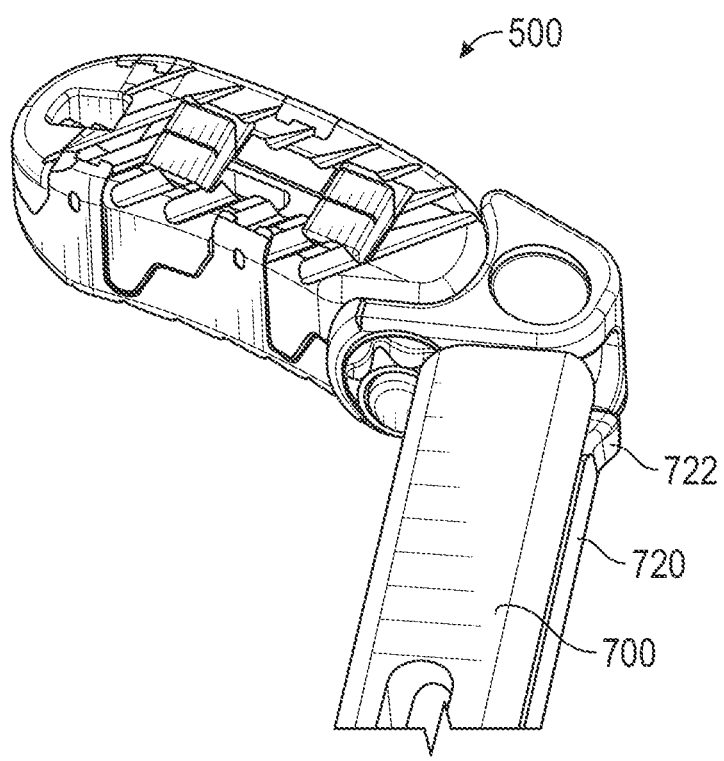
FIG. 31 is a perspective view of the tool of FIG. 27 coupled to an implant in a second configuration, according to one embodiment.
Figure 32:
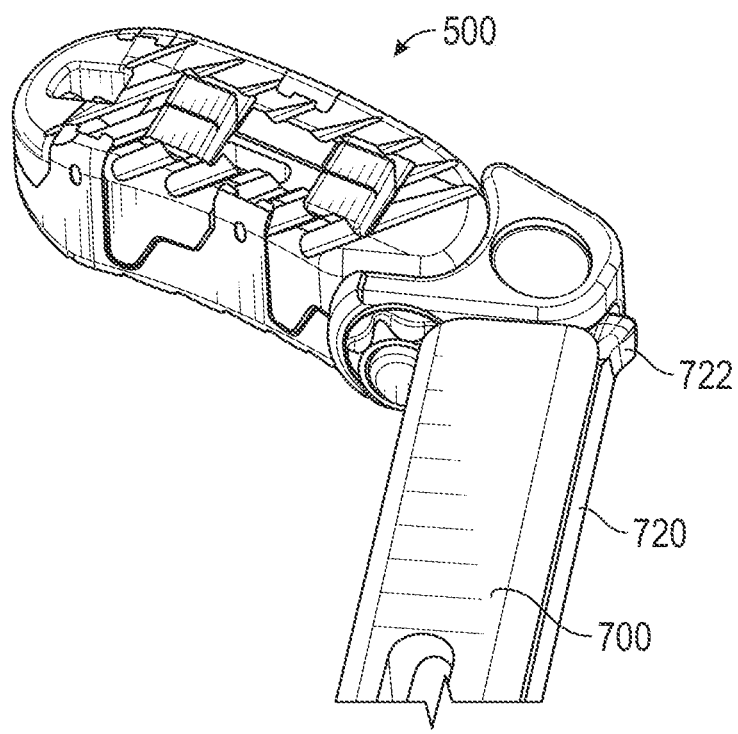
FIG. 32 is a perspective view of the tool of FIG. 27 aligning to an implant in a second configuration, according to one embodiment.
Figure 33:
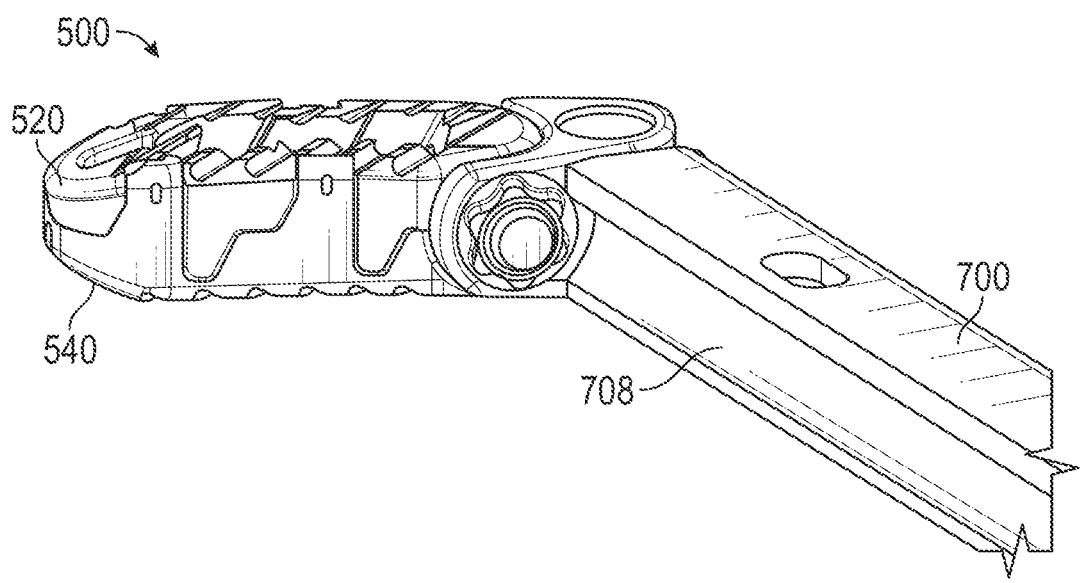
FIG. 33 is a perspective view of the tool of FIG. 27 coupled to an implant in a collapsed position, according to one embodiment.
Figure 34:
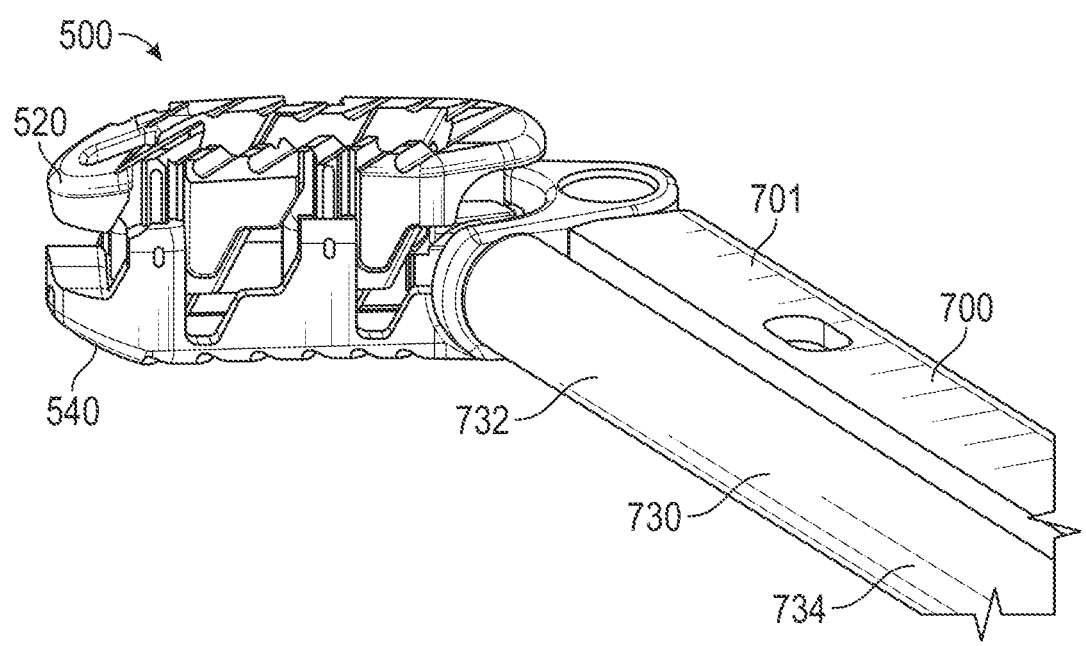
FIG. 34 is a perspective view of the tool of FIG. 27 coupled to an implant in an expanded position, according to one embodiment.

Referring now specifically to FIGS. 27-34, tool 700 for manipulation of implant 500 is shown, according to an embodiment. In brief summary, a user may operate tool 700 to manipulate a position of implant 500 and/or to expand and/or contract implant 500. FIGS. 27-28 illustrate tool 700 connecting to implant 500. FIGS. 29-31 illustrate rotation of implant 500 using tool 700. FIGS. 32-34 illustrate expansion of implant 500 using tool 700.

Referring now specifically to FIGS. 27-28, tool 700 for manipulation of implant 500 is shown, according to an exemplary embodiment. Tool 700 is shown to include first end 702 and second end 704. In various embodiments, a user operates tool 700 using second end 704. First end 702 may include coupling portion 710 configured to couple to pivot member 620. Coupling portion 710 may include threaded portion 712. Threaded portion 712 may be a male screw thread corresponding to the female threading of threaded aperture 622. A user may operate coupling portion 710 via the second end 704 to rotate the coupling portion 710 and cause tool 700 to couple to implant 500. In some embodiments, tool 700 includes aperture 706 to facilitate viewing inside tool 700. For example, a user may monitor rotation of coupling portion 710 via aperture 706. Additionally or alternatively, aperture 706 may include one or more indicators. For example, aperture 706 may include an indicator to show when tool 700 is fully coupled to implant 500. Tool 700 may further include coupling arm 720. Coupling arm 720 may be configured to align tool 700 to implant 500 and facilitate manipulation of implant 500. Coupling arm 720 includes coupling portion 722 configured to be received by coupling aperture 610. In various embodiments, coupling portion 722 includes slanted portion 724 corresponding to slanted side walls 612. For example, slanted portion 724 may be wedge shaped to facilitate axial (e.g., in and out) coupling of coupling arm 720 to coupling aperture 610 but prevent non-axial (e.g., side to side, up and down, etc.) uncoupling of the coupling arm 720 from coupling aperture 610. In one embodiment, rotation of pivot member 620 via tool 700 is prevented when coupling arm 720 is engaged with coupling aperture 610.

In various embodiments, tool 700 couples to implant 500 while pivot member 620 is in a first position. For example, an axis of threaded aperture 622 may be aligned with an axis of implant 500 and an axis of tool 700 in the first position (e.g., as shown for example in FIGS. 27-29). To attach tool 700 to implant 500, a user may align tool 700 to implant 500 using coupling arm 720 by coupling arm 720 with coupling aperture 610 (e.g., by extending coupling portion 722 within coupling aperture 610). The user may then rotate coupling portion 710 to couple tool 700 to pivot member 620.

Referring now to FIGS. 29-31, rotation of tool 700 relative to implant 500 is shown, according to an exemplary embodiment. To rotate implant 500 using tool 700, coupling arm 720 is retracted to decouple from implant 500 (e.g., FIG. 29). A user may manipulate implant 500 using tool 700 to turn pivot member 620 thereby causing rotation of implant 500. In various embodiments, tool 700 is used to rotate implant 500 from a first position to a second position. In the first position, an axis of implant 500 may be aligned with an axis of tool 700. In the second position, an axis of implant 500 may be offset from an axis of tool 700 (e.g., 60° difference, etc.). A user may align implant 500 in the second position by extending coupling arm 720 to contact coupling aperture 610 (e.g., FIG. 32).

Referring now to FIGS. 32-34, expansion of implant 500 is shown, according to an exemplary embodiment. Tool 700 is shown to include expansion member 730. In some embodiments, expansion member 730 is coupled (e.g., slideably coupled) to main body 701 of tool 700. Additionally or alternatively, expansion member 730 may be removably coupled to tool 700 such that it may contact and/or couple to tool 700 during use and decouple from tool 700 when not in use. Expansion member 730 may be configured to contact and rotate contact surface 654 and/or contact surface 644, as shown in FIG. 34. Expansion member 730 may contact an adjacent surface 708 of tool 700 configured to receive and align expansion member 730. Adjacent surface 708 may be a concave trough configured to correspond to a shape of expansion member 730. Expansion member 730 includes first end 732 and second end 734. In various embodiments, a user manipulates expansion member 730 via second end 734. First end 732 may couple to contact surface 654 to facilitate rotation thereof. For example, first end 732 may include a female recessed surface corresponding to the male raised portion of contact surface 654.

In various embodiments, a user couples expansion member 730 to contact surface 654 by extending expansion member 730 down the axis of tool 700 to contact surface 654. The user may manipulate expansion member 730 to rotate expansion member 730. Rotation of expansion member 730 transfers rotational force to adjustment collar 640. Rotation of adjustment collar 640 causes translation of screw 652 (e.g., in and out along axis 506). Translation of screw 652 causes surface 656 to contact translation surface 518, thereby causing horizontal translation of translation surface 518. For example, expansive rotation (e.g., rotation causing screw 652 to translate into implant 500) of expansion member 730 causes second control member 510 to translate horizontally along an axis of implant 500 in the direction of bridge 530 (e.g., away from pivot member 620) thereby causing control portions 514 and 516 to contact control channels 570 and 572 and cause expansion of adjustable member 120. Rotation of expansion member 730 may thereby cause expansion or contraction of implant 500. In various embodiments, second control member 510 operates similarly as described with reference to implant 300.

Referring now to FIGS. 35-43, a steerable expandable implant 900 is shown, according to one embodiment. Implant 900 may share many of the features of the other implants described elsewhere herein. All such combinations of features are to be understood to be within the scope of the present disclosure. Implant 900 is generally similar to implant 800, implant 500, implant 300, and implant 100 in structure and function.

Referring to the implant 900 generally, the implant 900 may be inserted into a patient while in a first orientation. Once inserted, a tool may be used to engage a portion of the implant 900 to reorient the implant 900 into a second orientation. The implant 900 may be positioned within a desired space (e.g., between adjacent portions of bone, etc.) while in a first, collapsed position. A tool may be used to engage a portion of the implant 900 to manipulate the implant 900 into a desired position. Once in a desired position, the same or a subsequent tool may be used to engage a portion of the implant 900 to expand the implant 900 to a desired degree of expansion. It should be understood that based on a particular application, the implant 900 may be utilized in a fully collapsed position, a fully expanded position, or any intermediate position therebetween. It should also be understood that components of the implant 900 may generally be formed of one or more rigid materials, for example titanium or another suitable metal (e.g.). Once the implant 900 is properly positioned and expanded to a desired height, bone graft material may be delivered by way of an access aperture and placed into a central cavity of implant 900. The various apertures in and through the implant 900 may facilitate the growth of bone material in and around the implant 900 to further stabilize the implant 900.

Referring still to the implant 900 generally, the implant 900 may include a first support member and a second support member, the support members configured to engage one or more portions of bone. Further, the first support member may be movable relative to the second support member, for example between a collapsed position and an expanded position. The implant 900 may also include a first control member slidably coupled to a second control member, such that the control members are configured to move relative to one another. The first control member and/or second control member may further be coupled to a first end member and/or a second end member. The end members may contact or engage the support members, and may be configured to cause vertical translation or movement of the support members relative to one another. For example, the first control member may be manipulated, causing movement of the first control member and/or the second control member relative to one another. The movement of the control member(s) may cause the first end member and/or the second end member to move along an axis (e.g., toward the other along a longitudinal axis, etc.). The movement of the end member(s) (e.g., toward one another, etc.) may cause the end members to engage the support members, causing vertical movement of the first support member relative to the second support member (e.g., the support members moving apart vertically).

Referring to FIGS. 35-43, in some embodiments the implant 900 includes a base member 970 (e.g., a first support or member, a bottom support or member, etc.) and an adjustable member 980 (e.g., a second support or member, a bottom support or member, etc.) operatively coupled to the base member 970. The base member 970 and the adjustable member 980 may be configured to engage adjacent surfaces (e.g., portions of bone, etc.). In various embodiments, the base member 970 and/or the adjustable member 980 share similar features with the base member 140 and/or the adjustable member 120, the base member 340 and/or the adjustable member 320, the base member 540 and/or the adjustable member 520, and/or the base member 870 and/or the adjustable member 880.

In various embodiments, the base member 970 includes an alignment channel 945, having alignment portions 944 and 946, to receive an alignment projection 925, having alignment portions 924 and 926, of the adjustable member 980. Alignment portions 944 and 946 and alignment portions 924 and 926 may align the base member 970 and the adjustable member 980. For example, the alignment components (e.g., the alignment channel 945, the alignment projection 925, the alignment portions 944 and 946 and/or the alignment portions 924 and 926) may facilitate alignment of the base member 970 to the adjustable member 980 during expansion of the implant 900. The alignment components may couple to one another and allow for vertical (e.g., up and down, contractive and expansive, etc.) movement of the base member 970 and the adjustable member 980. In some embodiments, the alignment components have a relatively close fit to facilitate alignment between the base member 970 and the adjustable member 980, while in other embodiments the alignment components have a relatively loose fit to facilitate a desired angular offset between the base member 970 and the adjustable member 980. In some embodiments, the alignment components (e.g., the alignment portions 944 and 946 and/or the alignment portions 924 and 926) form a tongue and groove joint. In other embodiments, the alignment components (e.g., the alignment portions 944 and 946 and/or the alignment portions 924 and 926) include pin slots configured to receive a pin to limit expansion and/or contraction of the base member 970 and/or the adjustable member 980, and/or any other suitable alignment components.

According to some embodiments, the base member 970 and/or the adjustable member 980 also include apertures 1060 (e.g., fluid apertures, bone growth material apertures, etc.). The apertures 1060 may facilitate fluid communication (e.g., for the delivery of bone growth material, etc.) between an exterior and an interior of the implant 900. In various embodiments, the apertures 1060 are also configured to receive a stabilizing member. The stabilizing member may couple the base member 970 and/or the adjustable member 980 at the apertures 1060, and facilitate a desired alignment during movement of the base member 970 and/or the adjustable member 980 (e.g., up and down, contractive and expansive, etc.), as discussed below. The base member 970 and the adjustable member 980 are also shown to include surface patterns 922 and 948, respectively. The surface patterns 922 and 948 may be configured to promote bonding to an adjacent surface (e.g., a portion of bone) and prevent slippage of implant 900. In some embodiments, surface patterns 922 and 948 are patterned ridges; however, in other embodiments the surface patterns 922 and/or 948 are another suitable pattern, interface, and/or surface.

In some embodiments, the base member 970 includes control interfaces 1070 and 1071 and the adjustable member 980 includes control interfaces 1072 and 1073. In various embodiments, control interfaces 1070-1073 are sloped portions of the base member 970 and the adjustable member 980, respectively, and are configured to contact corresponding sloped portions of components of the implant 900 (e.g., end members, etc.) to cause vertical translation or movement (e.g., up and down, contractive and expansive, etc.) of the base member 970 and/or the adjustable member 980. In various embodiments, control interfaces 1070-1073 are angled, such that translation of a control member causes movement of the base member 970 and/or the adjustable member 980. The rate of movement of the base member 970 and/or the adjustable member 980 may be adjusted by modifying the slope of the control interfaces 1070-1073. In some embodiments, the control interfaces 1070-1073 extend from the base member 970 and/or the adjustable member 980, such that a void or space is formed at ends of the base member 970 (e.g., between control interfaces 1070, control interfaces 1071, etc.) and ends of the adjustable member 980 (e.g., between control interfaces 1072, control interfaces 1073). The void or space of the base member 970 and/or the adjustable member 980 may be configured to receive one or more components of the implant 900 (e.g., end members, a projection of an end member, etc.), for example to facilitate alignment of the base member 970 and/or the adjustable member 980 relative to one or more end members (e.g., lateral alignment during horizontal translation of the end members, a control member, etc.). In other embodiments, control interfaces 1070-1073 include additional components (e.g., channels, grooves, protrusions, etc.), for example to facilitate alignment of the base member 970 and/or the adjustable member 980 with one or more components of the implant 900 (e.g., end members, etc.) during movement of the base member 970 and/or the adjustable member 980.

In some embodiments, the base member 970 further includes a coupling aperture 1010 configured to receive a tool to facilitate manipulation of the implant 900 (e.g., by a user, etc.). The coupling aperture 1010 may be substantially circular, and may extend into the base member 970 along an axis. In various embodiments, the axis of the coupling aperture 1010 is aligned with an axis of one or more components of the implant 900 (e.g., a control member, an adjustment aperture, etc.), and/or is offset from an axis of another component of the implant 900 (e.g., another control member, a longitudinal axis of the base member 970, a longitudinal axis of the adjustable member 980, etc.). According to other embodiments, the coupling aperture 1010 facilitates coupling the implant 900 to a tool, for example by receiving a coupling arm (e.g., the coupling arm 720, etc.), a coupling portion (e.g., the coupling portion 722, etc.), and/or any other suitable coupling component of a tool (e.g., the slanted portion 724, an elongated member, etc.). As discussed above, the coupling aperture 1010 may be configured to facilitate axial (e.g., in and out) coupling of a tool to the coupling aperture 1010, but prevent non-axial (e.g., side to side, up and down, etc.) uncoupling of the tool from the coupling aperture 1010.

In some embodiments, the implant 900 also includes a stabilizing member 902. The stabilizing member 902 may be configured to interface with one or more surfaces of the base member 970 and/or the adjustable member 980 (e.g., at the apertures 1060), and may facilitate alignment of the base member 970 to the adjustable member 980 during contraction or expansion of the implant 900. The stabilizing member 902 may include one or more substantially flat surfaces (e.g., to interface with one or more substantially flat surfaces of the base member 970 and/or the adjustable member 980), and/or one or more substantially curved surfaces. In various embodiments, the stabilizing member 902 includes one or more apertures, for example a first stabilizing aperture 904 and a second stabilizing aperture 905 (shown in FIGS. 42-43). The first stabilizing aperture 904 and second stabilizing aperture 905 may be substantially perpendicular, and may be configured to receive one or more components of the implant 900. For example, the first stabilizing aperture 904 may be substantially aligned with a longitudinal axis of the base member 970 and/or the adjustable member 980, and may be configured to receive a control member (e.g., a second control member, etc.). The second stabilizing aperture 905 may be substantially perpendicular to the first stabilizing aperture 904, and may be configured to receive a pin 941. The pin 941 may be formed of a rigid metal (e.g., cobalt chrome, etc.) or other suitable material, and may be configured to facilitate alignment of (e.g., translationally fix, etc.) the stabilizing member 902 relative to the control member, as discussed below. In some embodiments, the stabilizing member 902 is configured to move along an axis aligned with a longitudinal axis of the base member 970 and/or the adjustable member 980 (e.g., during translation of the control member), while maintaining alignment (e.g., vertical, etc.) of the base member 970 and/or the adjustable member 980.

In some embodiments, the implant 900 also includes a first control member 930 and a second control member 960 (e.g., a control shaft, etc.). In various embodiments, the first control member 930 shares features of the first control member 650 and/or the first control member 830, and/or the second control member 960 shares features of the second control member 510 and/or the second control member 860. In other embodiments, the first control member 930 is slidably coupled to the second control member 960, and manipulation of the first control member 930 causes the base member 970 and/or the adjustable member 980 to move (e.g., up/down, expand/contract, etc.). In some embodiments, the first control member 930 is configured to translate along an axis (e.g., shown as axis 906) etc.), and/or the second control member 960 is configured to translate along an axis (e.g., shown as axis 908) relative to one or more components of the implant 900 (e.g., an end member, the base member 970, the adjustable member 980, etc.). In various embodiments, the first control member 930 and/or the second control member 960 is/are formed of a rigid metal (e.g., cobalt chrome, etc.) or other suitable material, for example to withstand forces generated during manipulation of the first control member 930, and/or movement of the base member 970 and/or the adjustable member 980.

As shown, an axis of the first control member 930 is angularly offset from an axis of the second control member 960; however, in other embodiments the axis of the first control member 930 is aligned with the axis of the second control member 960. Further, the axis of the first control member 930 may be angularly offset from an axis of the base member 970 and/or an axis of the adjustable member 980 (e.g., a longitudinal axis, etc.), and/or the axis of the second control member 960 may be aligned with the axis of the base member 970 and/or the axis of the adjustable member 980 (e.g., a longitudinal axis, etc.). In yet other embodiments, the axis of the first control member 930 is angularly aligned and/or angularly offset from other components of the implant 900 (e.g., aligned with the axis of the coupling aperture 1010, an alignment collar, etc.), and/or the axis of the second control member 960 is angularly aligned and/or angularly offset from other components of the implant 900.

In various embodiments, the second control member 960 includes a first control portion 920 configured to interface with the first control member 930 (e.g., shown in FIGS. 41-43) and/or other components of the implant 900. In some embodiments, the first control portion 920 and the first control member 930 interface via any suitable interface (e.g., pin-hitch fastener, tongue and groove interface, etc.), as discussed below. In various embodiments, the first control portion 920 includes a first surface 1026 and a second surface 1027. The first surface 1026 and/or the second surface 1027 may be a portion of the first control portion 920 at a first height (e.g., with another portion of the first control portion 920 at a second height, etc.). In various embodiments, the first surface 1026 is on a top portion of the first control portion 920, and the second surface 1027 is on a bottom portion of the first control portion 920. In other embodiments, the first control portion 920 includes one or more channels (e.g., a top channel, a bottom channel, etc.), which may form an aperture shown as control portion aperture 923. In various embodiments, the control portion aperture 923 receives a protrusion (e.g., shown as pin 951) to facilitate coupling the first control member 930 to the second control member 960, as discussed below. The pin 951 may be formed of a rigid metal (e.g., cobalt chrome, etc.) or other suitable material, so as to slidably couple the first control member 930 to the second control member 960.

Figure 41:
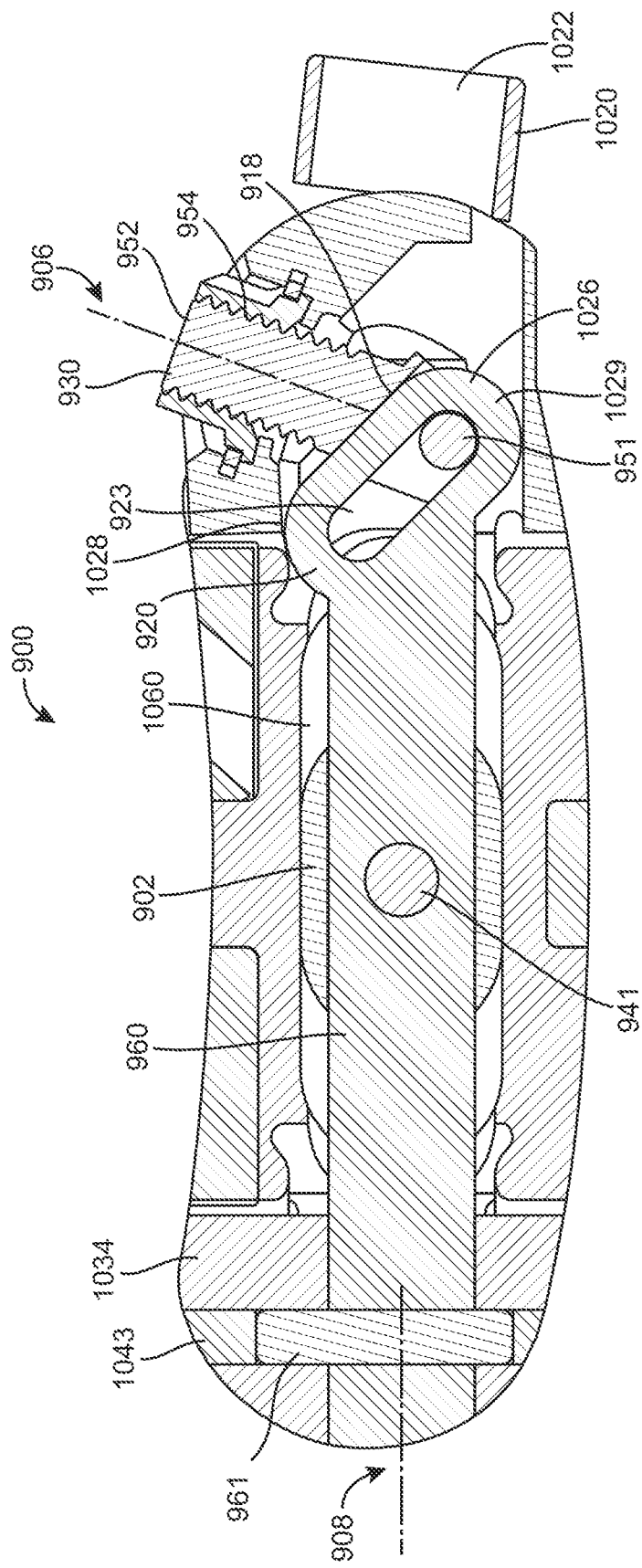
FIG. 41 is a cutaway top view of the steerable expandable implant of FIG. 35, according to one embodiment.
Figure 42:
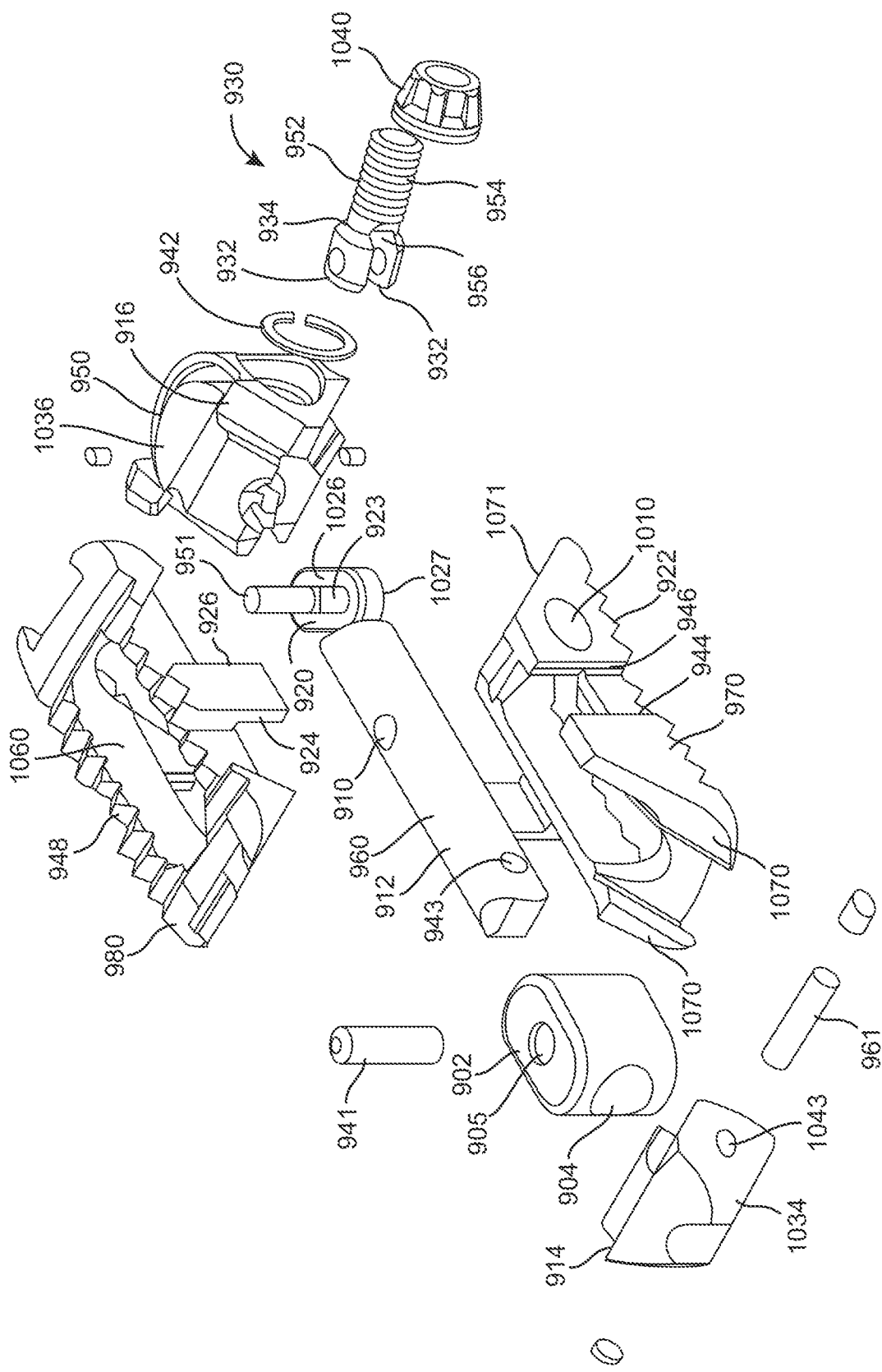
FIG. 42 is an exploded view of the steerable expandable implant of FIG. 35, according to one embodiment.
Figure 43:
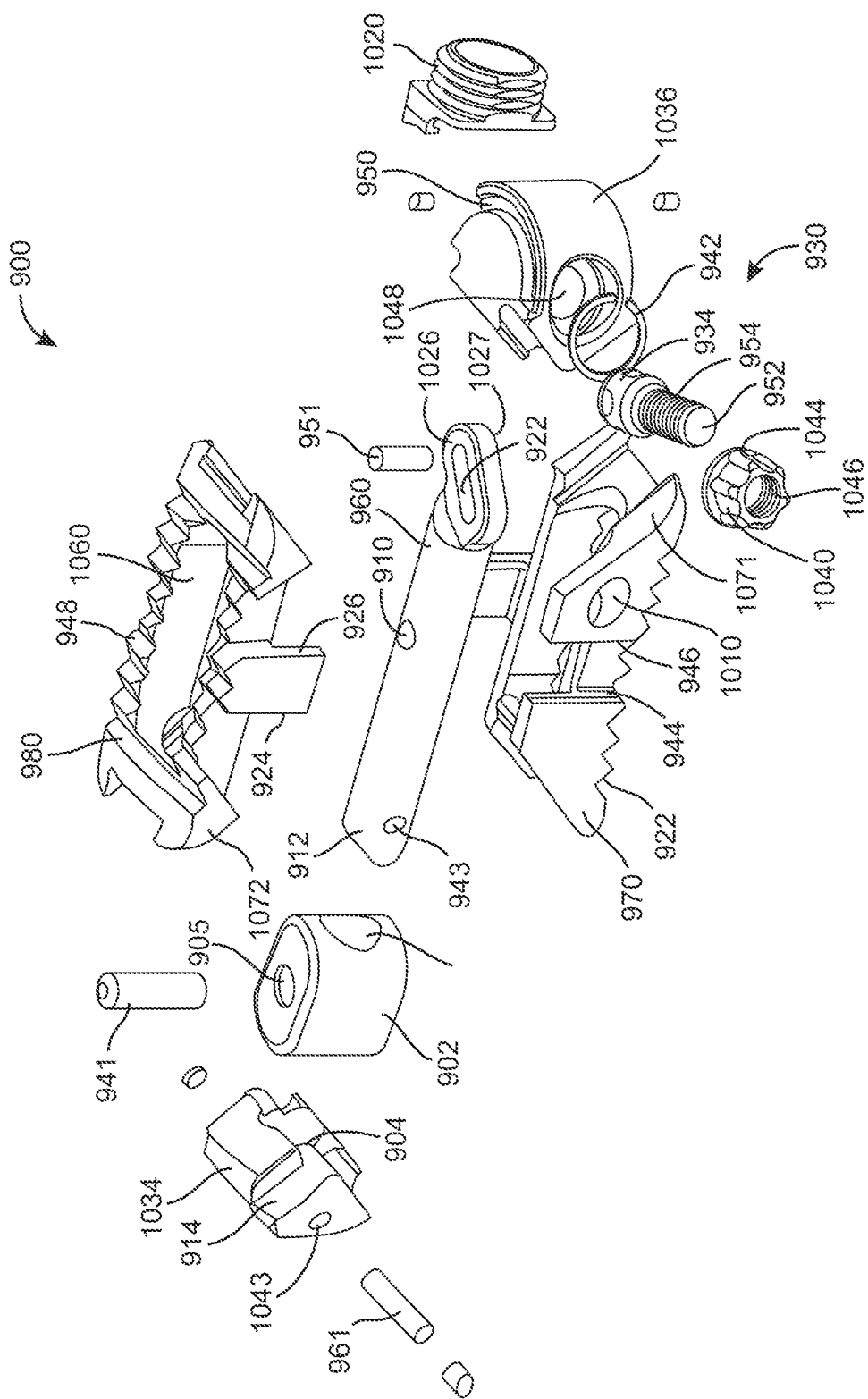
FIG. 43 is another exploded view of the steerable expandable implant of FIG. 35, according to one embodiment.

In some embodiments, the first control portion 920 also includes a third surface 1028 and/or a fourth surface 1029 (as shown in FIG. 41). In various embodiments, the third surface 1028 is a first side portion of the first control portion 920 and the fourth surface 1029 is a second side portion of the first control portion 920. In some embodiments, the first control portion 920 also includes a translation surface 918, which is configured to contact an adjacent surface 956 of the first control member 930 (as shown in FIG. 41), so as to facilitate translation of the second control member 960 and/or the first control member 930. The first surface 1026, the second surface 1027, the third surface 1028, the fourth surface 1029, and/or the translation surface 918 may define the control portion aperture 923. In some embodiments, the first control member 930 is configured to translate in a first direction (e.g., along axis 906) relative to one or more components of the implant 900 (e.g., an end member, etc.). Translation of the first control member 930 may, for example cause the pin 951 to engage a wall defining the control portion aperture 923 and/or cause the surface 956 to contact the translation surface 918, such that the first control member 930 and/or the second control member 960 translate relative to one another. As the first control member 930 and/or the second control member 960 translate, the third surface 1028 and/or the fourth surface 1029 may contact adjacent surfaces of one or more components of the implant 900 (e.g., one or more internal alignment sidewalls of an end member, the base member 970, the adjustable member 980, etc.), so as to facilitate alignment (e.g., lateral alignment, etc.) of the second control member 960 relative to components of the implant 900 (e.g., an end member, the base member 970, the adjustable member 980, etc.).

In some embodiments, the second control member 960 also includes an end portion 912 configured to couple one or more components of the implant 900 (e.g., an end member). The end portion 912 may include an aperture 943 configured to receive a pin 961, so as to couple the second control member 960 to one or more components of the implant 900 (e.g., an end member, etc.). The pin 961 may be formed of a rigid metal (e.g., cobalt chrome, etc.) or other suitable material, so as to securely couple the second control member 960 to one or more components of the implant 900 (e.g., an end member). In various embodiments, the second control member 960 further defines a space, shown as aperture 910, configured to receive a protrusion, shown as the pin 941. As discussed above, the second control member 960 may be configured to be received by the stabilizing member 902 (e.g., via the first stabilizing aperture 904). The pin 941 may fit inside the stabilizing member 902 (e.g., via the second stabilizing aperture 905) and the aperture 910 of the second control member 960, and align the second control member 960 with the stabilizing member 902. In other embodiments, the pin 941 aligns (e.g., translationally fixes, etc.) the stabilizing member 902 relative to the second control member 960, such that the stabilizing member 902 moves with the second control member 960 during translation of the second control member 960.

According to some embodiments, the first control member 930 is received within an aperture of one or more components of the implant 900 (e.g., an end member, etc.), and is configured to couple the second control member 960, as discussed below. The first control member 930 may include a groove 934 configured to receive the first control portion 920 of the second control member 960. The first control member 930 (e.g., the groove 934) may include a retention portion 932, or a plurality of retention portions 932, and the surface 956. The retention portion 932 may be configured to interface with the control portion aperture 923, the first surface 1026, and/or a second surface 1027 of the first control portion 920. The surface 956 may be configured to interface with the translation surface 918 of the first control portion 920. In some embodiments, the retention portion 932 includes an aperture (and/or each of the plurality of retention portions 932 include an aperture), and may be configured to receive a protrusion (e.g., a pin 941). In various embodiments, the groove 934 and the retention portion 932 are configured to couple the first control member 930 to the second control member 960, while facilitating translation of the second control member 960 and/or the first control member 930. For example, the first control portion 920 may slide within the groove 934 (e.g., via the translation surface 918, the surface 956, the surfaces 1026-1027, the retention portion 932, etc.), such that the first control member 930 translates in a first direction (e.g., along the axis 906) and/or the second control member 960 translates in a second direction (e.g., along the axis 908). In some embodiments, an axis of the groove 934 and an axis of the first control portion 920 (e.g., the first surface 1026, and/or a second surface 1027, etc.) are aligned. In other embodiments, an aperture of the groove 934 (e.g., the retention portion 932) and an axis of the control portion aperture 923 are aligned, such that the groove 934 (e.g., the retention portion 932) and the control portion aperture 923 may receive the pin 941 to couple the first control member 930 to the second control member 960.

In some embodiments, the first control member 930 also includes a base, shown as screw 952, having a threaded portion 954. The threaded portion 954 of the screw 952 may be configured to contact a corresponding threaded portion of an adjustment collar 1040. In various embodiments, the threaded portion 954 is a male screw thread configured to be received by a female mating thread (e.g., of the adjustment collar 1040). In some embodiments, the screw 952 also includes one or more apertures (e.g., fluid apertures, bone growth material apertures, etc.). The apertures may facilitate fluid communication (e.g., for the delivery of bone growth material, etc.) between an exterior and an interior of the implant 900.

According to various embodiments, the adjustment collar 1040 is configured to be received within an aperture of one or more components of the implant 900 (e.g., an end member, etc.), and is configured to receive the first control member 930. In some embodiments, the adjustment collar 1040 is rotatably received within one or more components of the implant 900 (e.g., an end member, etc.), and/or is retained via a retention component, shown as retention ring 942. The retention ring 942 may be configured to couple the adjustment collar 1040, and maintain the position of the adjustment collar 1040 relative to one or more components of the implant 900 (e.g., via a groove of an end member). In some embodiments, the adjustment collar 1040 includes additional components, for example, a contact surface 1044 and a threaded aperture 1046. The contact surface 1044 may be configured to receive a tool to facilitate manipulation of the implant 900 (e.g., via a user, etc.). In various embodiments, the contact surface 644 is a raised portion of the adjustment collar 1040, so as to facilitate transmission of an external force (e.g., rotational, etc.) to the adjustment collar 1040. The threaded aperture 1046 may be configured to receive the screw 952 of first control member 930 and translate force thereto. In various embodiments, threaded aperture 1046 includes a female mating thread. In various embodiments, the adjustment collar 1040 is formed of a rigid metal (e.g., cobalt chrome, etc.) or other suitable material, for example to withstand forces (e.g., rotational) transmitted to components of the adjustment collar 1040.

In some embodiments, the implant 900 further includes one or more end members, shown as a first end member 1034 and a second end member 1036. The first end member 1034 and the second end member 1036 may be configured to engage the base member 970 and/or the adjustable member 980, so as to facilitate movement (e.g., up and down, contractive and expansive, etc.) of the base member 970 and/or the adjustable member 980. In various embodiments, the first end member 1034 and the second end member 1036 are coupled to the second control member 960 and/or the first control member 930, and/or are configured to translate along an axis (e.g., the axis 908). For example, the first end member 1034 may be configured to translate along an axis (e.g., the axis 908) in a first direction (e.g., toward the second end member 1036), and the second end member 1036 may be configured to translate along an axis (e.g., the axis 908) in a second direction (e.g., toward the first end member 1034). As the first end member 1034 and/or the second end member 1036 translates along an axis (e.g., the axis 908), the base member 970 and/or the adjustable member 980 may selectively expand or contract, as discussed below.

In some embodiments, the first end member 1034 includes a first control interface 914 and the second end member 1036 includes a second control interface 916. The first control interface 914 and/or the second control interface 916 may include sloped portions configured to contact corresponding sloped portions of the base member 970 and/or the adjustable member 980. For example, the first control interface 914 may be configured to contact the control interface 1070 of the base member 970 and/or the control interface 1072 of the adjustable member 980, and the second control interface 916 may be configured to contact the control interface 1071 of the base member 970 and/or the control interface 1073 of the adjustable member 980. In various embodiments, the first control interface 914 and/or the second control interface 916 is/are configured to contact control interfaces 1070-1073, so as to cause vertical translation or movement (e.g., up and down, expansive and contractive) of the base member 970 and/or the adjustable member 980, for example in response to movement of the first control member 930 or the second control member 960 relative to the other.

As discussed above, the rate of movement of the base member 970 and/or the adjustable member 980 may be adjusted by modifying the slope of components of the first control interface 914 and/or the second control interface 916. In some embodiments, the first control interface 914 and/or the second control interface 916 include a projection or protrusion. The projection or protrusions may be configured to be received by a void or space in the base member 970 and/or the adjustable member 980, for example to facilitate alignment of the first end member 1034 and/or the second end member 1036 relative to the base member 970 and/or the adjustable member 980 (e.g., lateral alignment during horizontal translation of the first end member 1034 and/or the second end member 1036). In other embodiments, the first control interface 914 and/or the second control interface 916 include additional components (e.g., channels, grooves, protrusions, etc.), for example to facilitate alignment of the first end member 1034 and/or the second end member 1036 with one or more components of the implant 900 (e.g., the base member 970, the adjustable member 980, etc.).

In some embodiments, the first end member 1034 includes a bore 1042 and one or more apertures 1043 (shown in FIG. 43), which facilitate coupling the first end member 1034 to one or more components of the implant 900. For example, the bore 1042 may be configured to receive the end portion 912 of the second control member 960, so as to retain the second control member 960 relative to the first end member 1034. The aperture 1043 may be configured to receive the pin 961, so as to couple the first end member 1034 to the second control member 960. In various embodiments, the end portion 912 is received by the bore 1042, and the pin 961 is inserted into the aperture 1043 of the first end member 1034 and the aperture 943 of the end portion 912, so as to couple the first end member 1034 to the second control member 960.

In some embodiments, the second end member 1036 includes an adjustment aperture 1048 having one or more grooves. The adjustment aperture 1048 may be substantially circular, and may extend into the second end member 1036 along an axis (e.g., the axis 906). In various embodiments, the adjustment aperture 1048 is configured to receive one or more components of the implant 900, for example, the first control member 930, the adjustment collar 1040, and/or the retention ring 942. As discussed above, the adjustment aperture 1048 may receive the first control member 930, which may be coupled to the second control member 960 (e.g., at an internal portion of the implant 900), as discussed above. The adjustment collar 1040 may be coupled to the retention ring 942, and the adjustment collar 1040 and the retention ring 942 may be received by the adjustment aperture 1048 (e.g., via the one or more grooves). In some embodiments, the retention ring 942 is received by the adjustment aperture 1048, and is configured to maintain a position of the adjustment collar 1040 relative to the second end member 1036. As discussed above, the adjustment collar 1040 is rotatably received by the adjustment aperture 1048, and is configured to receive the screw 952 of the first control member 930. In various embodiments, the adjustment collar 1040 is manipulated (e.g., rotated, etc.), causing translation of the first control member 930 relative to the second end member 1036 (e.g., along the axis 906), and movement of the first end member 1034 and/or the second end member 1036 (e.g., along the axis 908), thereby causing vertical translation or movement (e.g., up and down, expansive and contractive, etc.) of the base member 970 and/or the adjustable member 980.

Figure 35:
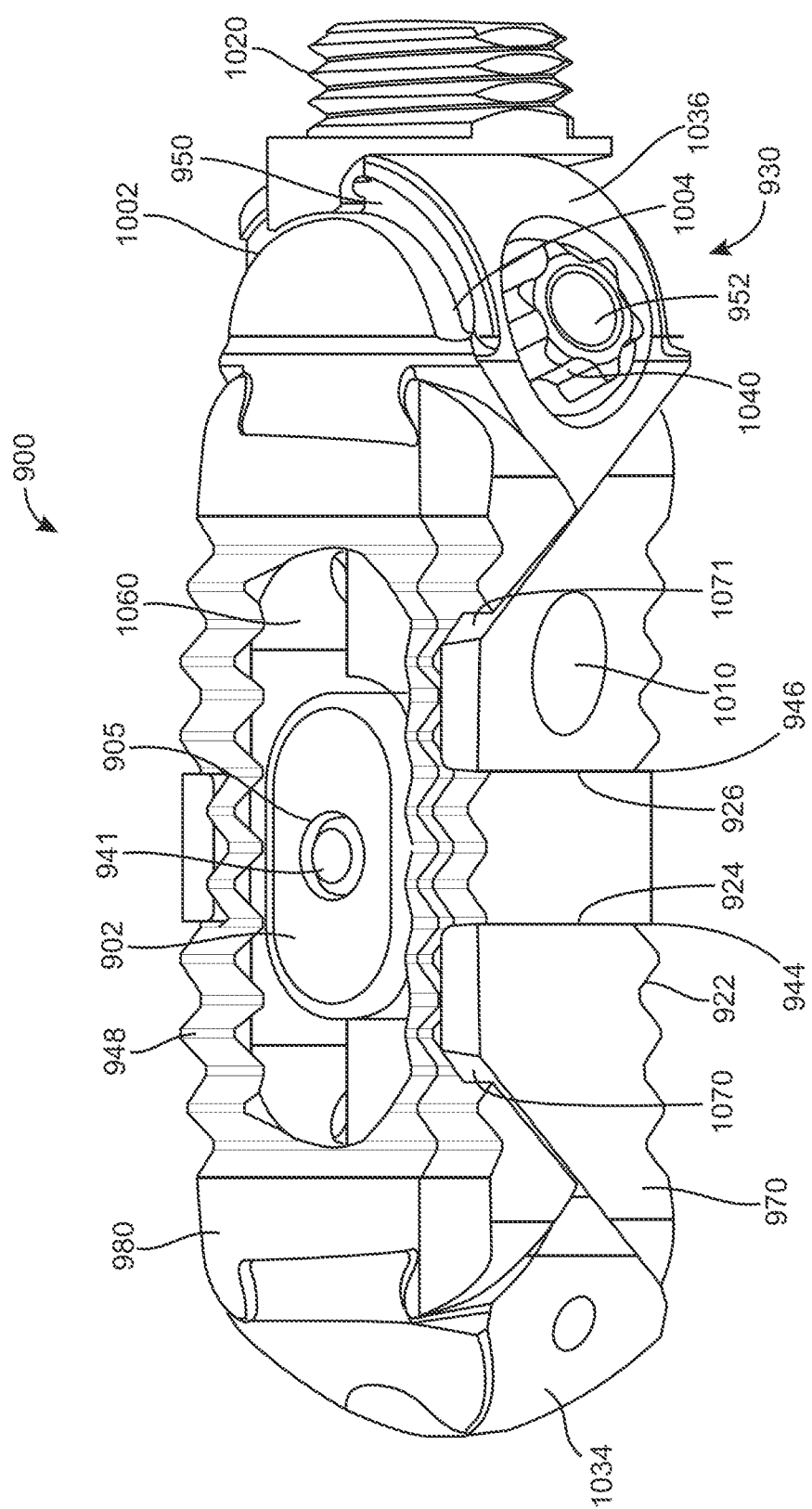
FIG. 35 is a perspective view of a steerable expandable implant, according to another embodiment.
Figure 36:
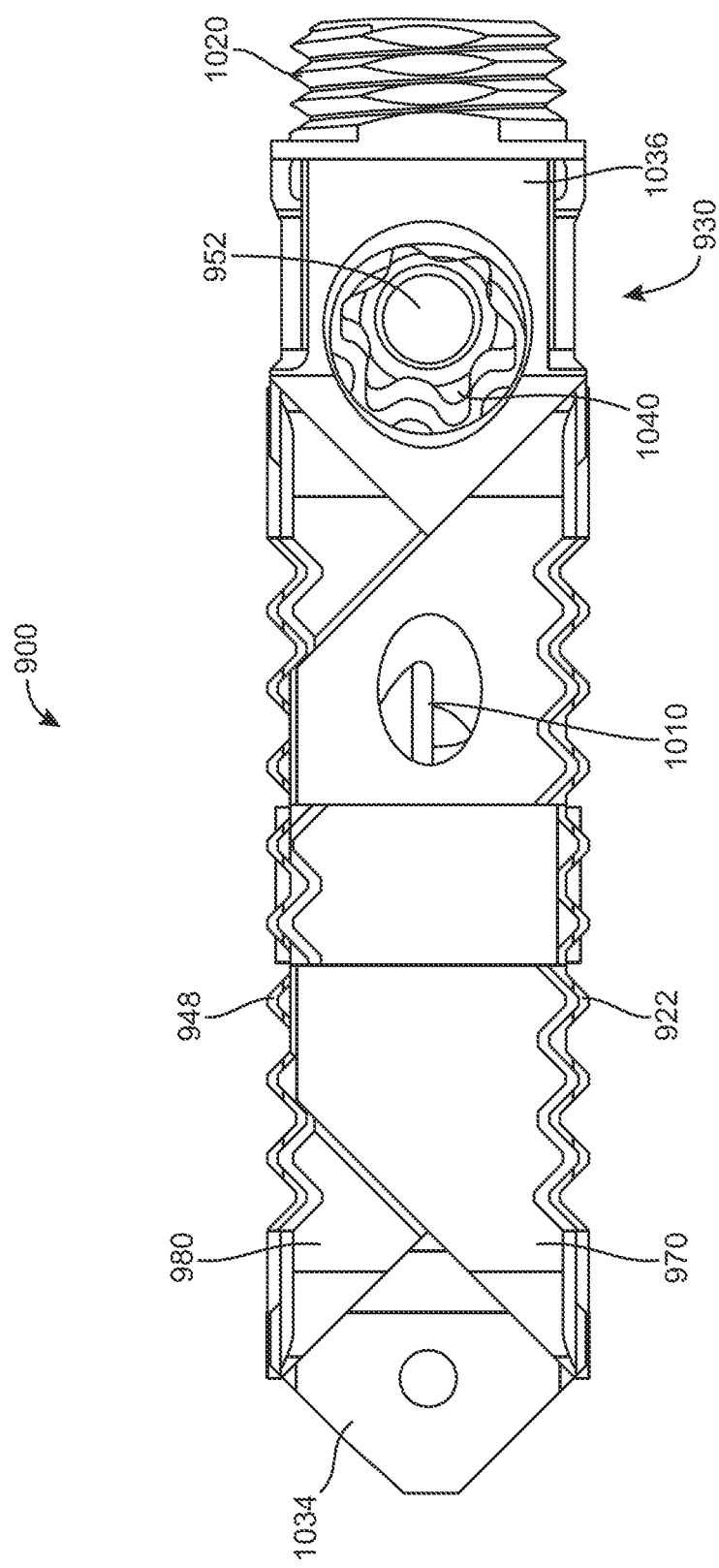
FIG. 36 is a side view of the steerable expandable implant of FIG. 35, according to one embodiment.
Figure 37:
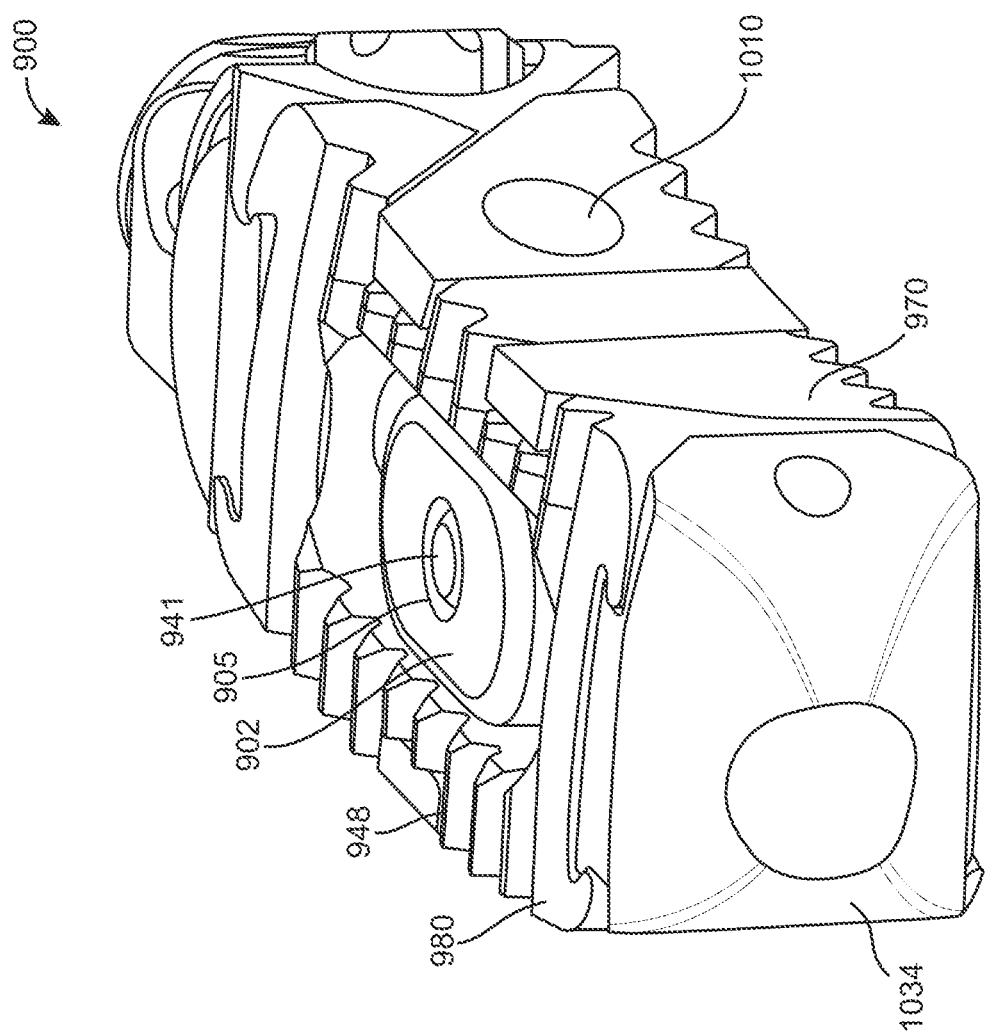
FIG. 37 is a perspective end view of the steerable expandable implant of FIG. 35, according to one embodiment.
Figure 38:
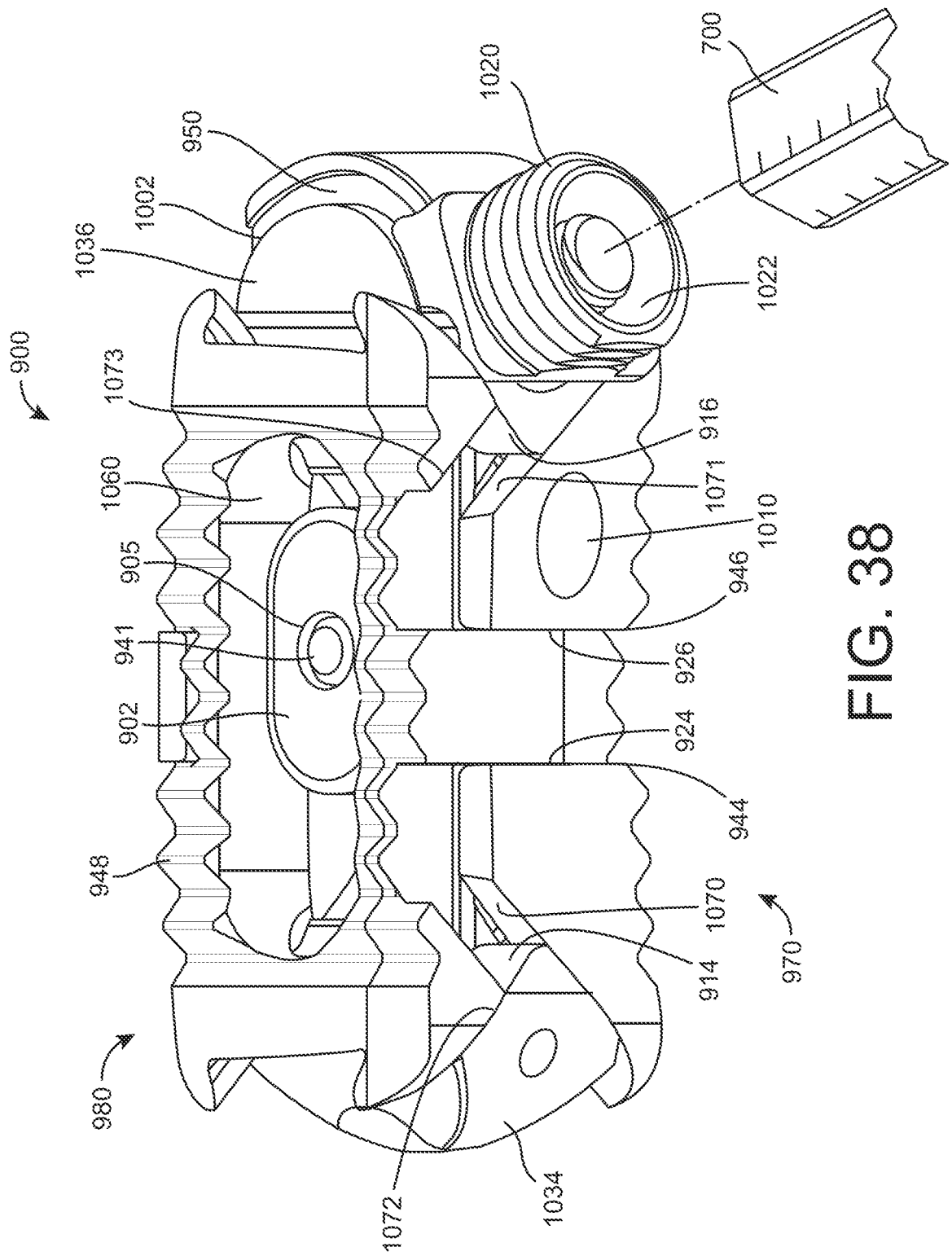
FIG. 38 is a perspective view of the steerable expandable implant of FIG. 35 in an expanded position, according to one embodiment.
Figure 39:
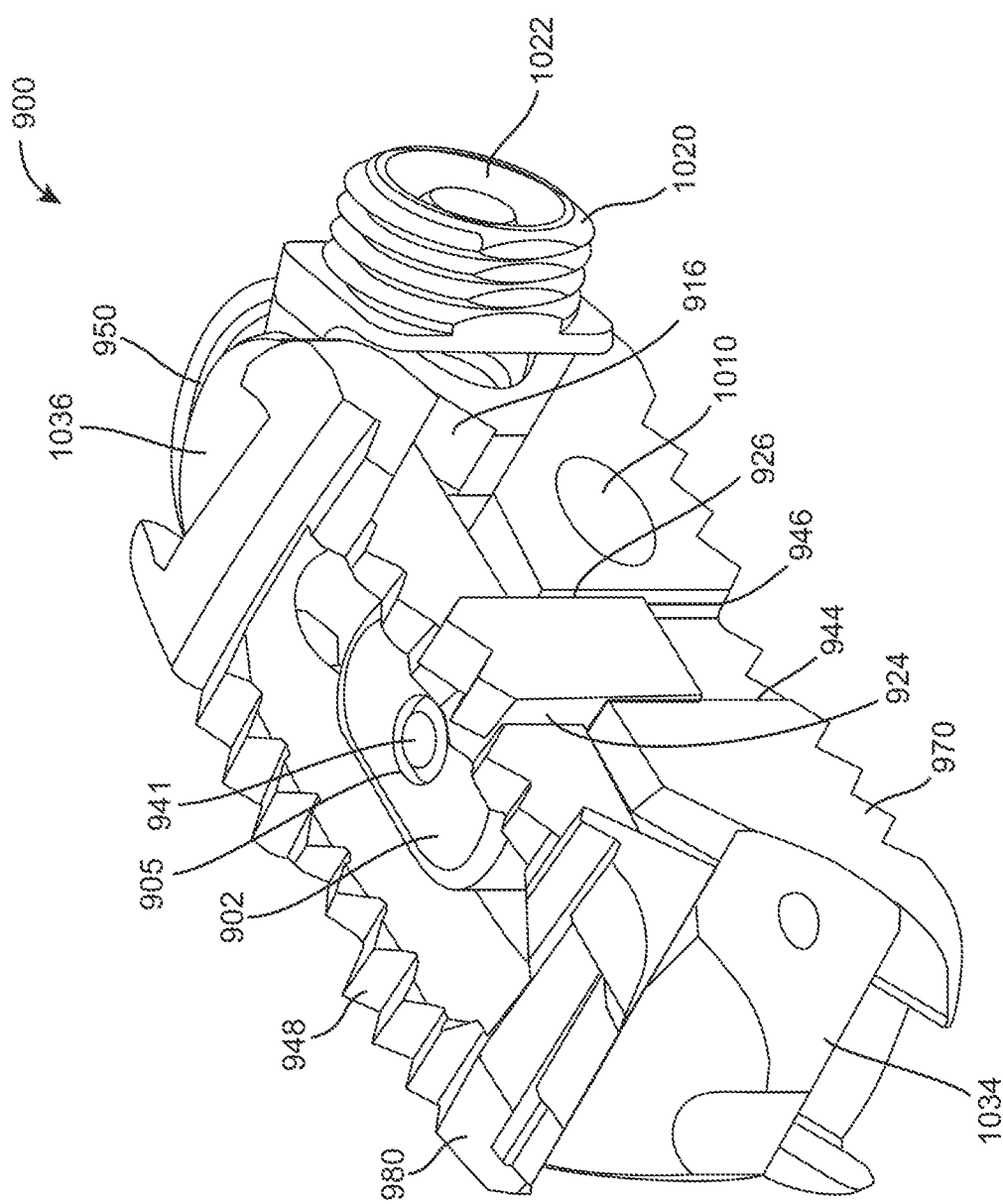
FIG. 39 is a perspective end view of the steerable expandable implant of FIG. 35 in an expanded position, according to one embodiment.
Figure 40:
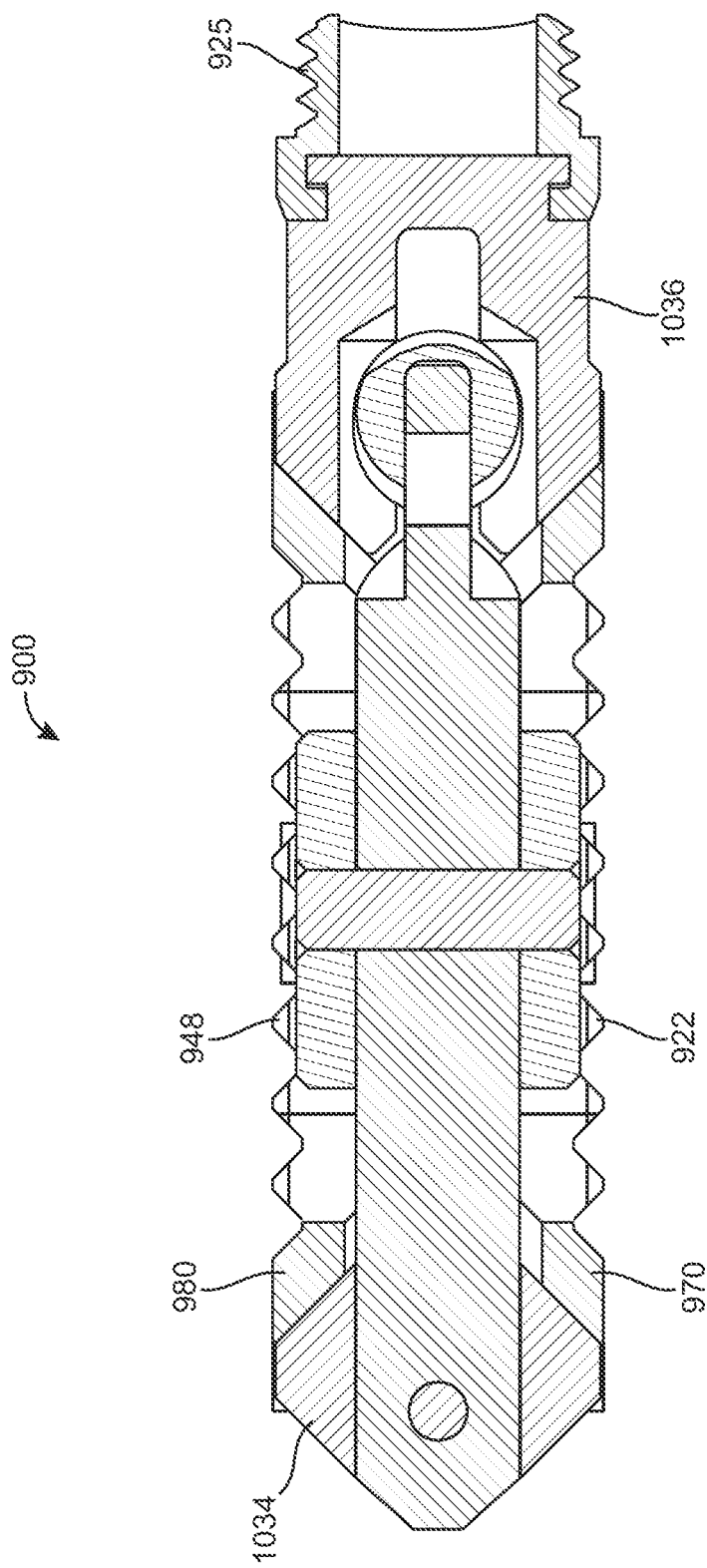
FIG. 40 is a cutaway side view of the steerable expandable implant of FIG. 35, according to one embodiment.

In various embodiments, the second end member 1036 also includes a guide channel 950 configured to couple one or more components of the implant 900. For example, the guide channel 950 may receive a pivot member 1020. According to some embodiments, the pivot member 1020 is configured to rotate between a first position (as shown in FIGS. 35-36) and a second position (as shown in FIGS. 38-39). In various embodiments, the guide channel 950 includes one or more limits, shown as a limit 1002 and a limit 1004. Rotation of the pivot member 1020 may be limited by the limit 1002 and/or the limit 1004, for example, the limit 1002 may prevent a user from rotating the pivot member 1020 further than the first position, and/or the limit 1004 may prevent a user from rotating the pivot member 1020 further than the second position.

In various embodiments, the pivot member 1020 is coupled to the second end member 1036 (e.g., via the guide channel 950), such that the pivot member 1020 is translationally fixed relative to the second end member 1036. The pivot member 1020 may include an aperture 1022, which may be configured to couple a portion of a tool 1000 (e.g., as shown in FIG. 38). For example, the pivot member 1020 and/or the aperture 1022 may include threading (e.g., internal threading, external threading, etc.), configured to couple corresponding threading portion of a tool (as shown in FIG. 38). In some embodiments, an axis of the aperture 1022 is offset from the axis of the first control member 930 when the pivot member 1020 is in the first position, and/or is aligned with the axis of the second control member 960 when the pivot member 1020 is in the first position. In some embodiments, the axis of the aperture 1022 is aligned with the axis of the first control member 930 when the pivot member is in the second position, and/or is offset from the axis of the second control member 960 when the pivot member 1020 is in the second position. In other embodiments, the axis of the aperture 1022 of the pivot member 1020 is coaxially aligned with the first control member 930 when the pivot member is in the second position, so as to facilitate adjustment of the implant 900. In this regard, the pivot member 1020 is configured to facilitate positional adjustment of the implant 900, as discussed above.

A non-limiting example of operation of implant 900 is as follows. A tool (e.g., the tool 1000, shown in FIG. 38), such as a coaxial manipulation device, may be attached to implant 900 via the pivot member 1020. A user may align the manipulation device to implant 900 using coupling aperture 1010. The user may turn pivot member 1020 from the first position (e.g., as shown in FIGS. 35-36) to the second position (e.g., as shown in FIGS. 38-39) via the aperture 1022, while changing the orientation of the implant 900. In the second position, the user may engage adjustment collar 1020 using the manipulation device. Rotation of the adjustment collar 1020 may cause translation of the first control member 930 (e.g., along axis 906 relative to the second end member 1036). The first control member 930 may engage the second control member 960 (e.g., via the pin 941, the retention portion 932, the first control portion 920, etc.), causing translation or other movement of the first end member 1034 and/or the second end member 1036 (e.g., along the axis 908). Translation of the first end member 1034 and/or the second end member 1036 causes first control interface 914 and/or second control interface 916 to engage control interfaces 1070-1073 of the base member 970 and/or the adjustable member 980, thereby causing expansion or contraction of the implant 900. Rotation of the adjustment collar 1040 in a first direction may cause expansion of the implant 900, while rotation of the adjustment collar 1040 in a second direction may cause contraction of the implant 900.

Figure 44:
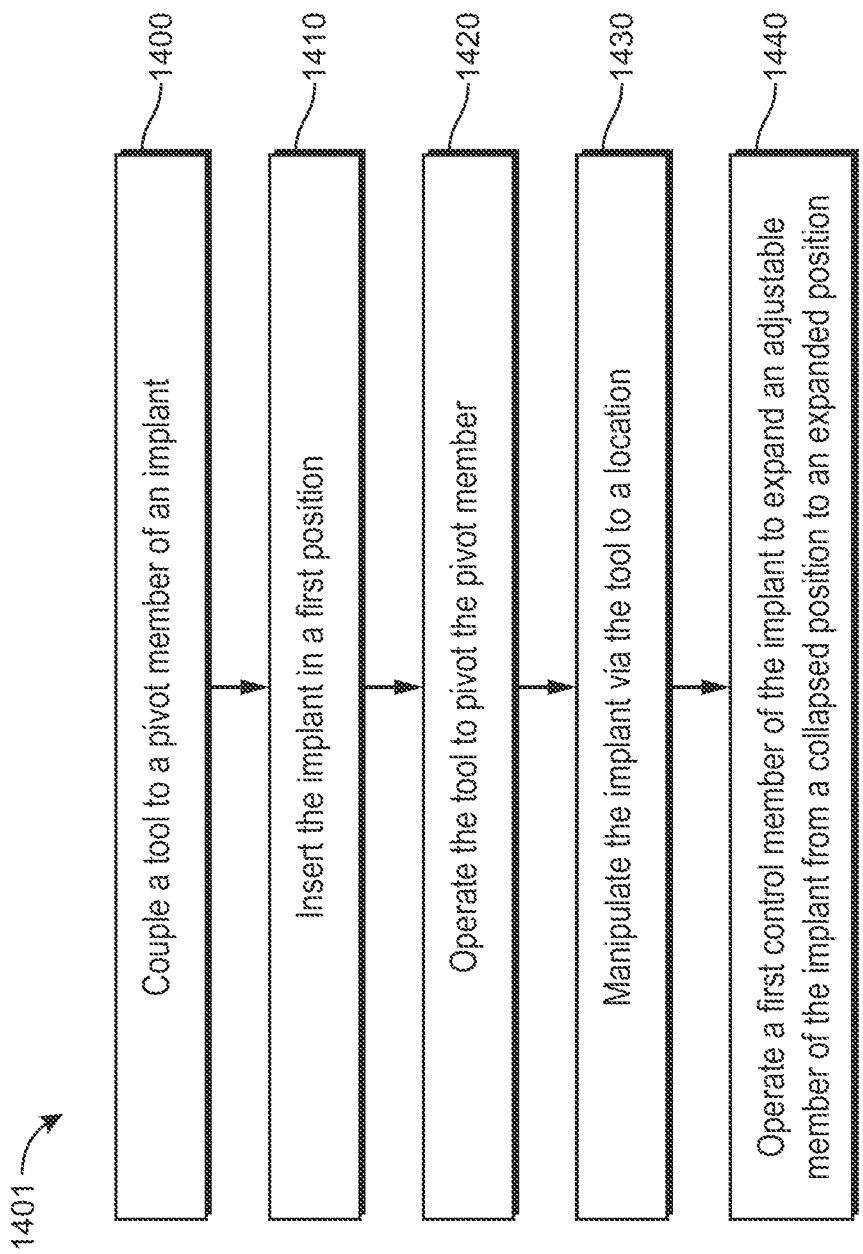
FIG. 44 is a flow chart of a process for positioning an implant, according to one embodiment.

Referring now to FIG. 44, method 1401 of positioning an implant is shown, according to an embodiment. Method 1401 may be used with the implants disclosed herein (e.g., implant 100, implant 300, implant 500 etc.), or another implant altogether. Referring now to method 1401 generally, method 1401 may be used to more easily insert and position an implant between adjacent bodies of bone. For example, method 1401 may be used to implant or insert an implant into a human spine adjacent upper and lower vertebrae of the spine.

At step 1400, a user may connect a tool to a pivot member of an implant. For example, the user may connect a manipulation device (e.g., tool 700, etc.) to a steerable control member of the implant. In some embodiments, the steerable control member is the same as or similar to the control member 200, control member 400, pivot member 620, and/or pivot member 1020. In some embodiments, the steerable control member is in a first position that configures the implant in a compact orientation. For example, the steerable control member may align the implant to be inserted lengthwise such that the implant is generally axially aligned with the manipulation device. At step 1410, the user may insert the implant into the insertion region. For example, the implant may be inserted through an incision. In other embodiments, the implant may be inserted in a first position. For example, the implant may be inserted laterally. That is, the implant may be oriented such that the smallest cross-sectional area must fit through the incision gap. In some embodiments, step 1410 roughly positions the implant before the implant is reoriented to a different orientation more convenient to positioning and manipulation.

Figure 4:
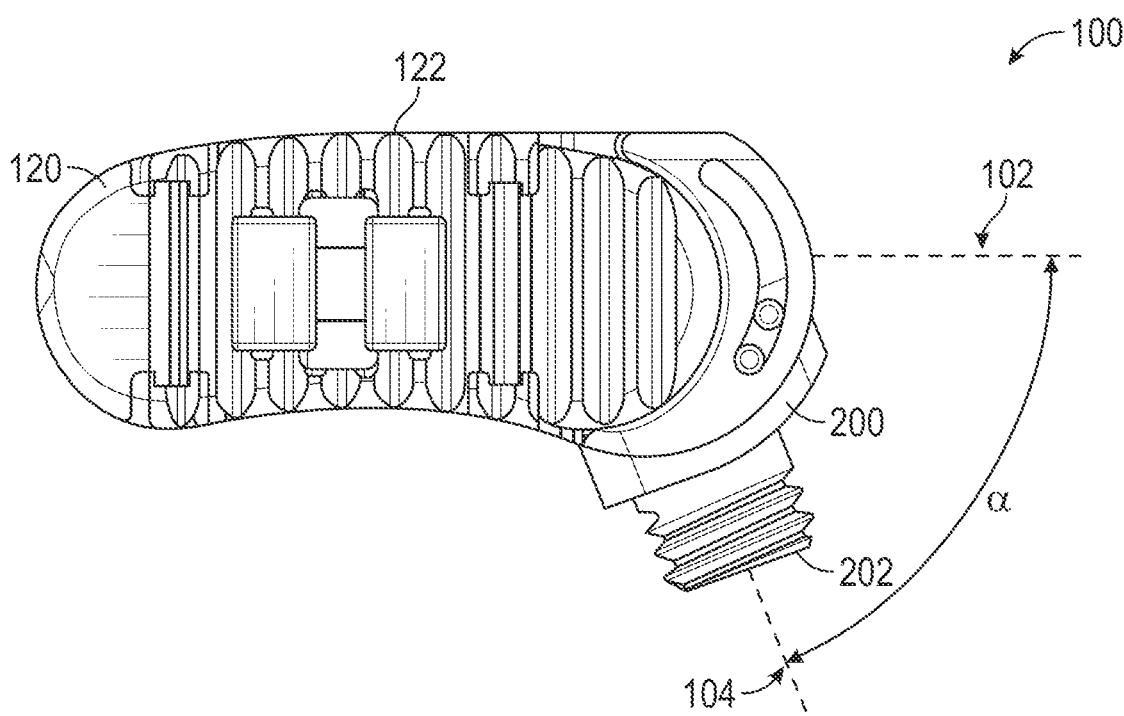
FIG. 4 is a top view of the steerable expandable implant of FIG. 1 in the second configuration, according to one embodiment.
Figure 5:
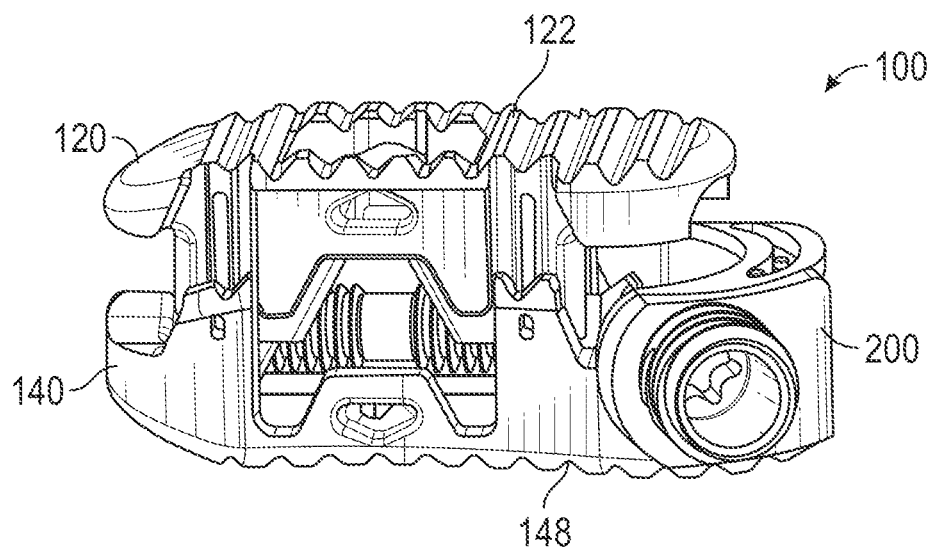
FIG. 5 is a perspective view of the steerable expandable implant of FIG. 1 in an expanded position, according to one embodiment.
Figure 6:
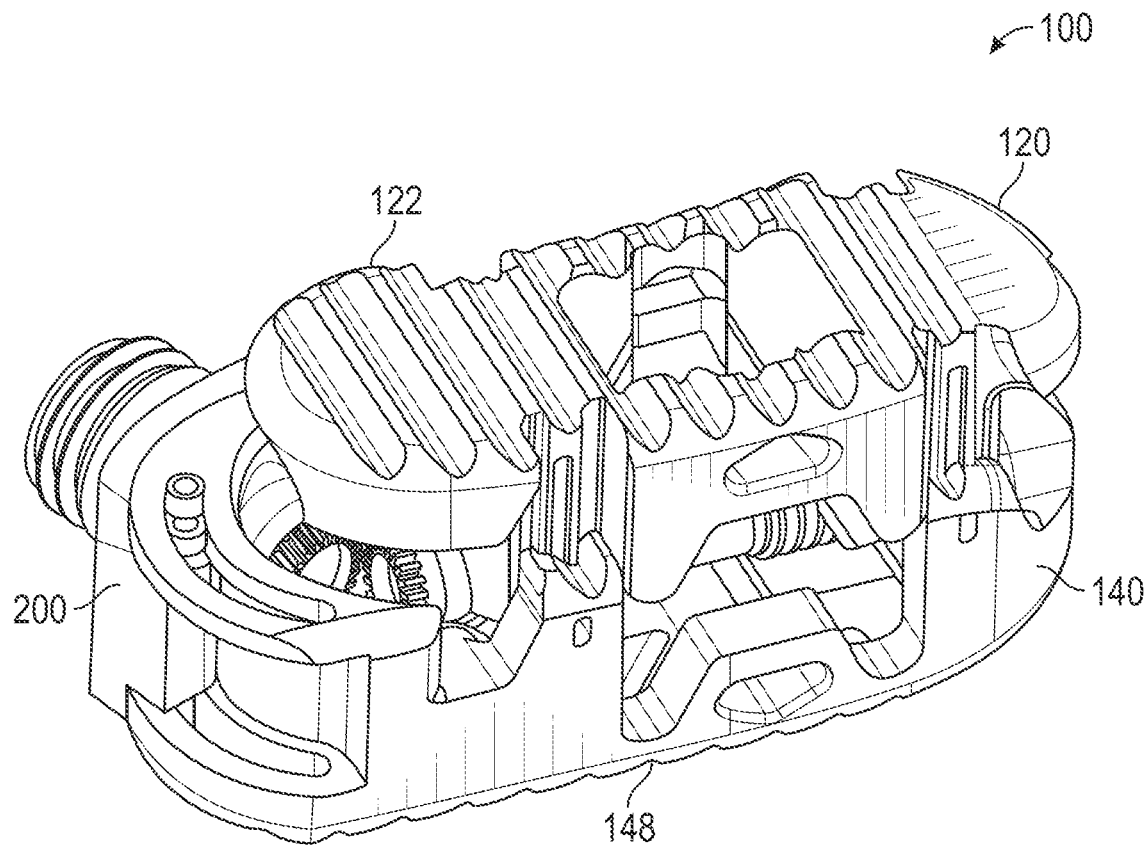
FIG. 6 is another perspective view of the steerable expandable implant of FIG. 1 in an expanded configuration, according to one embodiment.

At step 1420, the user may operate the tool to pivot the pivot member. For example, the user may operate the steerable control member of the implant to move the steerable control member to a second position. In some embodiments, the steerable control member is the same as or similar to first control shaft 130 and/or first control shaft 330. In some embodiments, the second position is such that the implant is oriented at an angle to the manipulation device for alignment with a final implantation location, as seen in FIG. 4, for example. Operation of the steerable control member may change an orientation of the implant such that the axis of the implant changes from being generally parallel with the manipulation device to being generally slanted (e.g., offset by 45°) from the manipulation device. In some embodiments, the user operates the manipulation device to move the steerable control member (e.g., control member 200, control member 400, pivot member 620, pivot member 1020) to the second position. At step 1430, the user may manipulate the implant, using the tool, to a location. For example, the user may steer the implant into an anterior position on a vertebral body of the patient. At step 1440, the user may operate a first control member (e.g., first control shaft 130, first control shaft 330, adjustment collar 640, adjustment collar 1040) of the implant to expand an adjustable member of the implant from a collapsed position to an expanded position. In some embodiments, the user may connect the manipulation device to the control shaft before operation. For example, the user may couple a control member of the tool to a control member of the implant. In some embodiments, the expanded position is similar to the expanded position shown in FIG. 5. In an expanded position, the implant may contact adjacent portions of bone to provide therapeutic benefits. For example, the implant may stabilize vertebra and/or promote bone grow.

It is important to note that the construction and arrangement of the elements of the various implants and implant components as shown in the embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

Steerable expandable implants, such as implant 100, implant 300, implant 500, implant 800, and implant 900 as disclosed herein, offer many advantages over traditional implants. Steerable expandable implants (e.g., implant 100, implant 300, implant 500, implant 800, implant 900) may change a position of a control member (e.g., manipulation connector 202, manipulation connector 402, pivot member 620, pivot member 1020, etc.) to better orient the implant into an implantation location (i.e., a location between vertebrae of the spine). Traditional implants may have to be manually oriented for implantation. For example, an implant may be manually pushed or twisted using forceps into an implantation location, which is not conducive to microsurgery, arthroscopic surgery, or the like. In addition, operation of a portion of the steerable expandable implant (e.g., manipulation connector 202, manipulation connector 402, pivot member 620, pivot member 1020, etc.) may change a position of the implant. Additionally or alternatively, operation of the portion of the steerable expandable implant may expand the implant. Traditional implants lack a single control mechanism to control multiple aspects of the implant. In contrast, the steerable expandable implants disclosed herein (e.g., implant 100, implant 300, implant 500, implant 800, implant 900, etc.), can control orientation and expansion of the implant from a single mechanism, reducing the complexity of implantation and the number of specialized tools required. Furthermore, the steerable expandable implants disclosed herein may be inserted in a compact orientation (e.g., laterally) to reduce the size of an insertion necessary to fit the implant before being oriented into a final orientation (e.g., horizontally) for positioning into an implantation location.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

What is claimed is:

1. A steerable expandable implant, comprising:
   a lower support member configured to engage a first portion of bone;
   an upper support member coupled to the lower support member and configured to engage a second portion of bone, the upper support member movable relative to the lower support member between a collapsed position and an expanded position;
   a first control member coupled to the lower support member, wherein manipulation of the first control member causes the lower support member to move relative to the upper support member between the collapsed position and the expanded position, wherein a second control member is coupled to the first control member, and wherein an axis of the second control member is angularly offset relative to an axis of the first control member, and the axis of the second control member is aligned with an axis of the lower support member and an axis of the upper support member; and
   a pivot member configured to receive a tool such that the tool and the pivot member are rotatable relative to the lower support member between a first position and a second position, and wherein the pivot member includes an aperture and wherein an axis of the aperture is angularly offset from an axis of the first control member in the first position and the axis of the aperture is angularly aligned with the axis of the first control member in the second position.

2. The steerable expandable implant of claim 1, wherein the first control member is pivotally fixed relative to the lower support member and the upper support member.

3. The steerable expandable implant of claim 1, wherein the axis of the aperture is co-axially aligned with the axis of the first control member in the second position.

4. The steerable expandable implant of claim 1, wherein the upper support member is vertically movable relative to the lower support member between the collapsed position and the expanded position, and wherein the pivot member is vertically fixed relative to the second control member and the first control member.

5. The steerable expandable implant of claim 1, wherein the axis of the second control member is aligned with the axis of the aperture when the pivot member is in the first position.

6. The steerable expandable implant of claim 1, wherein the lower support member further includes an alignment portion configured to receive an alignment member of the tool to position the tool relative to the lower support member.

7. The steerable expandable implant of claim 6, wherein an axis of the alignment portion is angularly aligned with the axis of the first control member.

8. The steerable expandable implant of claim 1, further comprising an adjustment member threadingly coupled to the first control member, wherein rotation of the adjustment member causes movement of the first control member.

9. A steerable expandable implant, comprising:
   a lower support member configured to engage a first portion of bone;
   an upper support member coupled to the lower support member and configured to engage a second portion of bone, the upper support member movable relative to the lower support member between a collapsed position and an expanded position;
   a second control member coupled to the lower support member, wherein manipulation of a first control member causes the second control member to move relative to the first control member, and the lower support member to move relative to the upper support member between the collapsed position and the expanded position, and wherein an axis of the second control member is angularly offset relative to an axis of the first control member and the axis of the second control member is aligned with an axis of the lower support member and an axis of the upper support member; and
   a pivot member configured to receive a tool such that the tool and the pivot member are rotatable relative to the lower support member between a first position and a second position, and wherein the pivot member includes an aperture and wherein an axis of the aperture is angularly aligned with an axis of the second control member in the first position and the axis of the aperture is angularly offset from the axis of the second control member in the second position.

10. The steerable expandable implant of claim 9, wherein the first control member is pivotally fixed relative to the lower support member and the upper support member.

11. The steerable expandable implant of claim 9, wherein the axis of the aperture is co-axially aligned with the axis of the first control member in the second position.

12. The steerable expandable implant of claim 9, wherein the upper support member is vertically movable relative to the lower support member between the collapsed position and the expanded position, and wherein the pivot member is vertically fixed relative to the second control member and the first control member.

13. A steerable expandable implant, comprising:
a lower support member configured to engage a first portion of bone;
an upper support member coupled to the lower support member and configured to engage a second portion of bone, the upper support member movable relative to the lower support member between a collapsed position and an expanded position;
a first control member coupled to the lower support member, wherein manipulation of the first control member causes the lower support member to move relative to the upper support member between the collapsed position and the expanded position;
a second control member slidably coupled to the first control member, wherein an axis of the second control member is offset relative to an axis of the first control member, and wherein the axis of the second control member is aligned with an axis of the lower support member and an axis of the upper support member; and
a pivot member configured to receive a tool such that the tool and the pivot member are rotatable relative to the lower support member between a first position and a second position, and wherein the pivot member includes an aperture and wherein an axis of the aperture is angularly offset from an axis of the first control member in the first position and the axis of the aperture is angularly aligned with the axis of the first control member in the second position.

14. The steerable expandable implant of claim 13, wherein the first control member is pivotally fixed relative to the lower support member and the upper support member.

15. The steerable expandable implant of claim 13, wherein the axis of the aperture is co-axially aligned with the axis of the first control member in the second position.

16. The steerable expandable implant of claim 13, wherein the upper support member is vertically movable relative to the lower support member between the collapsed position and the expanded position, and wherein the pivot member is vertically fixed relative to the second control member and the first control member.

* * * * *